US012740985B2

(12) United States Patent
Lin et al.

(10) Patent No.: US 12,740,985 B2
(45) Date of Patent: Sep. 22, 2026

(54) SMALL MOLECULE LIVER X RECEPTOR MODULATORS AND USES THEREOF

(71) Applicant: University of Houston System, Houston, TX (US)

(72) Inventors: Chin-Yo Lin, Kingwood, TX (US); Scott Gilbertson, Pearland, TX (US)

(73) Assignee: UNIVERSITY OF HOUSTON SYSTEM, Houston, TX (US)

( * ) Notice: Subject to any disclaimer, the term of this patent is extended or adjusted under 35 U.S.C. 154(b) by 1057 days.

(21) Appl. No.: 17/637,562

(22) PCT Filed: Sep. 1, 2020

(86) PCT No.: PCT/US2020/048908
§ 371 (c)(1),
(2) Date: Feb. 23, 2022

(87) PCT Pub. No.: WO2021/046034
PCT Pub. Date: Mar. 11, 2021

(65) Prior Publication Data

US 2022/0273658 A1 Sep. 1, 2022

Related U.S. Application Data

(60) Provisional application No. 62/896,068, filed on Sep. 5, 2019.

(51) Int. Cl.
*A61K 31/513* (2006.01)
*A61P 35/00* (2006.01)

(52) U.S. Cl.
CPC ............ *A61K 31/513* (2013.01); *A61P 35/00* (2018.01)

(58) Field of Classification Search
CPC .............................. A61K 31/513; A61P 35/00
See application file for complete search history.

(56) References Cited

FOREIGN PATENT DOCUMENTS

| | | | |
|---|---|---|---|
| CN | 107721975 | 2/2018 | |
| EP | 1645556 | 4/2006 | |
| WO | 00/43373 | 7/2000 | |
| WO | 2010/088450 | 8/2010 | |
| WO | WO-2010088450 A2 * | 8/2010 | ................ A61P 5/48 |

OTHER PUBLICATIONS

Bando, K. et al, Synthesis and evaluation of radiolabeled piperazine derivatives of vesamicol as SPECT agents for cholinergic neurons Nuclear Medicine and Biology 28 (2001) 251-260 (Year: 2001).*

Notification of Transmittal of the International Search Report and The Written Opinion of the International Search Authority—The European Patent Office—mailed Dec. 8, 2020, for PCT/US20/48908, 24 pages.

Chekanov, et al., "Design, synthesis and biological evaluation of 2-aminopyrimidinones and their 6-aza-analogs as a new class of CK2 inhibitors", Journal of Enzyme Inhibition and Medicinal Chemistry, 2013, 9 pages.

Database Registry [Online] Chemical Abstracts Service, Chemcats: XP002801090, XP002801091, XP002801092, XP002801093, XP002801094, XP002801095, XP002801096, XP002801097, XP002801098, XP002801099, XP002801100, XP002801101, XP002801102, XP002801103, XP002801104, 2007, 15 pages.

Flaveny, et al., "Broad Anti-tumor Activity of a Small Molecule that Selectively Targets the Warburg Effect and Lipogenesis", Cancer Cell, vol. 28, 2015, pp. 42-56.

Karaboga, et al., "Screening of Focused Compound Library Targeting Liver X Receptors in Pancreatic Cancer Identified Ligands with Inverse Agonist and Degrader Activity", ACS Chemical Biology, 2020, 13 pages.

Notification of Transmittal of the International Preliminary Report on Patentability mailed Mar. 17, 2022, for PCT/US20/48908, 13 pages.

* cited by examiner

*Primary Examiner* — Samantha L Shterengarts
*Assistant Examiner* — Ernesto Valle
(74) *Attorney, Agent, or Firm* — Jackson Walker LLP

(57) ABSTRACT

Small molecule liver X receptor (LXR) modulators, and derivatives thereof, exhibit activity against tumor cells and less or no activity against dividing non-malignant cells, target the liver X receptor and disrupt key metabolic pathways preferred by cancer cells, and activate a newly discovered cell death mechanism which is distinct from the cell death induced by chemotherapeutic agents. These compounds can thus be a less toxic alternative to chemotherapy and can be used in combination with chemotherapy to increase efficacy and decrease the likelihood of cancer cells developing resistance. Moreover, they can be used as second-line treatments when chemotherapies are ineffective or if cancer cells develop resistance over time.

4 Claims, 42 Drawing Sheets

KD-01-55

KD-01-74

KD-01-80

KD-01-89

KD-01-95

KD-01-104

KD-01-107

KD-01-109

KD-01-114

KD-01-43 KD-01-45 KD-01-57 KD-01-59

KD-01-38 KD-01-64 KD-01-67 KD-01-68

KD-010-69 KD-01-71 KD-01-72

GW3965
TO901317
RGX-104
SR9243
1E5
3A4

KD-01-39

FIG. 8 – cont'd
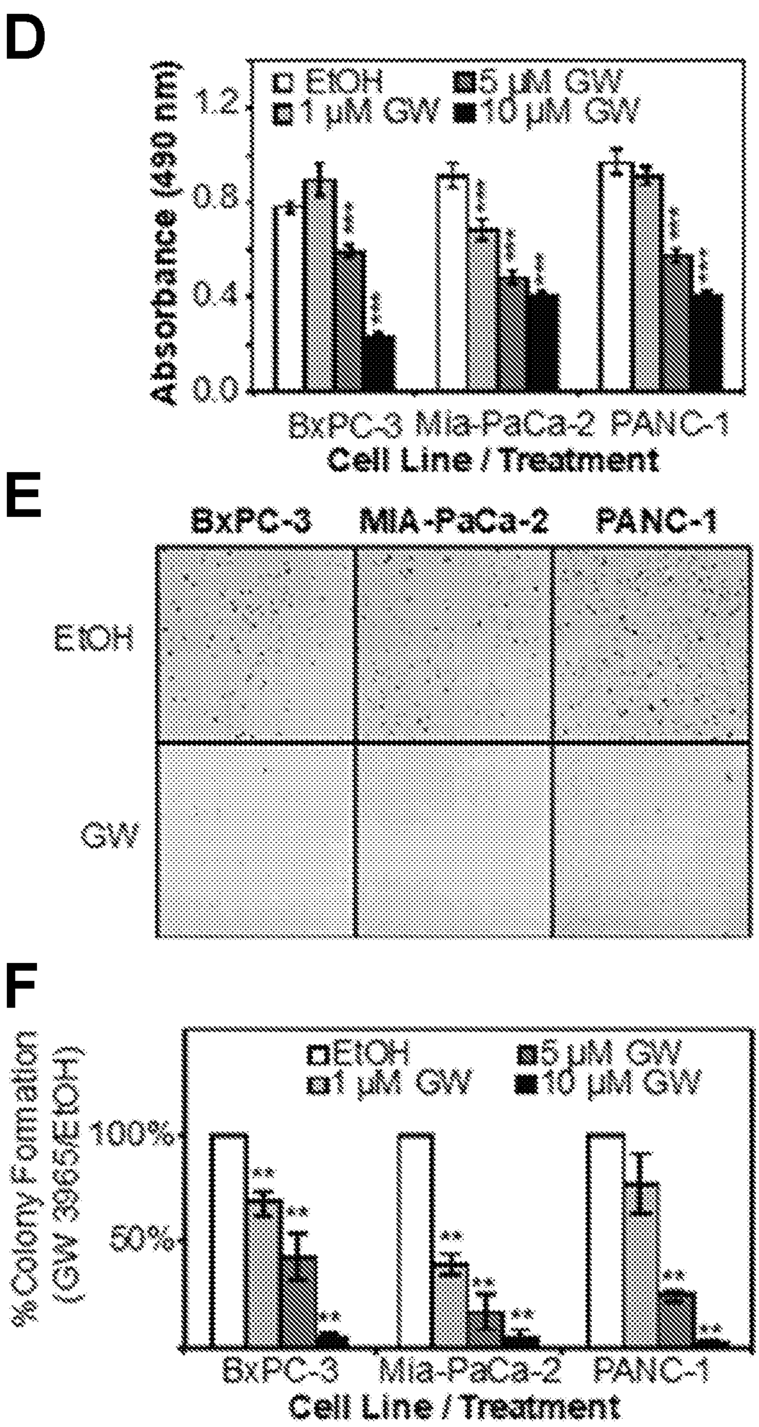

B

Total Flux/cell
1.60E+09
1.40E+09
1.20E+09
1.00E+09
8.00E+08
6.00E+08
4.00E+08
2.00E+08
0.00E+00
Ctrl
GW3965 (40mg/kg)
GW3965 (80mg/kg)
0W
1W
2W
Time in weeks FIG. 9 – cont'd
C
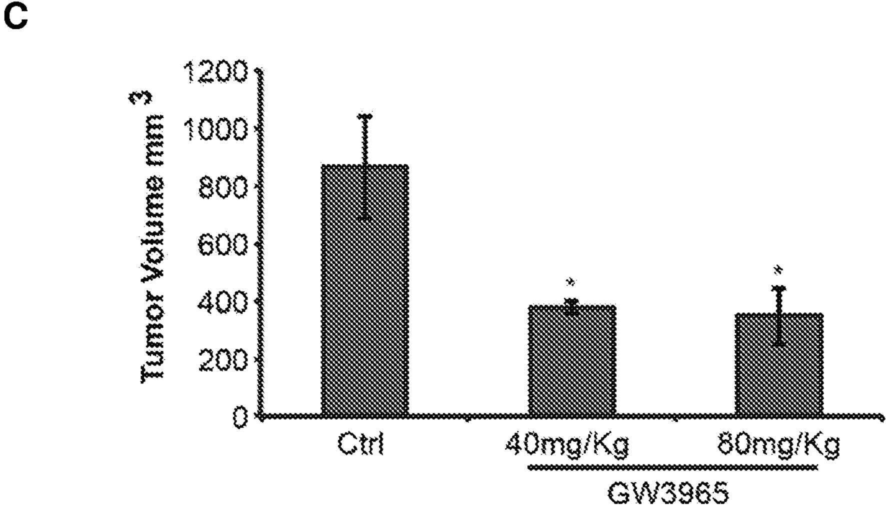
D
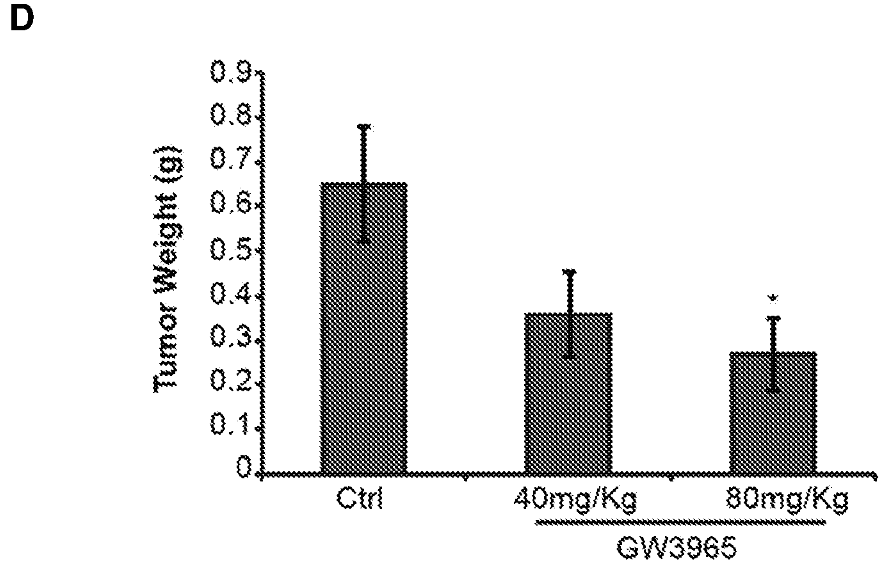

FIG. 11 – cont'd
B
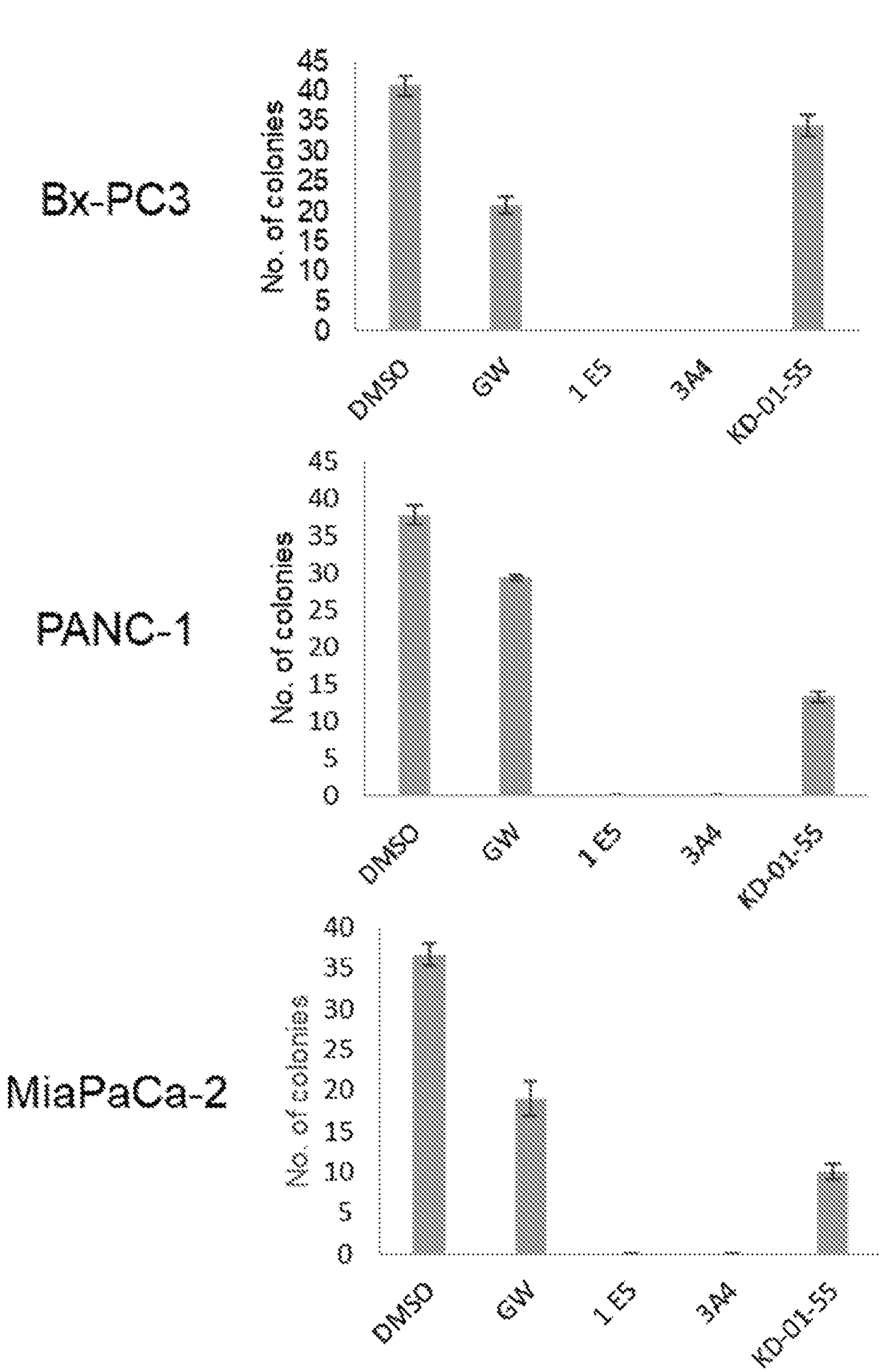

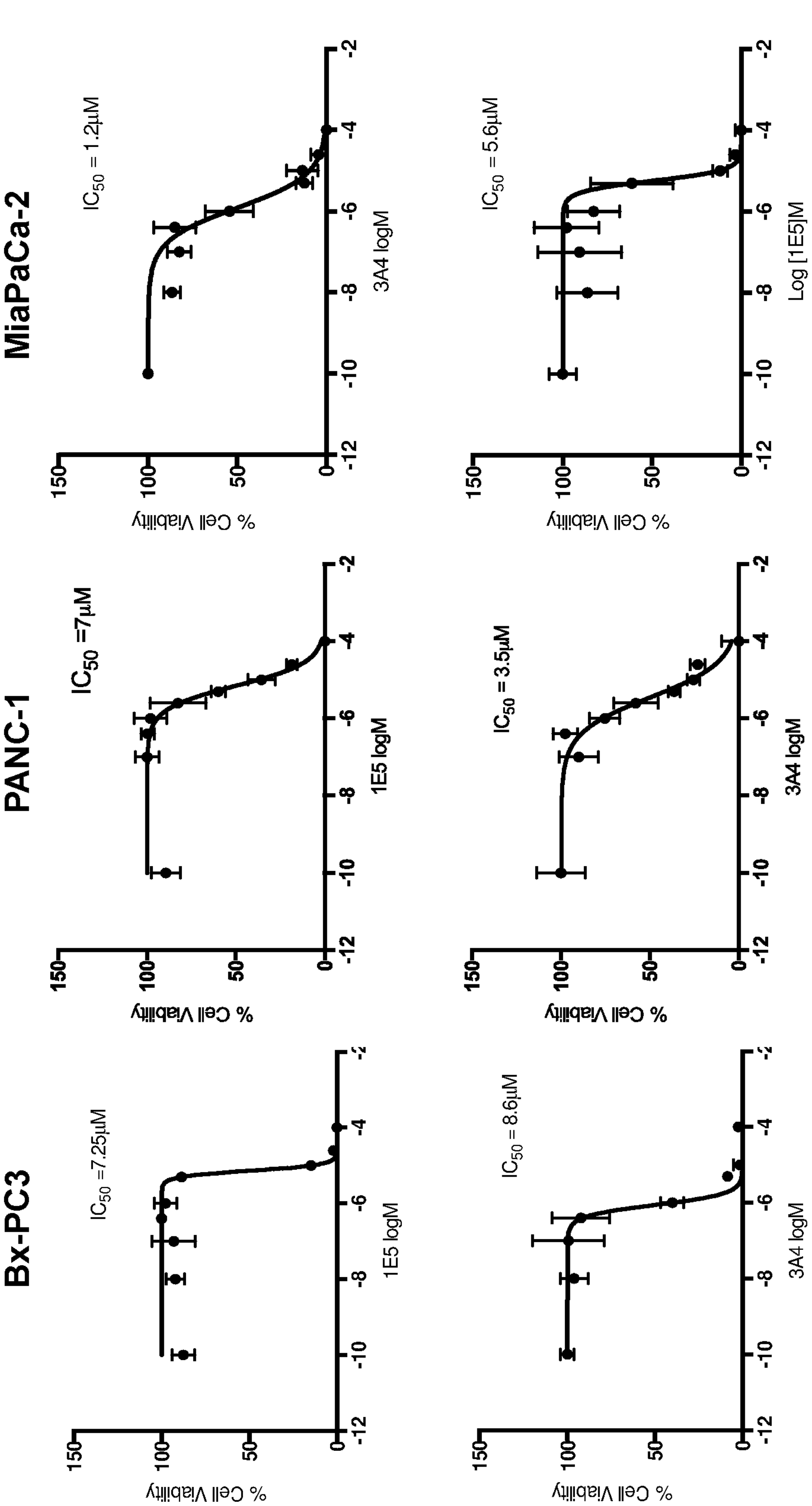
FIG. 13 – cont'd

A

B

C

A

B

C

FIG. 16 – cont'd
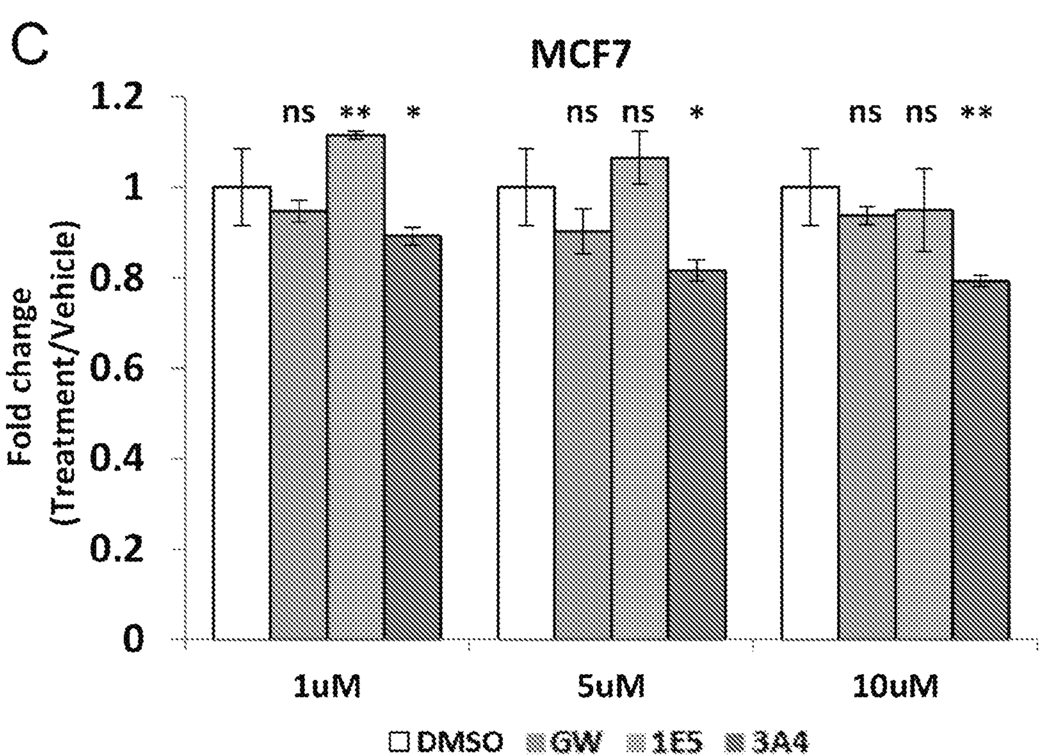
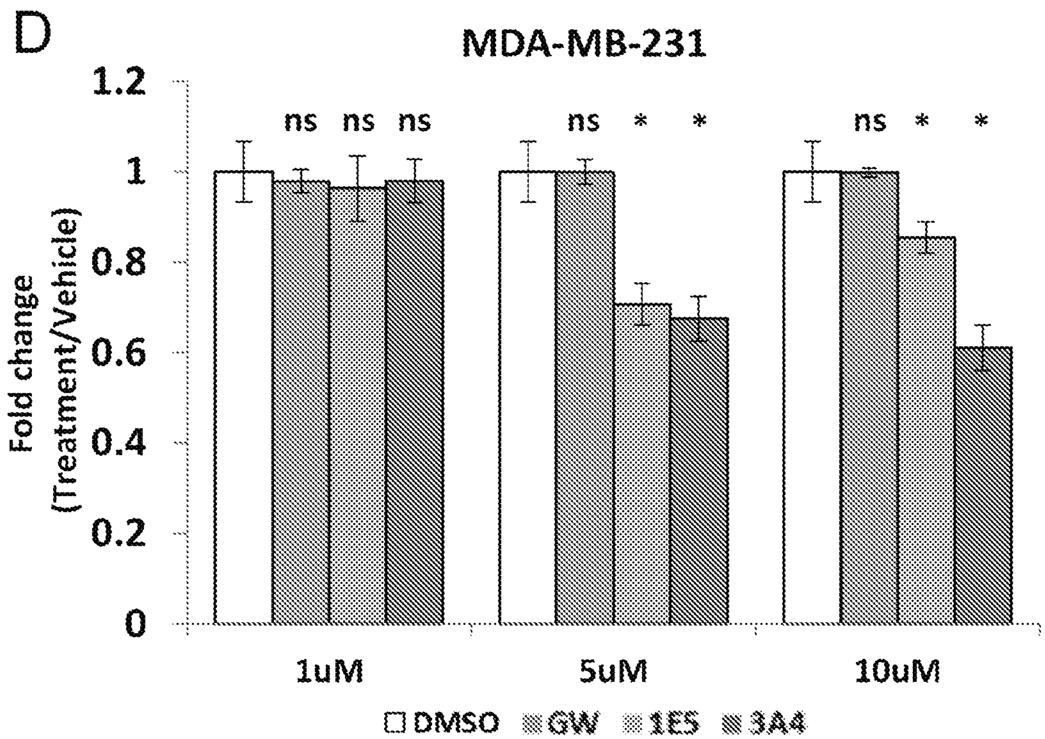

FIG. 20 – cont'd
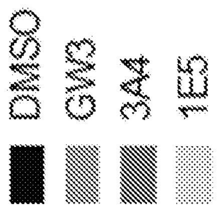
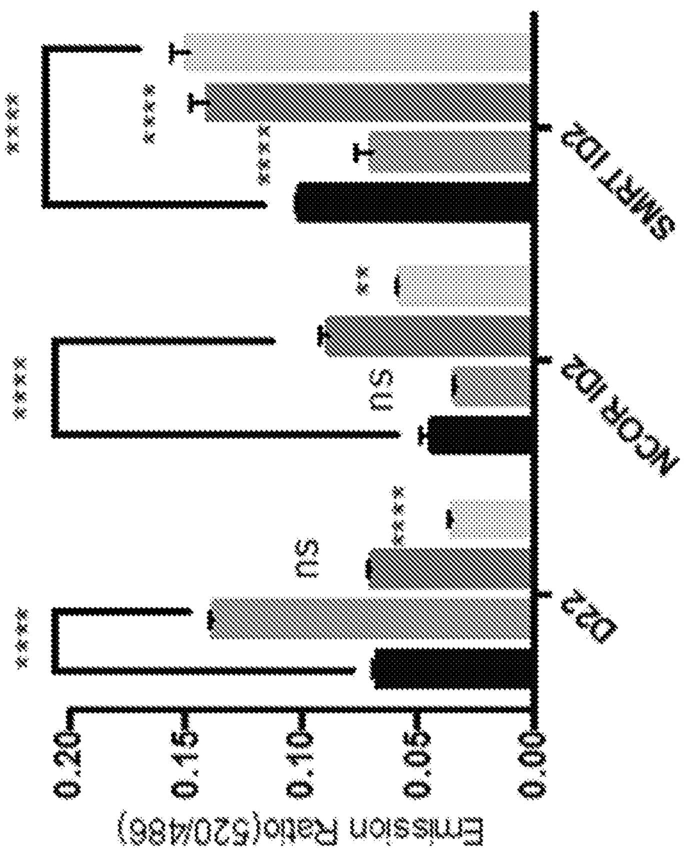
B

BxPC-3
$IC_{50}$ = 5μM
% Cell Viability
BPTES logM
Absorbance 490nm
DMSO
1E5
1E5+BPTES
BPTES
PANC-1
$IC_{50}$= 0.8μM
log [BPTES] M Bx-PC3
RLU
200000
150000
100000
50000
0
DMSO
3A4
1E5
ST
****
ns
****
PANC-1
RLU
40000
30000
20000
10000
0
DMSO
3A4
1E5
ST
**
ns
**
Mia PaCa-2
RLU
25000
20000
15000
10000
5000
0
DMSO
3A4
1E5
ST
**
ns
****

Eicosapentaenoate (EPA; 20:5n3)
Docosapentaenoate (n3 DPA; 22:5n3)
Docosapentaenoate (n6 DPA; 22:5n6)
Scaled Intensity
DMSO
GW3965
1E5
0.0
0.5
1.0
1.5
2.0
2.5
0.2
0.4
0.6
0.8

PANC-1
GW3965
1E5
Log2 mRNA Fold Change
4
2
0
-2
-4
SREBP1c
GPX4
STMN1
RRM2
SAT1
IREB2
Bx-PC3
GW3965
1E5
Log2 mRNA Fold Change
2
1
0
-1
-2
SREBP1c
GPX4
STMN1
RRM2
SAT1
IREB2
Mia PaCa-2
GW3965
1E5
Log2 mRNA Fold Change
6
4
2
0
-2
-4
-6
SREBP1c
GPX4
STMN1
RRM2
SAT1
IREB2

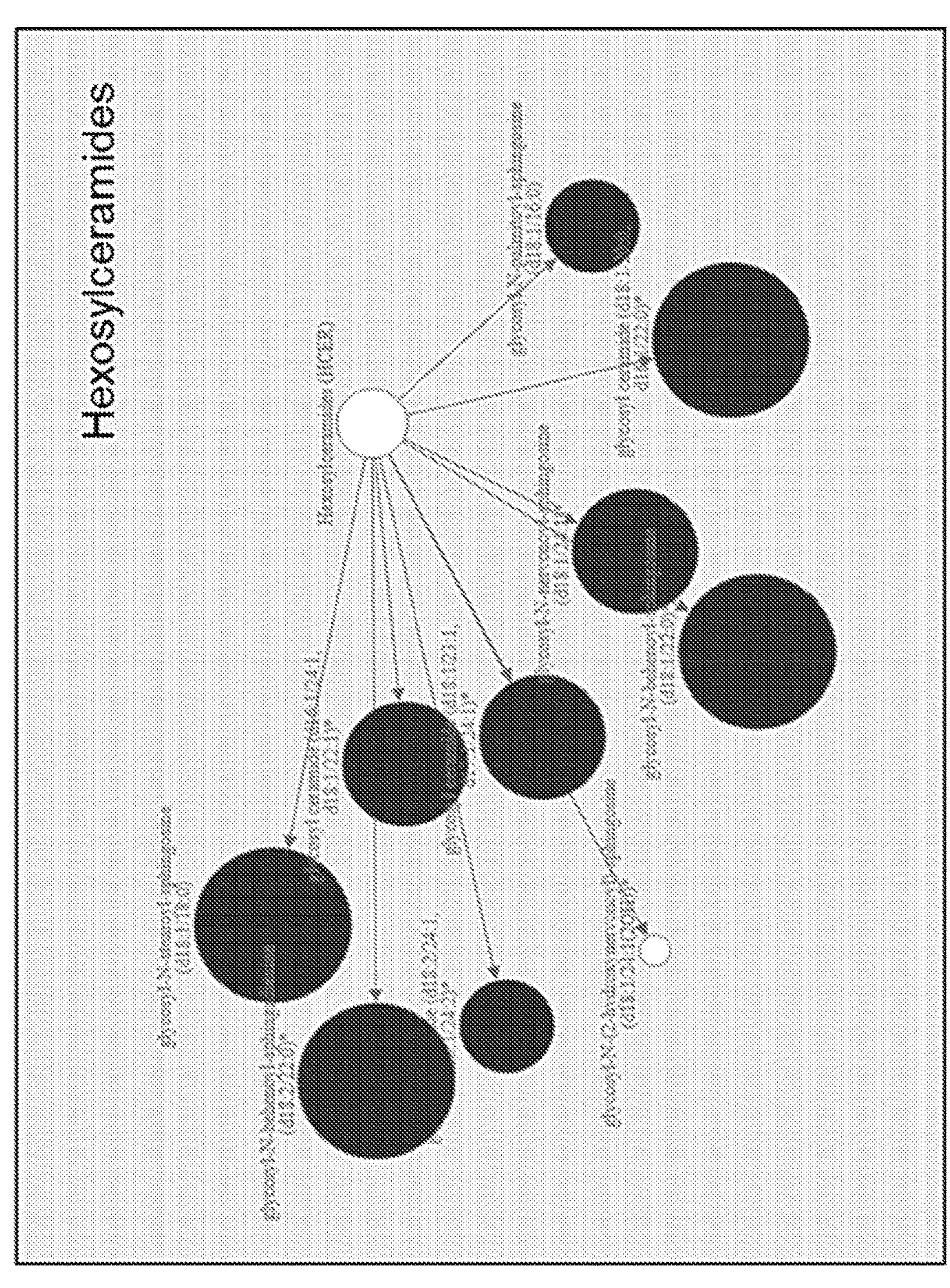
FIG. 31 – cont'd

A
-d/dT Fluorescence (465-610nm)
Temperature
LXRβ LBD
DMSO
KD-39
B
-d/dT Fluorescence (465-610nm)
Temperature
LXRβ LBD
DMSO
1E5
3A4
C
-d/dT Fluorescence (465-610nm)
Temperature
DMSO
GW3965
T090
24(S)-hydroxycholesterol
24(S),25-epoxycholesterol
22(S)-Hydroxycholesterol
22(R)-hydroxycholesterol

SMALL MOLECULE LIVER X RECEPTOR MODULATORS AND USES THEREOF

This application claims priority to U.S. Provisional Patent Application Ser. No. 62/896,068, entitled "Small Molecule Liver X Receptor Modulators and Uses Thereof," filed Sep. 5, 2019, the entire contents of which are incorporated herein by reference.

BACKGROUND

This disclosure pertains to liver X receptor ("LXR") ligands and their derivatives.

Pancreatic ductal adenocarcinoma (PDAC) is the predominant form of pancreatic cancer and is a highly invasive and metastatic disease. PDAC is the third leading cause of cancer deaths in the US, accounting for over 44,000 deaths annually (Cancer Facts & Figures, A C S, 2018). PDAC has the worst prognosis of the major cancers due to difficulties in early detection and a paucity of effective treatment options. Localized tumors represent about 20% of diagnosed cases and are resected using the Whipple procedure. PDAC tumors tend to be desmoplastic, poorly vascularized, and resistant to the standard chemotherapeutic agent gemcitabine, a cytidine nucleoside analog that blocks DNA replication. Recent advances in PDAC treatment include pairing gemcitabine with EGFR inhibitors, such as erlotinib or cetuximab, but this combination only improves median survival by approximately two weeks. A combination regimen of nanoparticle albumin-bound paclitaxel (nab-paclitaxel), a microtubule inhibitor conjugated to albumin for better uptake by tumor cells, improves median survival by two months. Another regimen combining leucovorin, 5-FU, irinotecan, and oxaliplatin (FOLFIRINOX) increases median patient survival by over five months, although with significant toxicity and side effects. More effective target mechanisms and therapeutic strategies are needed and are expected to significantly impact pancreatic cancer morbidity and mortality.

Nearly all PDACs harbor oncogenic mutations in the KRAS gene, but efforts to target mutant KRAS protein as a therapeutic approach in the treatment of PDAC and other mutant KRAS-driven cancers over the past few decades have thus far been unsuccessful. An alternative strategy is to identify and target key regulators of tumor promoting processes, the so called cancer hallmarks, downstream of oncogene activation. Metabolic changes in pancreatic cancer are largely driven by oncogenic mutations in KRAS and include increased glucose uptake and preferential utilization of aerobic glycolysis, known as the Warburg effect, rather than oxidative phosphorylation to meet the energy and biosynthesis demands of cancer cells. Another metabolic shift in cancer cells is the increased demand for lipids which are integral to cell membrane synthesis and also as precursors for signaling molecules in proliferative pathways. While cancer metabolism has emerged as an important cancer hallmark and potential therapeutic target, identifying druggable targets and candidate agents remain a significant challenge.

SUMMARY

The present disclosure relates generally to liver X receptor ("LXR") ligands, derivatives thereof, and their uses in cancer therapeutics.

Nuclear receptors (NRs) are a family of related ligand-dependent transcription factors which control gene expression through transcriptional and epigenetic regulatory mechanisms. NRs function in normal development and physiology processes, including those involved in cancer hallmarks. For example, estrogen receptor α (ERα) is involved in normal and cancerous mammary cell biology and is targeted directly by small molecule anti-estrogens (fulvestrant) and selective estrogen receptor modulators (SERMs; tamoxifen, raloxifene) or indirectly by aromatase inhibitors (anastrozole, letrozole, exemestane) which block the production of estrogen. Androgen receptor (AR) is likewise targeted in the treatment of prostate cancer. Liver X receptors (LXRs) are NRs which function in the regulation of genes that are involved in cholesterol, glucose, and lipid metabolism and inflammatory responses. LXR activity can be modulated by a variety of endogenous ligands, phytochemicals, and synthetic compounds, a number of which have been developed for the treatment of atherosclerosis and metabolic diseases and have undergone extensive functional, pharmacological, and toxicological characterization and clinical trial. Studies of LXR ligands in cancer cell lines revealed their antiproliferative effects in a variety of cancer types, including pancreatic cancer. LXR ligands can target both tumor and stromal cells and may regulate recruitment of immune modulatory cells. Given their known target genes and metabolic functions, a proposed mechanism of action of LXRs and their ligands in cancer cells is through their impact on cancer metabolism. LXRs have been shown to control the expression of key regulators of glucose and lipid metabolism, including sterol regulatory element binding transcription factor 1 (SREBF1), carbohydrate responsive element-binding protein (ChREBP/MLXIPL), glucokinase (GCK), fatty acid synthase (FASN), and stearoyl-CoA desaturase (SCD). These LXR target genes function in cancer-related metabolic pathways, such as those involved in the glycolysis and lipogenesis. The highly druggable LXRs are involved in the regulation of cancer-specific metabolic gene networks and pathways in pancreatic and other types of cancers.

The present disclosure relates to targeting oncogene-driven metabolic reprogramming and other cancer hallmarks via LXRs, highly druggable NRs, as a therapeutic approach in pancreatic cancer. Current synthetic ligands used in LXR research were originally developed for treating atherosclerosis and have adverse effects on circulating and liver triglyceride levels. Newly discovered inverse agonists and degraders with distinct chemical structures from current synthetic agonists which modulate LXR activity and with more potent anti-tumor activity than current synthetic agonists which modulate LXR activity are described herein for use in the treatment of advanced pancreatic cancer. These novel ligands function as inverse agonists and degraders and will not elicit the adverse effects observed in current synthetic agonists. Derivatives of the two lead inverse agonists have been synthesized for functional characterization of LXRs and their ligands in pancreatic cancers and other malignancies which currently lack effective treatment options.

Existing treatments used in the treatment of pancreatic cancer rely on chemotherapeutic agents which indiscriminately target all dividing cells in the body. Therefore, chemotherapies have significant adverse effects with toxicity and also with the development of resistance by cancer cells over time. Novel small molecule liver X receptor modulators exhibit activity against tumor cells and less or no activity against dividing non-malignant cells, target the liver X receptor and disrupt key metabolic pathways preferred by cancer cells, and activate a newly discovered cell death mechanism which is distinct from the cell death induced by chemotherapeutic agents. These compounds can thus be a less toxic alternative to chemotherapy and can be used in combination with chemotherapy to increase efficacy and decrease the likelihood of cancer cells developing resistance. Moreover, they can be used as second-line treatments when chemotherapies are ineffective or if cancer cells develop resistance over time.

BRIEF DESCRIPTION OF THE DRAWINGS

FIG. 6(G-H) show Western blot analysis of expression of (G) LXRβ and (H) LXRα in pancreatic ductal adenocarcinoma (PDAC) cells, with expression of LXRβ only in cancer cell lines.

DETAILED DESCRIPTION OF PREFERRED EMBODIMENTS

The present disclosure relates to Liver X receptor (LXR) ligands, derivatives thereof, and their uses.

Synthetic LXR agonists (GW3965 and T0901317) described herein were originally developed to treat heart disease but failed in pre-clinical testing due to increased circulating and liver triglyceride levels. Moreover, heart disease-specific molecular and functional endpoints were used in the characterization and development of these compounds. There are currently no LXR ligands which have been developed specifically in cancer models for cancer research and therapy. To identify LXR ligands specifically for cancer research and therapeutics, structure-based docking simulation of candidate compounds into the ligand binding pocket of LXRβ was conducted to virtually screen existing drug-like compound libraries and evaluation of promising hits and their derivatives. 560 putative LXRβ ligands were identified. This focused library was further evaluated for effects on the growth of three PDAC cell lines. Two preferred embodiments of ligands with greater anti-proliferative activity than the synthetic agonist GW3965 were identified, as shown below.

1E5

3A4

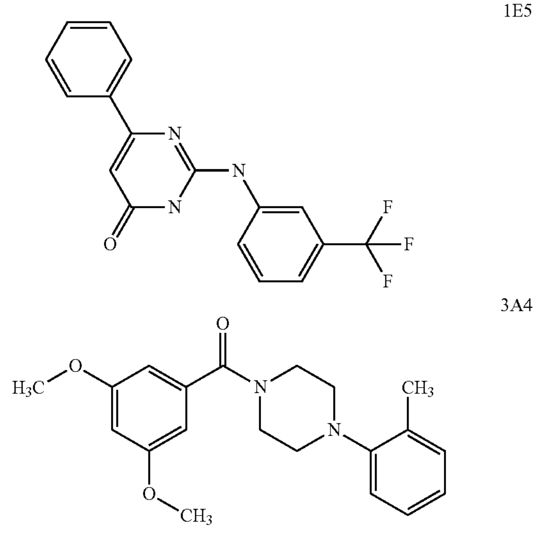

The two preferred embodiments of LXR ligands are the following: Compound GAC0001E5 (1E5)=6-phenyl-2-{[3-(trifluoromethyl)phenyl]amino}-3,4-dihydropyrimidin-4-one, and Compound GAC0003A4 (3A4)=1-(3,5-dimethoxybenzoyl)-4-(2-methylphenyl)piperazine.

Figure 1:
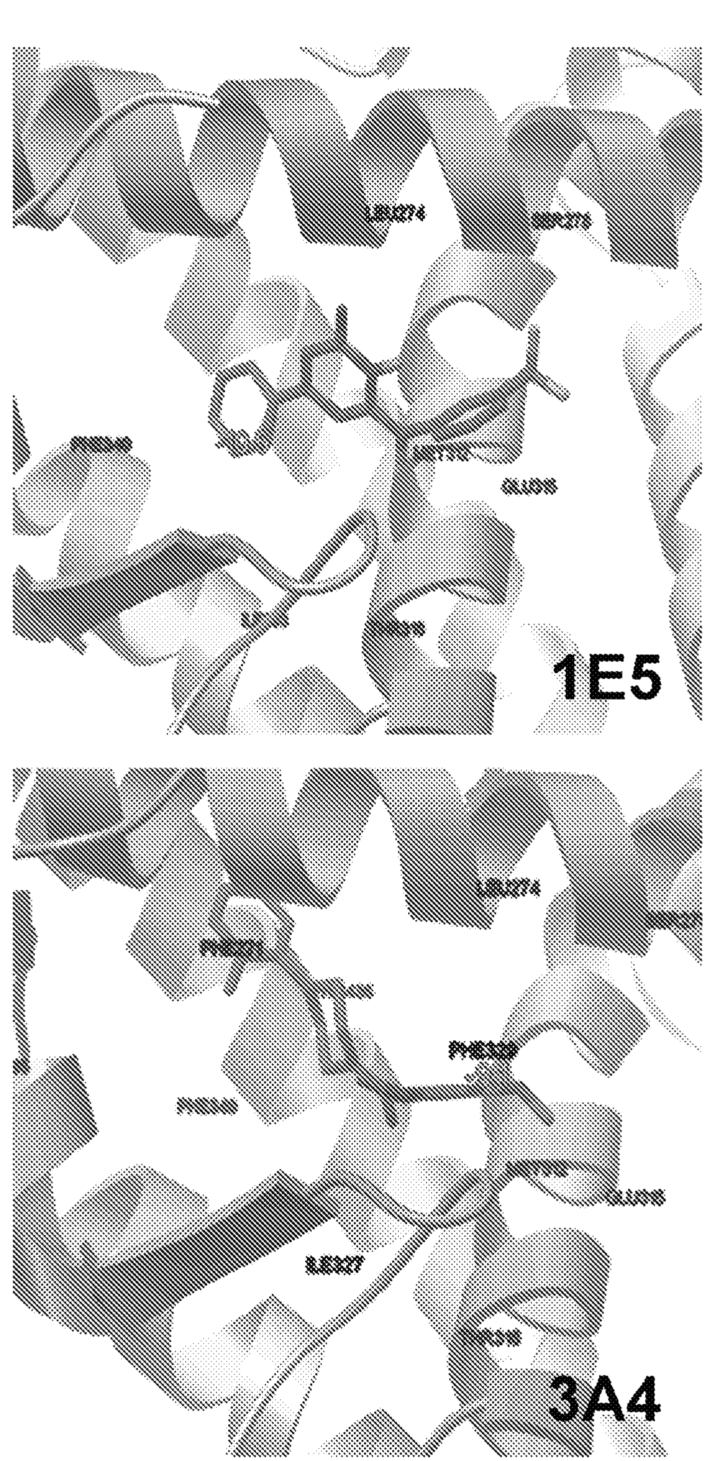
FIG. 1 shows three-dimensional structures of two exemplary LXR ligands within the ligand-binding domain of LXRβ.

FIG. 1 illustrates the three-dimensional structures of the two exemplary LXR ligands within the ligand-binding domain of LXRβ.

Figure 2:
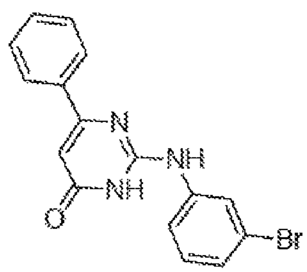
FIG. 2 shows chemical structures of derivatives of exemplary LXR ligand 1E5 in accordance with preferred embodiments described herein.
Figure 2:
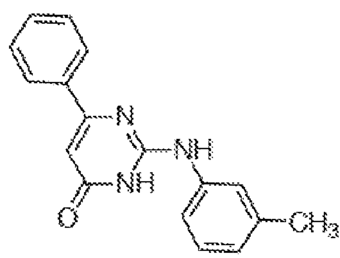
Figure 2:
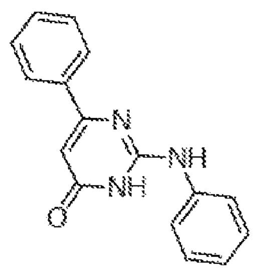
Figure 2:
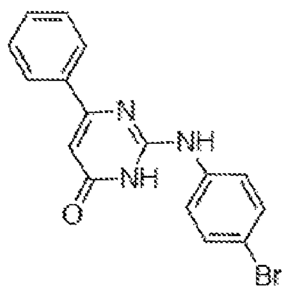
Figure 2:
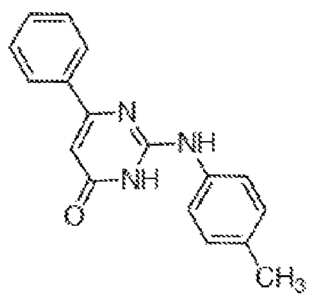
Figure 2:
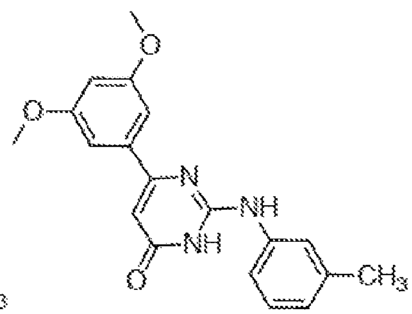
Figure 2:
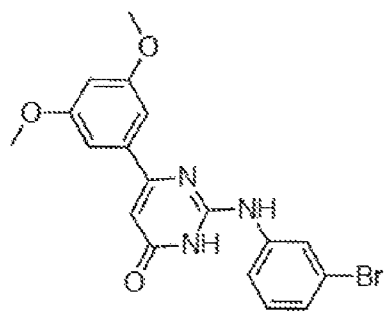
Figure 2:
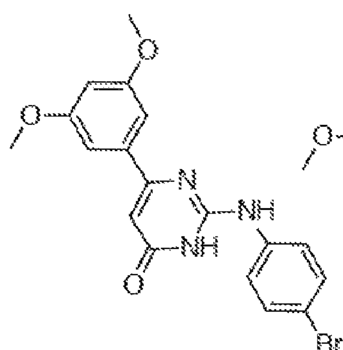
Figure 2:
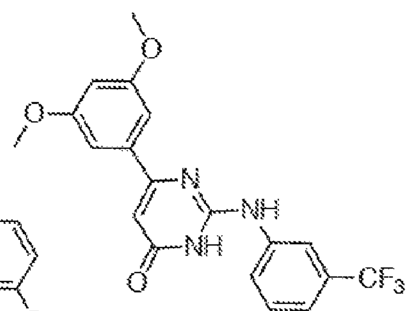
Figure 3:
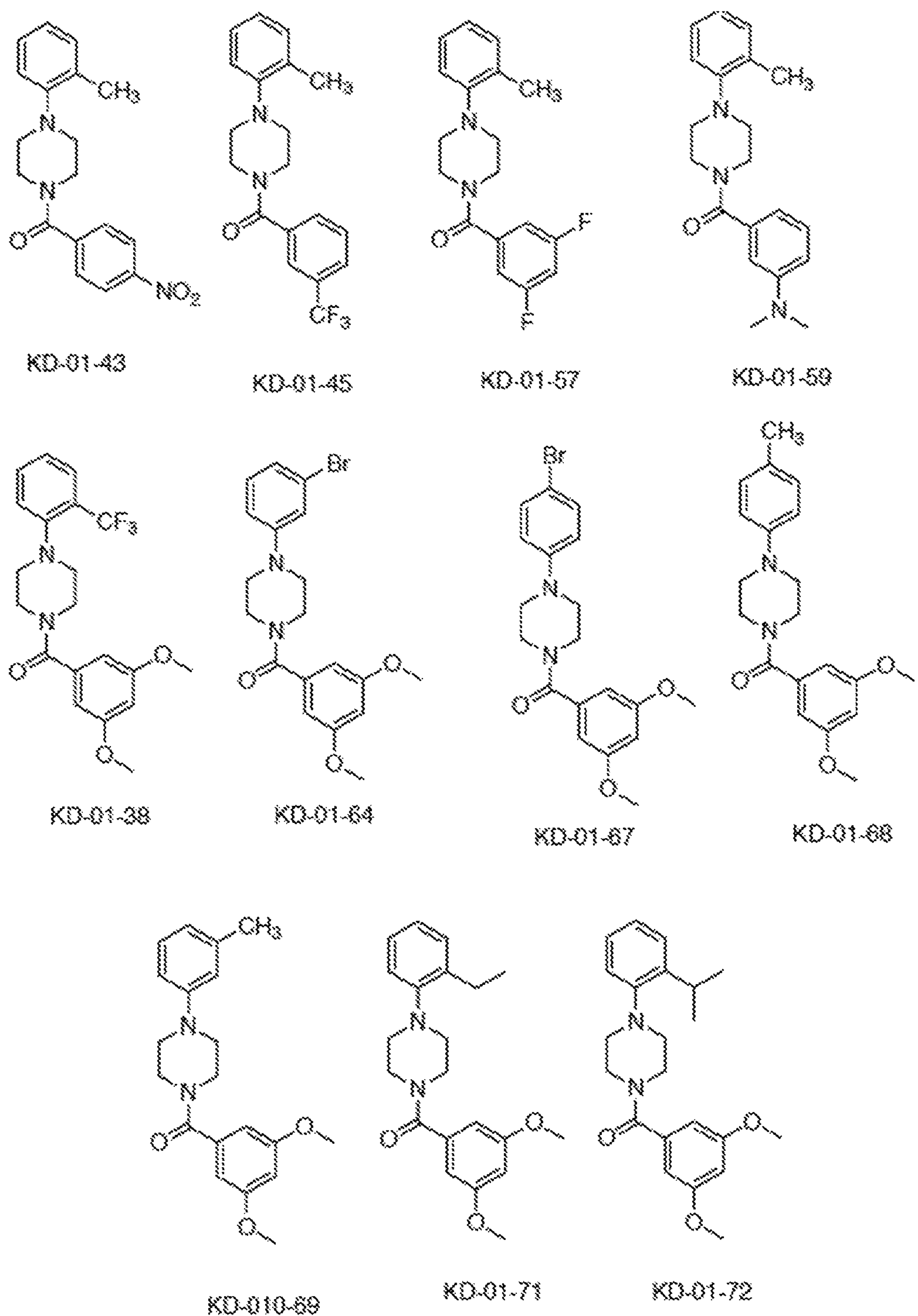
FIG. 3 shows chemical structures of derivatives of exemplary LXR ligand 3A4 in accordance with preferred embodiments described herein.
Figure 4:
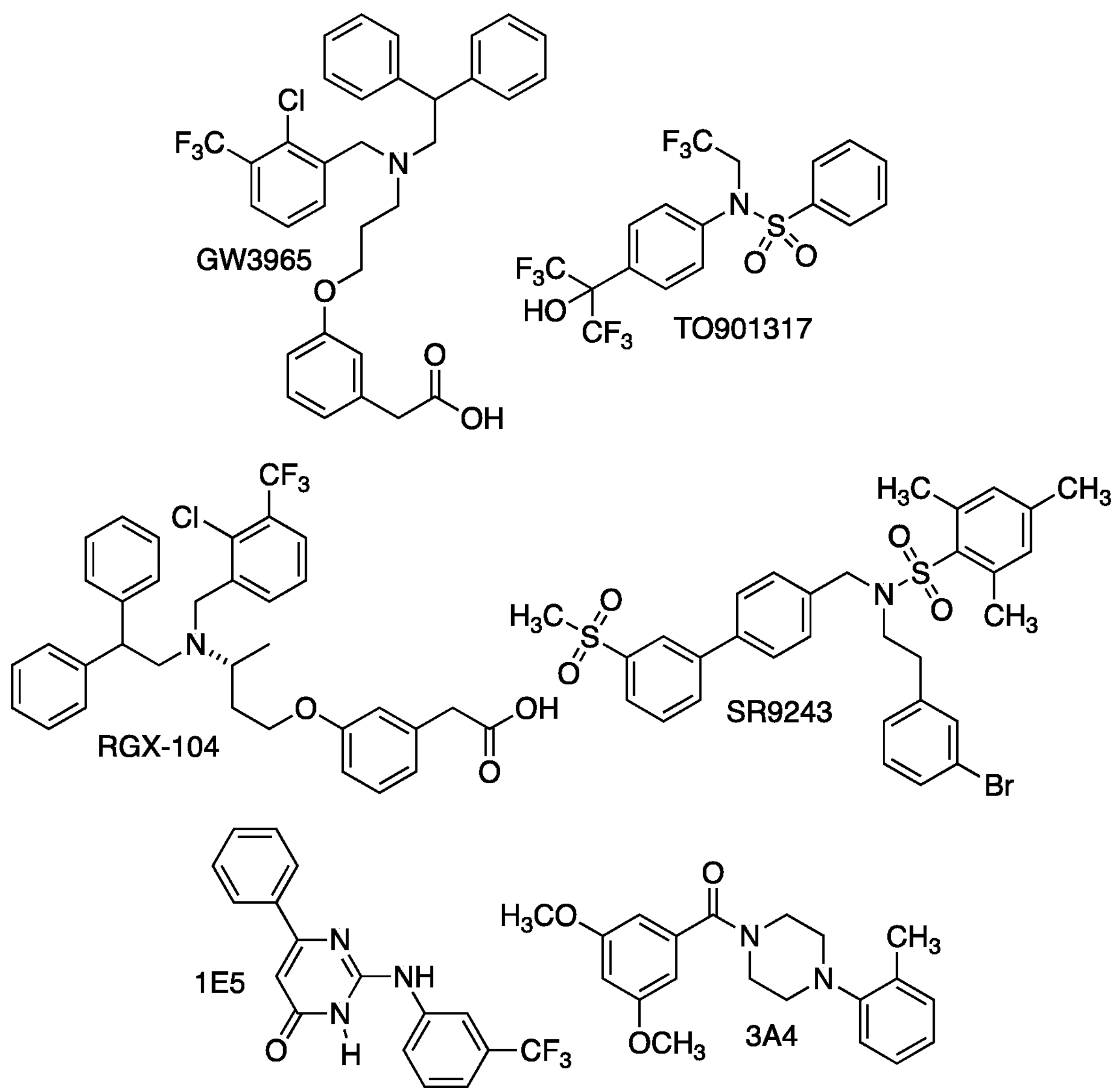
FIG. 4 shows a comparison of the core structures of exemplary LXR ligands 1E5 and 3A4 with other known structures.

Additional LXR ligands were prepared based on the chemical structure of Compounds 1E5 and 3A4. Chemical structures of preferred embodiments of 1E5 derivatives are shown in FIG. 2, and chemical structures of preferred embodiments of 3A4 derivatives are shown in FIG. 3. Preferred embodiments described herein include LXR ligands 1E5 and 3A4 and derivatives thereof. The core structures of 1E5 and 3A4 are different from the molecules reported by others. FIG. 4 shows a comparison of the core structures of 1E5 and 3A4 with known compounds reported by others. The known compounds GW3965, TO901317, RGX-104 and SR9243 all consist of a linear core with aromatic groups attached. 1E5 and 3A4, and the derivatives that are being developed from these leads, have cyclic cores, a pyrimidinone and a piperazine, which provide an opportunity to display the pharmacophore groups in a more controlled orientation. This in turn should result in better selectivity for the target.

Additional preferred embodiments relate to the use of LXR ligands 1E5 and 3A4 and derivatives thereof in treating cancer, and in reducing or otherwise inhibiting the growth of tumors caused by cancer cells, including pancreatic cancer cells and cells from other recalcitrant cancers such as triple-negative breast cancer.

Additional preferred embodiments include pharmaceutical compositions including a therapeutically effective amount of a LXR ligand or derivative thereof as described herein and a pharmaceutically acceptable excipient, adjuvant, carrier, buffer or stabilizer. A "therapeutically effective amount" is to be understood as an amount of an exemplary compound that is sufficient to show inhibitory effects on tubulin polymerization, vascularization, metastasis, survival and/or proliferation of tumors or cancerous cells. The actual amount, rate and time-course of administration will depend on the nature and severity of the disease being treated. Prescription of treatment is within the responsibility of general practitioners and other medical doctors. The pharmaceutically acceptable excipient, adjuvant, carrier, buffer or stabiliser should be non-toxic and should not interfere with the efficacy of the active ingredient. The precise nature of the carrier or other material will depend on the route of administration, which may be oral, or by injection, such as cutaneous, subcutaneous, or intravenous injection, or by dry powder inhaler.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such as gelatin. For intravenous, cutaneous or subcutaneous injection, the active ingredient will be in the form of a parenterally acceptable aqueous solution which is pyrogen-free and has a suitable pH, isotonicity and stability. Those of relevant skill in the art are well able to prepare suitable solutions using, for example, isotonic vehicles such as sodium chloride solution, Ringer's solution, or lactated Ringer's solution. Preservatives, stabilizers, buffers, antioxidants and/or other additives may be included as required.

In another aspect, there is provided the use in the manufacture of a medicament of a therapeutically effective amount of a LXR ligand or derivative thereof as described herein for administration to a subject.

The term "pharmacologically acceptable salt" used throughout the specification is to be taken as meaning any acid or base derived salt formed from hydrochloric, sulfuric, phosphoric, acetic, citric, oxalic, malonic, salicylic, malic, fumaric, succinic, ascorbic, maleic, methanesulfonic, isoethonic acids and the like, and potassium carbonate, sodium or potassium hydroxide, ammonia, triethylamine, triethanolamine and the like.

The term "prodrug" means a pharmacological substance that is administered in an inactive, or significantly less active, form. Once administered, the prodrug is metabolised in vivo into an active metabolite.

The term "therapeutically effective amount" means a nontoxic but sufficient amount of the drug to provide the desired therapeutic effect. The amount that is "effective" will vary from subject to subject, depending on the age and general condition of the individual, the particular concentration and composition being administered, and the like. Thus, it is not always possible to specify an exact effective amount. However, an appropriate effective amount in any individual case may be determined by one of ordinary skill in the art using routine experimentation. Furthermore, the effective amount is the concentration that is within a range sufficient to permit ready application of the formulation so as to deliver an amount of the drug that is within a therapeutically effective range.

Example 1

Synthesis of Exemplary 3A4 Derivative, KD-01-39

Figure 5:
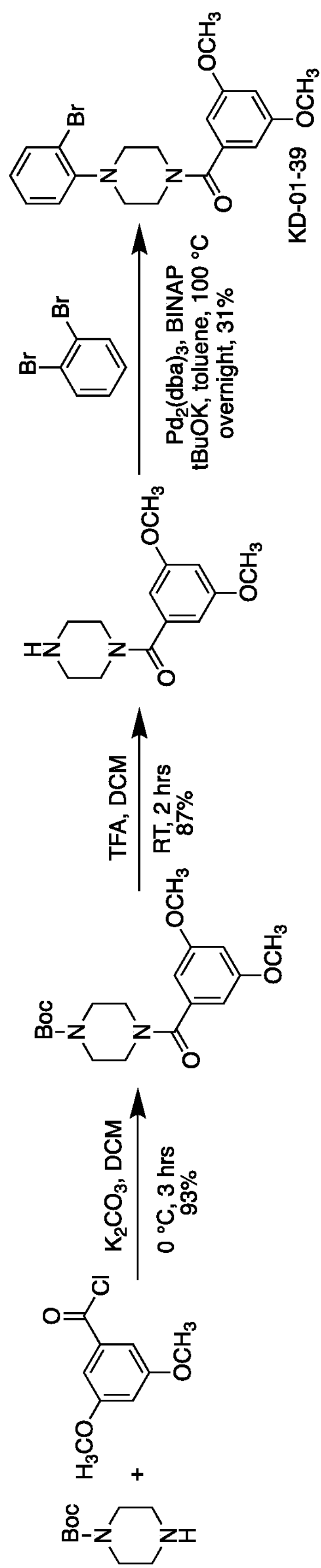
FIG. 5 shows a general synthetic scheme for an exemplary 3A4 derivative, KD-01-39.

The structure and synthesis of a 3A4 derivative, KD-01-39, have never been described previously. In the chemical structure of KD-01-39, the methylbenzene ring in the parental 3A4 compound has been substituted with a bromobenzene. A general scheme for the synthesis of KD-01-39 is shown in FIG. 5. The synthesis of KD-01-39 was carried out in the following manner.

(1) Synthesis of compound 1, shown below:

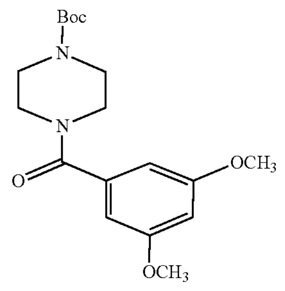 [SMILES: COc1cc(OC)cc(C(=O)N2CCN(C(=O)OC(C)(C)C)CC2)c1]

To a stirred solution of 1-Boc-piperazine (1.2 g, 6.48 mmol, 1.3 equiv.) in 12 mL of anhydrous $CH_2Cl_2$ was added $K_2CO_3$ (689 mg, 4.99 mmol, 1 equiv.). The mixture was stirred at 0° C. for 10 min under nitrogen. Then 3,5-dimethoxy benzoyl chloride (1.0 g, 4.99 mmol, 1 equiv.) was added and the reaction was run for 3 hours at 0° C. After completion, mixture was concentrated by evaporating the solvent. Then water was added and the mixture was extracted with ethyl acetate. The organic phases were combined and washed with brine, dried over anhydrous $MgSO_4$, filtered and concentrated to yield the crude product. The product was purified by column chromatography on silica gel using 5% MeOH in $CH_2Cl_2$. 1.60 g of white solid was obtained, 93% yield.

$^1H$ NMR (500 MHz, methanol-$d_4$) δ 6.57 (t, J=2.3 Hz, 1H), 6.54 (d, J=2.3 Hz, 2H), 3.79 (s, 6H), 3.70 (s, 2H), 3.52 (s, 2H), 3.41 (s, 4H), 1.46 (s, 9H).

$^{13}C$ NMR (126 MHz, acetone-$d_6$) δ 205.50, 169.23, 161.03, 154.23, 138.43, 104.89, 101.26, 79.26, 55.11, 47.19, 44.15, 43.28, 41.76, 27.86.

(2) Synthesis of compound 2, shown below:

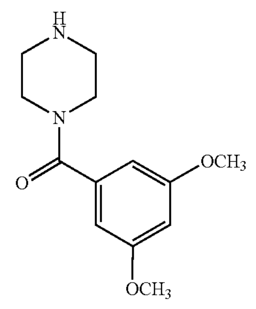 [SMILES: COc1cc(OC)cc(C(=O)N2CCNCC2)c1]

To a stirred solution of compound 1 (1.6 g, 4.66 mmol, 1 equiv.) in 10 mL of $CH_2Cl_2$ was added 14 mL of TFA at 0° C. The resulting mixture was allowed to warm to room temperature over 2 hours. After completion, 6N NaOH was added dropwise until the pH of the mixture reach ~10 and then extracted with $CH_2Cl_2$. The organic phases were combined and washed with brine, dried over anhydrous $MgSO_4$, filtered and concentrated to yield the crude product. The product was purified by column chromatography on silica gel using 20% MeOH in $CH_2Cl_2$ 1.01 g of white solid was obtained, 87% yield.

$^1H$ NMR (400 MHz, methanol-$d_4$) δ 6.56 (t, J=2.3 Hz, 1H), 6.52 (d, J=2.3 Hz, 2H), 3.79 (s, 6H), 3.70 (s, 2H), 3.39 (s, 2H), 2.88 (s, 2H), 2.75 (s, 2H).

$^{13}C$ NMR (126 MHz, acetone-$d_6$) δ 169.6, 161.5, 139.4, 105.3, 101.4, 55.6, 49.2, 46.7, 46.3, 43.5.

(3) Synthesis of KD-01-39, shown below:

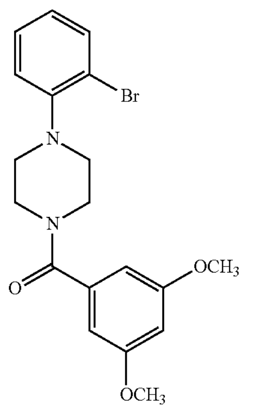 [SMILES: COc1cc(OC)cc(C(=O)N2CCN(c3ccccc3Br)CC2)c1]

An oven-dried flask was charged with 1,2-dibromobenzene (0.65 mL, 5.39 mmol, 1.2 equiv.), $Pd_2(dba)_3$ (247 mg, 0.27 mmol, 0.06 equiv.), BINAP (280 mg, 0.45 mmol, 0.1 equiv.), tBuOK (1.01 mg, 8.99 mmol, 2 equiv.) and 18 mL of toluene. The mixture was stirred at room temperature for 20 min. Then compound 2 (1.13 g, 4.49 mmol, 1 equiv.) was added and the reaction was heated to 100° C. and run overnight. Upon completion, crude mixture was filtered through celite and solvent was removed under vacuum. Then crude was extracted with ethyl acetate. The organic phases were combined and washed with brine, dried over anhydrous $MgSO_4$, filtered and concentrated to yield the crude product. The product was purified by column chromatography on silica gel using 40% EtOAc in hexane. 564 mg of yellow oil was obtained, 31% yield.

$^1H$ NMR (600 MHz, chloroform-d) δ 7.56 (d, J=9.3 Hz, 1H), 7.27 (t, J=8.4 Hz, 1H), 7.02 (d, J=8.0 Hz, 1H), 6.94 (t, J=7.6 Hz, 1H), 6.56 (d, J=2.4 Hz, 2H), 6.50 (t, J=2.3 Hz, 1H), 3.95 (s, 2H), 3.80 (s, 6H), 3.61 (s, 2H), 3.10 (s, 2H), 2.96 (s, 2H).

$^{13}C$ NMR (151 MHz, chloroform-d) δ 170.1, 160.9, 149.9, 137.6, 133.9, 128.4, 124.9, 121.1, 120.0, 104.8, 101.6, 55.5, 52.2, 51.4, 48.0, 42.3.

Example 2

Expression of LXR Isoforms in Pancreatic Cancer Cells and Clinical Samples

Figure 6:
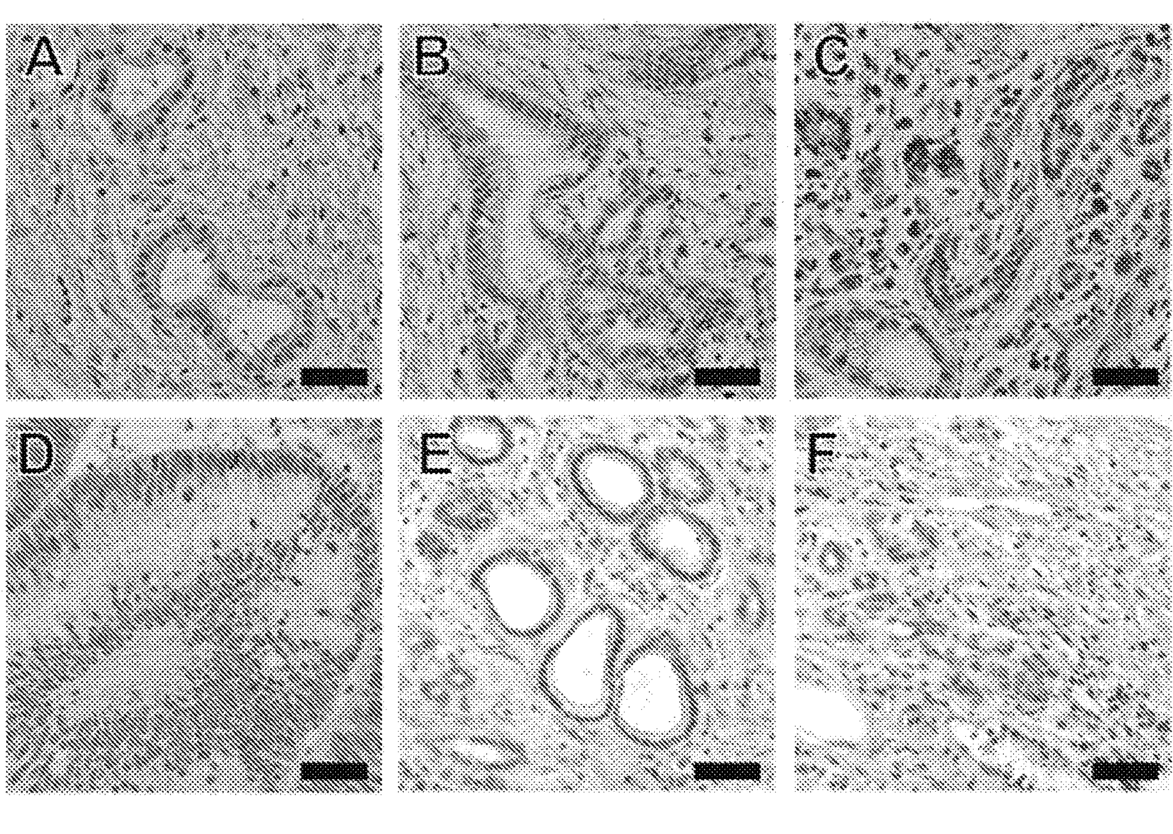
FIG. 6(A-F) show results of immunohistochemical staining of LXRβ in (A-C) pancreatic cancer cell samples, with no staining in (D) adenoma or (E-F) normal pancreatic tissues.
Figure 6:
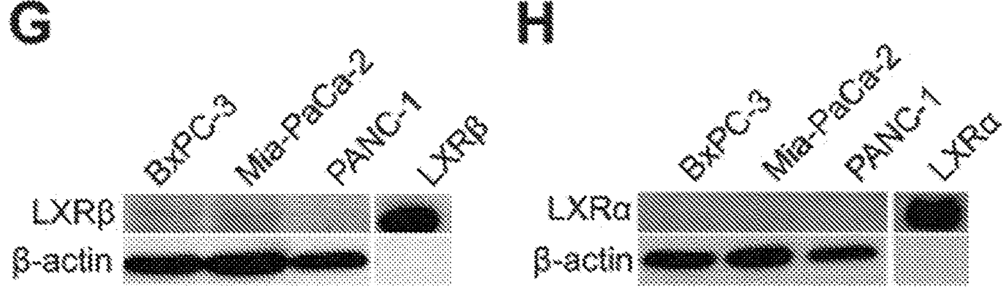

Two LXRs, LXRα and LXRβ, mediate the effects of natural and synthetic ligands in target tissues. LXRα and LXRβ expression were examined in human pancreatic tumor samples and PDAC cell lines. FIG. 6 shows that LXRβ is the main LXR isoform expressed in pancreatic cancer samples and in three pancreatic adenocarcinoma cell lines. FIG. 6A shows that immunohistochemical staining of LXRβ in human samples demonstrated nuclear immunoreactivity in the nuclei of normal pancreatic ductal epithelial cells. FIGS. 6B and 6C show that LXRβ positive immunoreactivity was evident in both the cytosol and the nuclei of neoplastic cells of patients with pancreatic adenocarcinoma (PDAC). The nuclear and cytoplasmic LXRβ detected in PDAC samples indicated possible altered localization of LXRβ in these cancerous samples. FIG. 6D shows that comparatively, LXRβ expression was barely detectable in a pancreatic adenoma clinical sample. Contrary to what was observed with LXRβ, FIG. 6E shows that LXRα immunoreactivity was not detected in normal ducts or, as shown in FIG. 6F, in PDAC samples. These results suggest that LXRβ is the main isoform present in pancreatic ductal epithelial cells and its expression is evident in PDAC. For functional studies, BxPC-3, MIA-PaCa-2, and PANC-1 cell lines were chosen as representative cell-based models of PDAC due to their differences in invasive, proliferative, and angiogenic potentials. Western results shown in FIG. 6G indicate that LXRβ was detected in BxPC-3 and MIA-PaCa-2 and PANC-1 cells, although expression levels were the lowest in the PANC-1 cells. FIG. 6H shows that consistent with observations in clinical samples, LXRα was not detected in PDAC cell lines.

Figure 7:
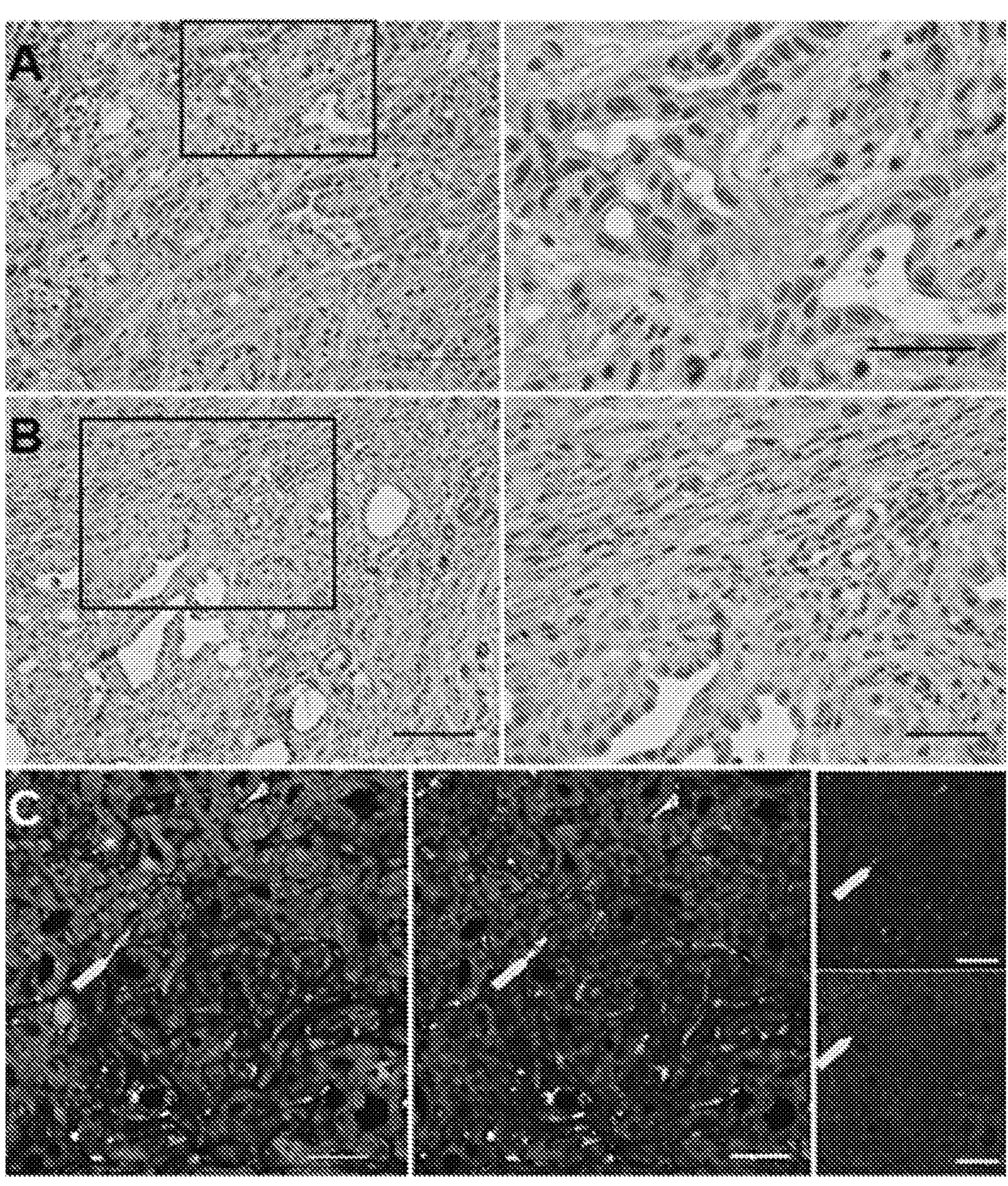
FIG. 7(A-C) show results of immunohistochemical staining of LXRβ in cells of a transgenic mouse model of pancreatic cancer.

Furthermore, LXRβ expression was detected in tumor and stromal cells in a genetically engineered mouse model of PDAC. FIG. 7A and FIG. 7B show that LXRβ is expressed in epithelial and stromal cells (brown) in a transgenic mouse model of pancreatic cancer Immunohistochemical staining for LXRβ was done in KCiHnf1b;p53Tg/Tg transgenic mice. Brown staining indicates positive reactivity for LXRβ. FIG. 7C shows immunofluorescent staining for LXRβ, Cytokeratin 19, and smooth muscle actin in transgenic mouse tumor. Staining present in both CK19+ tumor cells and SMA+ myofibroblasts indicates positive reactivity for LXRβ in tumor and stromal cells.

Example 3

Anti-Proliferative Effects of LXR Ligands.

Figure 8:
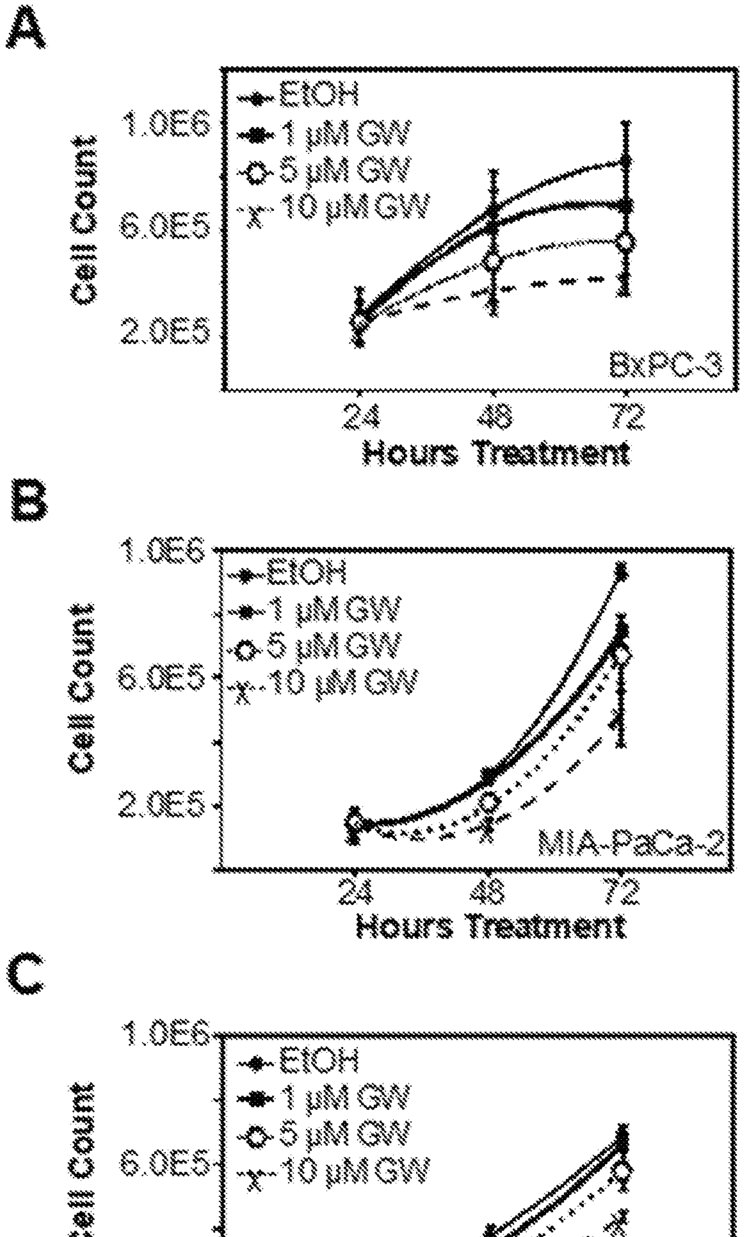
FIG. 8 shows cell proliferation by cell counting in (A) Bx-PC3, (B) Mia PaCa-2, and (C) PANC-1 pancreatic cancer cell lines following treatment with increasing concentrations of synthetic LXR agonists GW3965, with similar results obtained using (D) MTS and (E-F) colony formation assays.

To determine the effects of LXR ligands on PDAC cell proliferation, cells were treated with synthetic LXR agonist GW3965 and live cells were quantified using trypan blue exclusion assays. FIG. 8 shows that LXR agonists block cell proliferation and colony-formation in pancreatic cancer cells. FIGS. 8A, 8B, and 8C show dose-dependent decreases in cell proliferation in BxPC-3, Mia-PaCa-2, and PANC-1, respectively upon treatment with increasing GW3965 concentrations. Thus, cell proliferation was significantly inhibited by GW3965 treatment. Titration curve experiments showed a dose-dependent inhibition of cell proliferation in all three cell lines. EC50 calculations indicated that BxPC-3 and Mia-PaCa-2 cells were more sensitive to ligand treatment than PANC-1 cells. Additional studies using tetrazolium salt reduction (WST) assays further confirmed that GW3965 suppressed the growth of PDAC cell lines in a dose-dependent manner FIG. 8D shows results of an MTS assay, as separate measure of overall cell metabolic rate and indirect measurement of cell proliferation, demonstrating a dose-dependent drop in overall metabolism in cells treated with increasing concentrations of GW3965. Clonogenic assays were also employed to evaluate the effects of long-term LXR ligand treatment on cell proliferation and colony formation. Activation of LXRs using GW3965 strongly inhibited colony formation in each cell line. FIG. 8E shows colony-formation ability in all three cell lines was blocked by GW3965 treatment. FIG. 8F shows quantification of colony formation of GW3965 treated cells relative to vehicle-treated controls. These findings indicate that LXRs are involved in PDAC cell proliferation and targeting LXRs with ligands perturb their normal functions in cell proliferation.

Example 4

Anti-Tumor Effects of LXR Ligand in an Orthotopic Xenograft Mouse Model.

Figure 9:
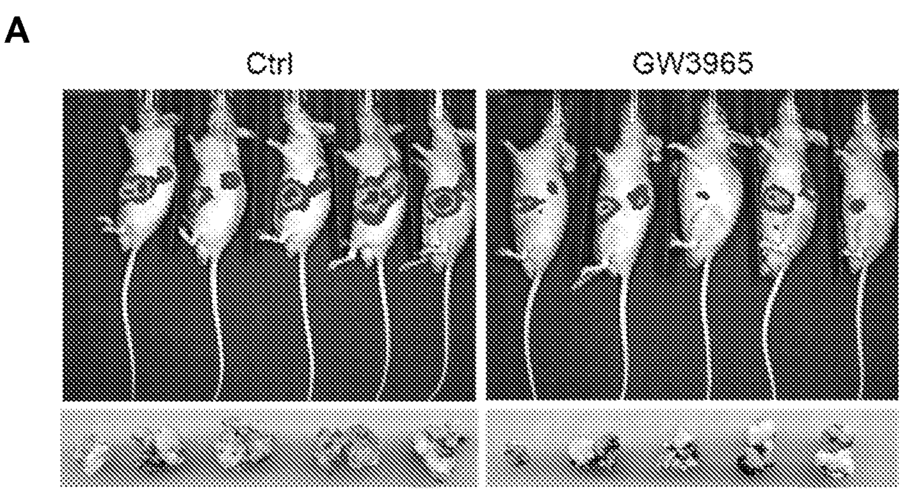
FIG. 9 shows (A) images of tumors in control and GW3965 ligand-treated live animals and following excision and (B) quantification of luciferase signals from tumor cells treated with increasing concentrations of GW3965, with the (C) size and (D) weight of excised tumors in control and treated animals also displayed and indicating significant differences.

Data from studies using cultured cancer cell lines indicate that LXR agonists have anti-proliferative effects on PDAC cells by disrupting cell cycle progression and expression of key regulatory proteins and growth pathways. To determine the effects of ligands in vivo using a live imaging system, BxPC-3 cells engineered with two copies of the firefly luciferase gene (BxPC-3-luc2) were obtained from a commercial source (Perkin Elmer) and then validated for luciferase expression and response to GW3965 treatment in culture. FIG. 9 shows the effects of LXR ligands on tumor formation in an orthotopic xenograft mouse model of pancreatic cancer. NCr athymic nude mice (n=5 per treatment group) were orthotopically injected with BxPC-3-luc2 cells and then gavaged daily with GW3965 dissolved in 0.5% methylcellulose or vehicle only. Animals were anesthetized, injected with luciferin, and imaged weekly to monitor and quantify tumor growth. FIG. 9A shows tumors in control and ligand-treated (vehicle, 40 mg/kg or 80 mg/kg GW 3965, n=5 per group) live animals imaged using the IVIS system for detecting luciferase activity in tumor cells. Experiments were terminated after two weeks due to the morbidity associated with the tumor burden in test animals. FIG. 9B shows luciferase signals from tumor cells monitored weekly and plotted for comparison. Treatments with ligands (40 mg/kg and 80 mg/kg) reduced tumor growth at one- and two-weeks following the start of the treatment regimen. FIG. 9C shows tumors resected from mice for visual inspection. Post-mortem examination of tumors showed significant differences in tumor size. FIG. 9D shows tumor weight determined post-mortem, with statistical tests performed to assess differences between control and treated animals. FIG. 9E shows tumor size measured and analyzed as absorbance values. Statistically significant differences in additive effects as compared to single compound treatments are denoted with asterisks. These results confirmed the bioavailability and low toxicity of GW3965 following ingestion, as it has been shown in other pre-clinical studies of the compound, and provided the first evidence of its anti-tumor activity at the organ site of interest.

Example 5

LXR Ligand Characterization

Figure 10:
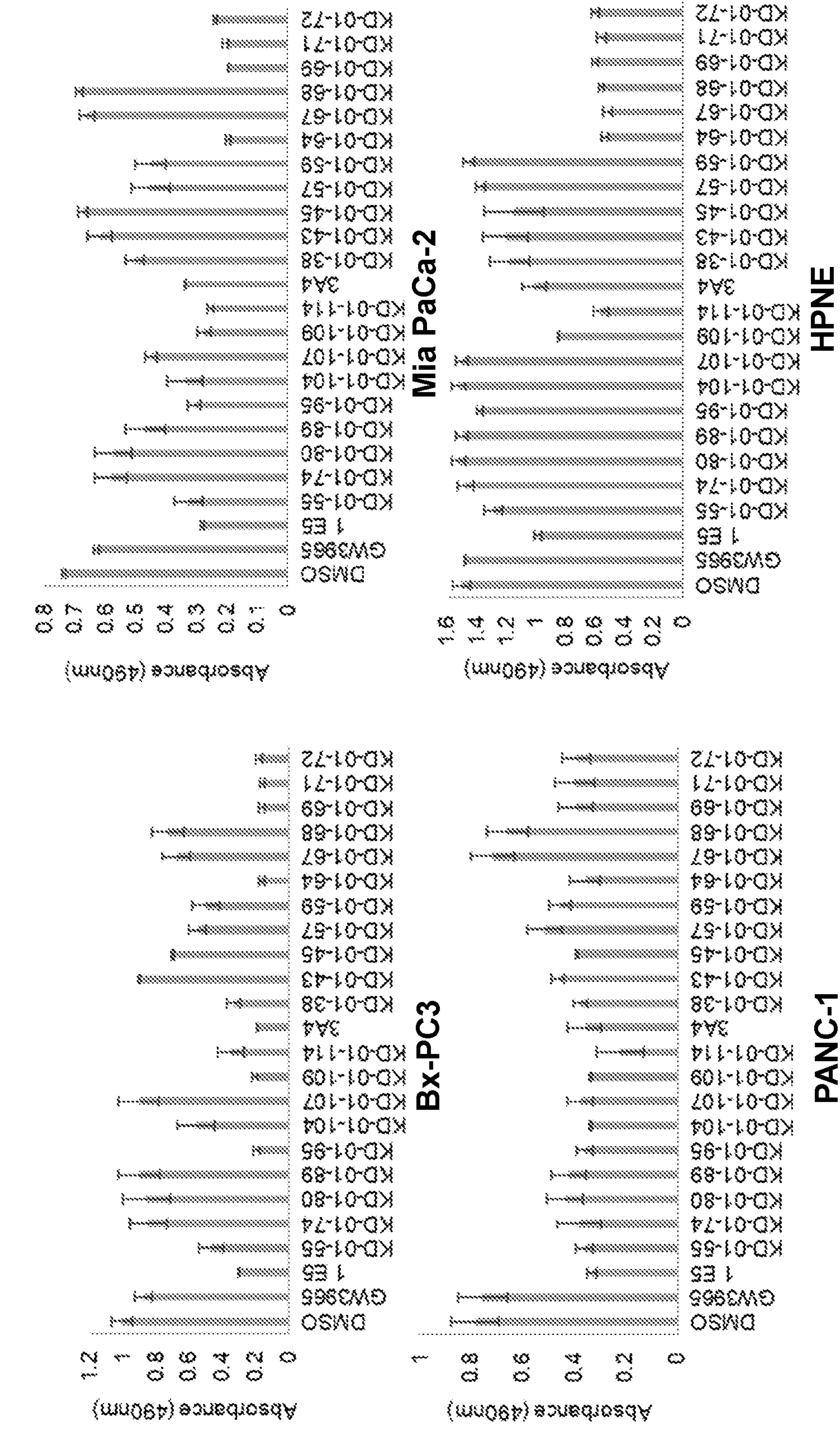
FIG. 10 shows changes in proliferation of cancer cells measured by absorbance in different pancreatic cancer cell lines after treatment with ligands and derivatives according to preferred embodiments described herein.

The initial identification and subsequent characterization of the two novel LXR ligands and their derivative compounds was carried out in screens in three human pancreatic cancer cell and one non-transformed human pancreatic epithelial cell line in three or more replicate experiments for each cell line using the WST tetrazolium salt reduction assays. FIG. 10 shows that LXR ligands 1E5 and 3A4 and select derivatives were effective in inhibiting human pancreatic cancer cells growth in tetrazolium salt reduction assays and have less or little activity against non-cancerous pancreatic epithelial cells. Both lead compounds (1E5 and 3A4) had little activity against non-transformed HPNE cells, some derivatives had little to no activity against HPNEs (KD-01-38, 43, 45, 55, 57, 59, 74, 80, 89, 95, 104), and other derivatives (KD-01-64, 67, 68, 69, 71, 72, 114) had significant activity against HPNE cells.

Figure 11:
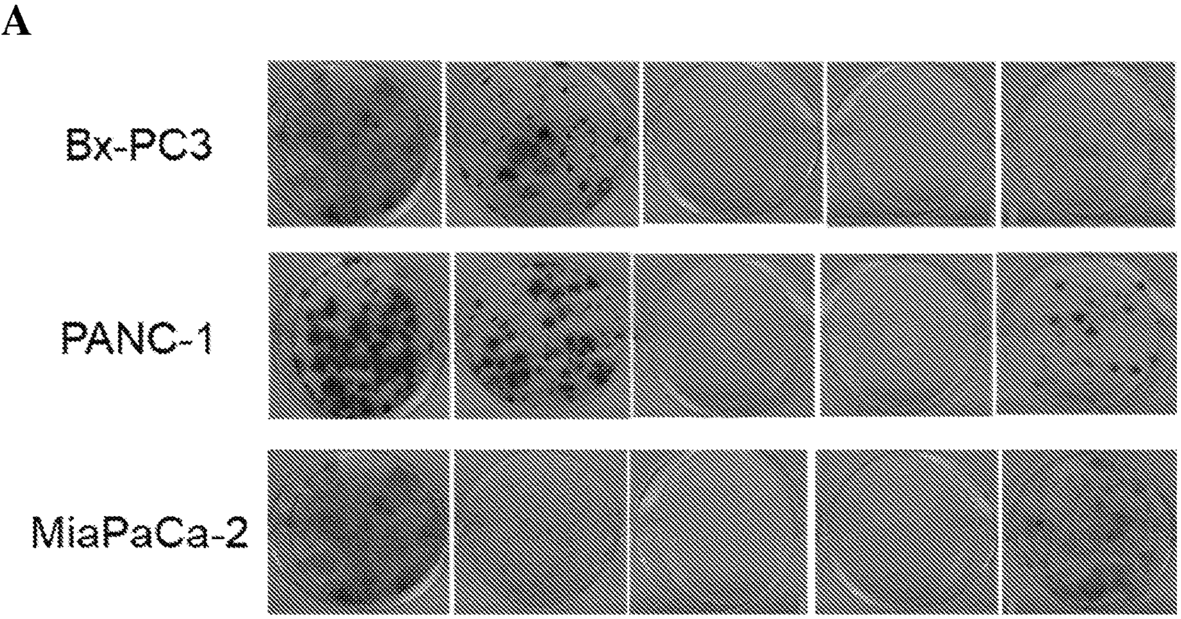
FIG. 11 shows (A) images and (B) quantification of colonies formed in long-term clonogenic assays of different pancreatic cancer cells following treatment with LXR ligands and derivatives according to preferred embodiments described herein.
Figure 12:
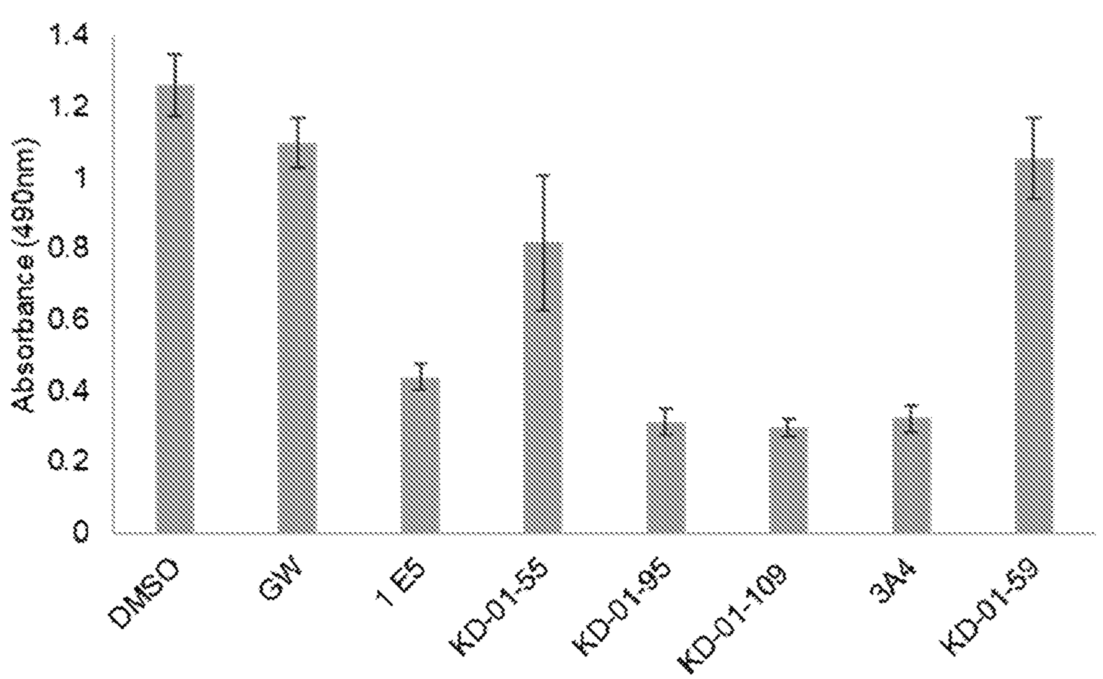
FIG. 12 size of pancreatic cancer cells isolated from tumors of a genetically engineered mouse model of pancreatic cancer after treatment with LXR ligands and derivatives according to preferred embodiments described herein.
Figure 13:
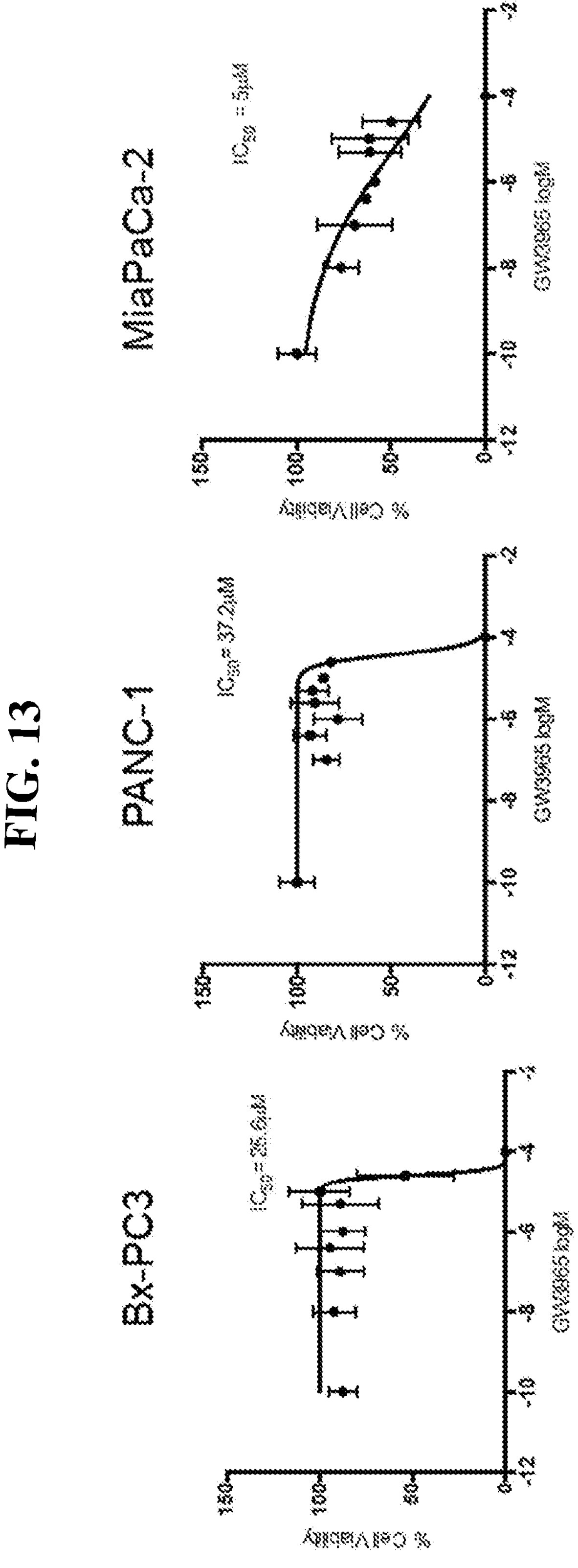
FIG. 13 shows response curves of cancer cell viability in different pancreatic cancer cell lines after treatment with GW3965 and LXR ligands according to preferred embodiments described herein.

The effects of the ligands and derivatives on the growth of PDAC cells were further validated by cell counting and clonogenic assays. FIG. 11 shows (A) images and (B) quantification of number of colonies formed in long-term clonogenic assays of different pancreatic cancer cells following treatment with LXR ligands 1E5 and 3A4, representative derivative KD-01-55, and DMSO and GW for comparison. Relevant to in vivo pre-clinical studies and clinical applications, treatments with the LXR ligands and select derivatives (KD-01-55, 95, and 109) also blocked the growth of highly aggressive KPC tumor cells derived from the most clinically relevant mouse model of PDAC. FIG. 12 shows the results in terms of tumor size determined by absorbance for tumor cells treated with LXR ligands 1E5 and 3A4 and select derivatives, with DMSO and GW for comparison. FIG. 13 shows response curves of pancreatic cancer cells treated with increasing concentrations of 1E5 and 3A4 as compared to GW3965 in different human PDAC cell lines. The response curves of cells treated with increasing concentrations of 1E5 and 3A4 also showed more potent activity as compared to GW3965.

Figure 14:
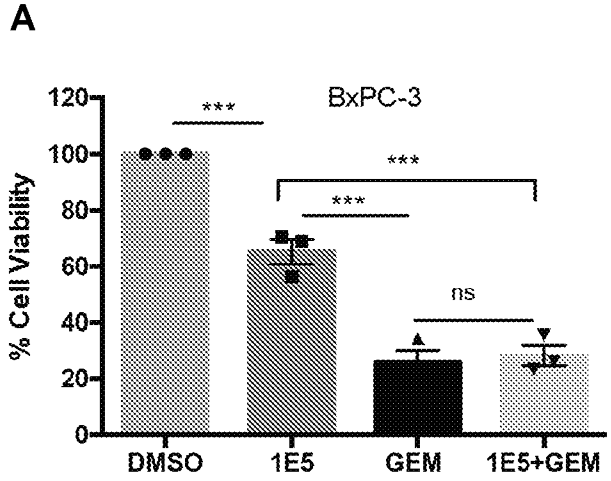
FIG. 14 shows cell viability in human PDAC cell lines (A) BxPC-3, (B) MIA PaCa-2, and (C) PANC-1 after treatment with 1E5, gemcitabine, and a combination of 1E5 and gemcitabine, with control (DMSO).
Figure 14:
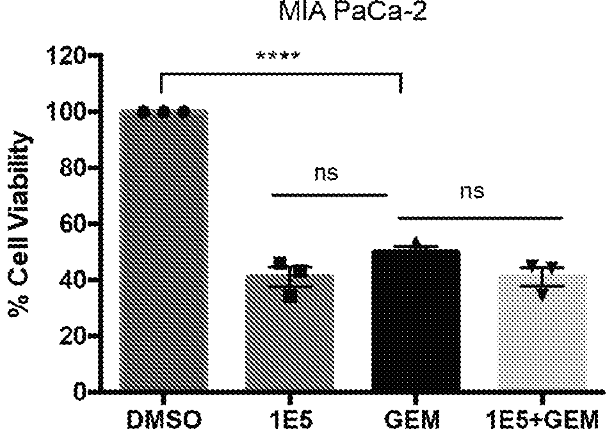
Figure 14:
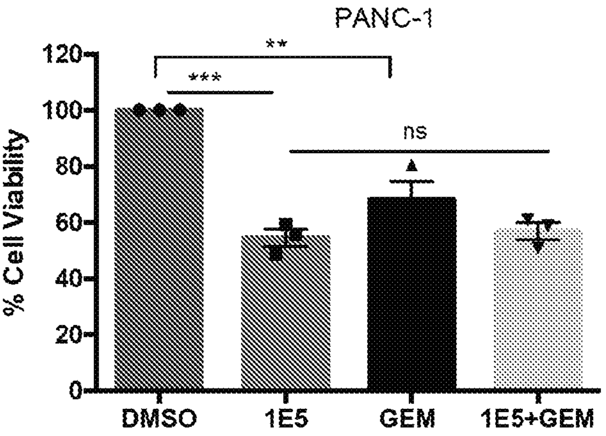
Figure 15:
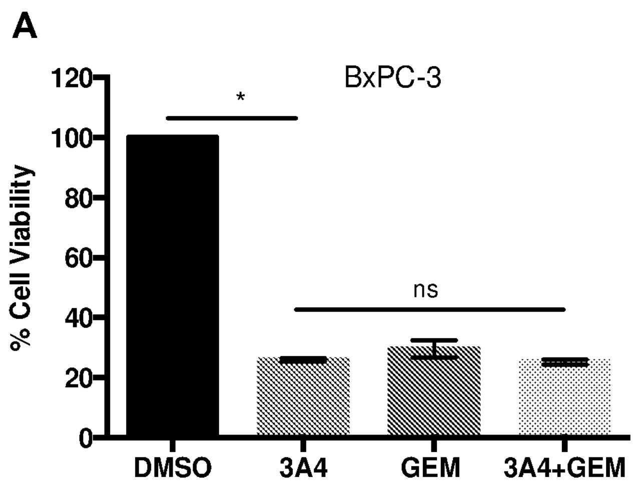
FIG. 15 shows cell viability in human PDAC cell lines (A) BxPC-3, (B) MIA PaCa-2, and (C) PANC-1 after treatment with 3A4, gemcitabine, and a combination of 3A4 and gemcitabine, with control (DMSO).
Figure 15:
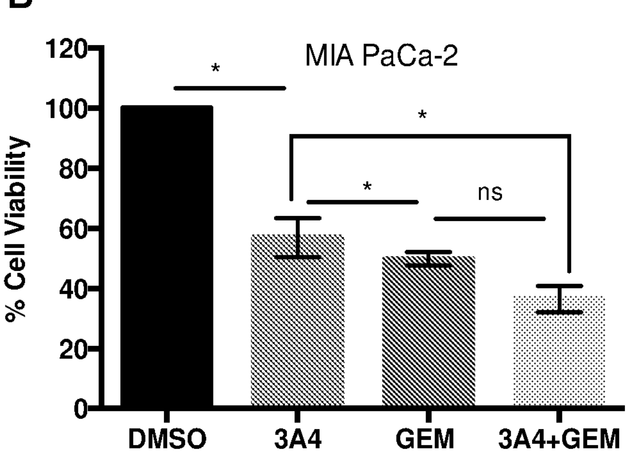
Figure 15:
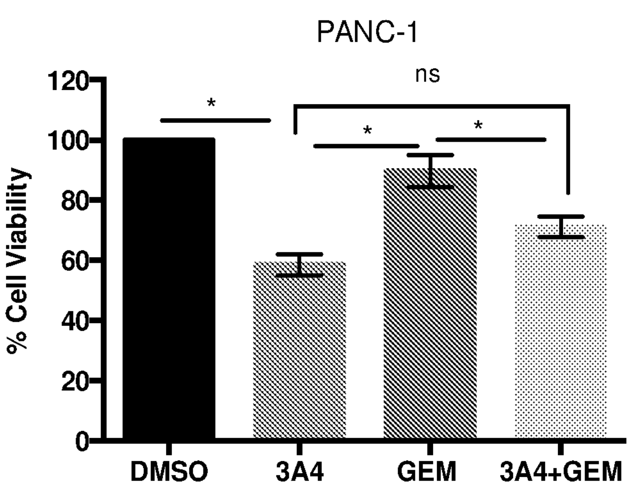

Gemcitabine is the current standard-of-care chemotherapeutic agent for the treatment of pancreatic cancer. Its toxicity, however, is a significant clinical challenges in the management of pancreatic cancer. To assess the efficacy of combining gemcitabine with 1E5, 3A4, or their derivatives, PDAC cells were treated with either gemcitabine, 1E5, or 3A4 alone or in combination at half the concentration of each of the compounds. FIG. 14 shows the cell viability in human PDAC cell lines (A) BxPC-3, (B) MIA PaCa-2, and (C) PANC-1 after treatment with 1E5, gemcitabine, and a combination of 1E5 and gemcitabine, with control (DMSO). FIG. 15 shows the cell viability in human PDAC cell lines (A) BxPC-3, (B) MIA PaCa-2, and (C) PANC-1 after treatment with 3A4, gemcitabine, and a combination of 3A4 and gemcitabine, with control (DMSO). Combining reduced amounts of gemcitabine with 1E5 or 3A4 resulted in similar reduction of PDAC cell proliferation and survival as the higher concentration of gemcitabine alone. These results indicate that the less toxic LXR ligands described herein may be used to supplement gemcitabine, thereby requiring a lower concentration of the more toxic chemotherapeutic agent while achieving the same efficacy in inhibiting pancreatic cancer cells.

Example 6

1E5 and 3A4 Modulate LXR Activity and Expression and Inhibit Breast Cancer Cell Proliferation.

Figure 16:
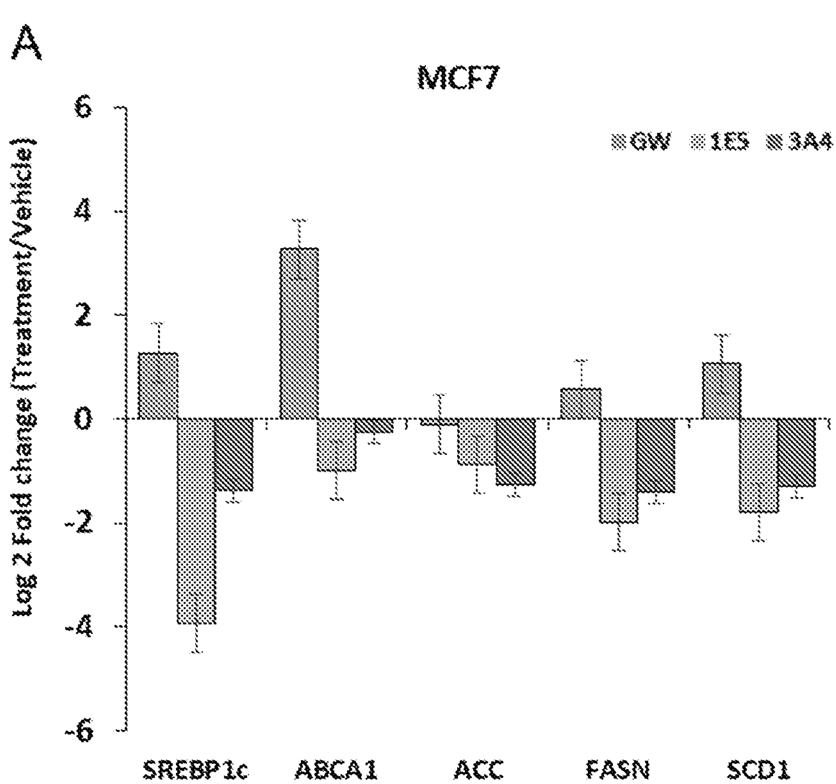
FIG. 16 shows down-regulation of LXR target genes by inverse agonists 1E5 and 3A4 in (A) estrogen receptor (ER)-positive MCF-7 cell line and (B) triple-negative breast cancer MDA-MB-231 cells as compared to GW3965 synthetic agonist, and where treatments with 3A4 decreased the proliferation of (C) MCF-7 cells, whereas both novel ligands inhibited (D) MDA-MB-231 cell.
Figure 16:
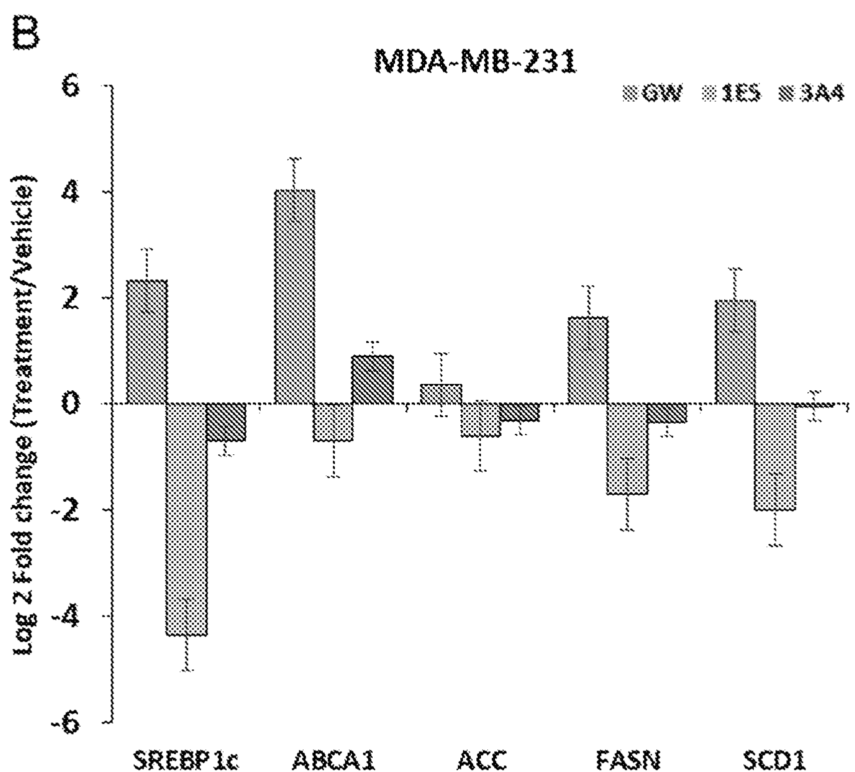
Figure 17:
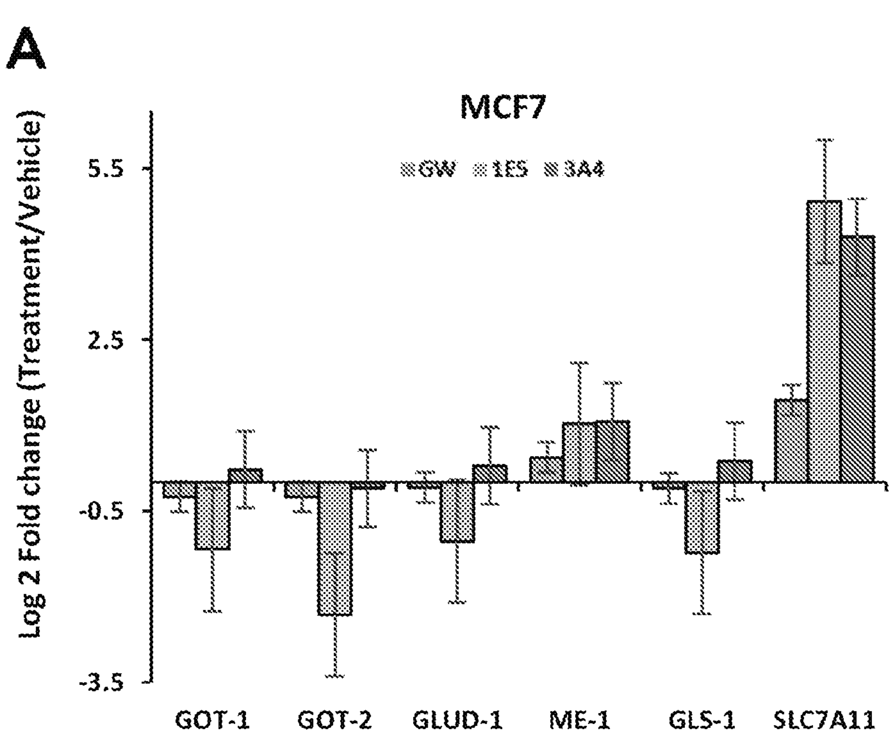
FIG. 17 shows a general down-regulation of transcript levels of genes involved in glutamine biosynthesis pathway commonly up-regulated in cancer in (A) MCF-7 and (B) MDA-MB-231 cells.
Figure 17:
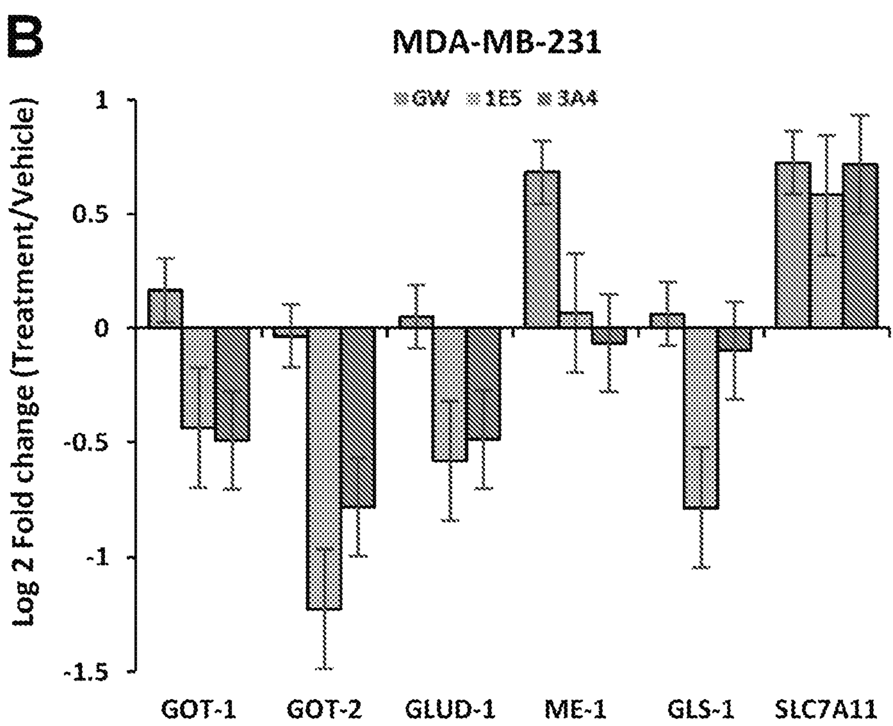
Figure 18:
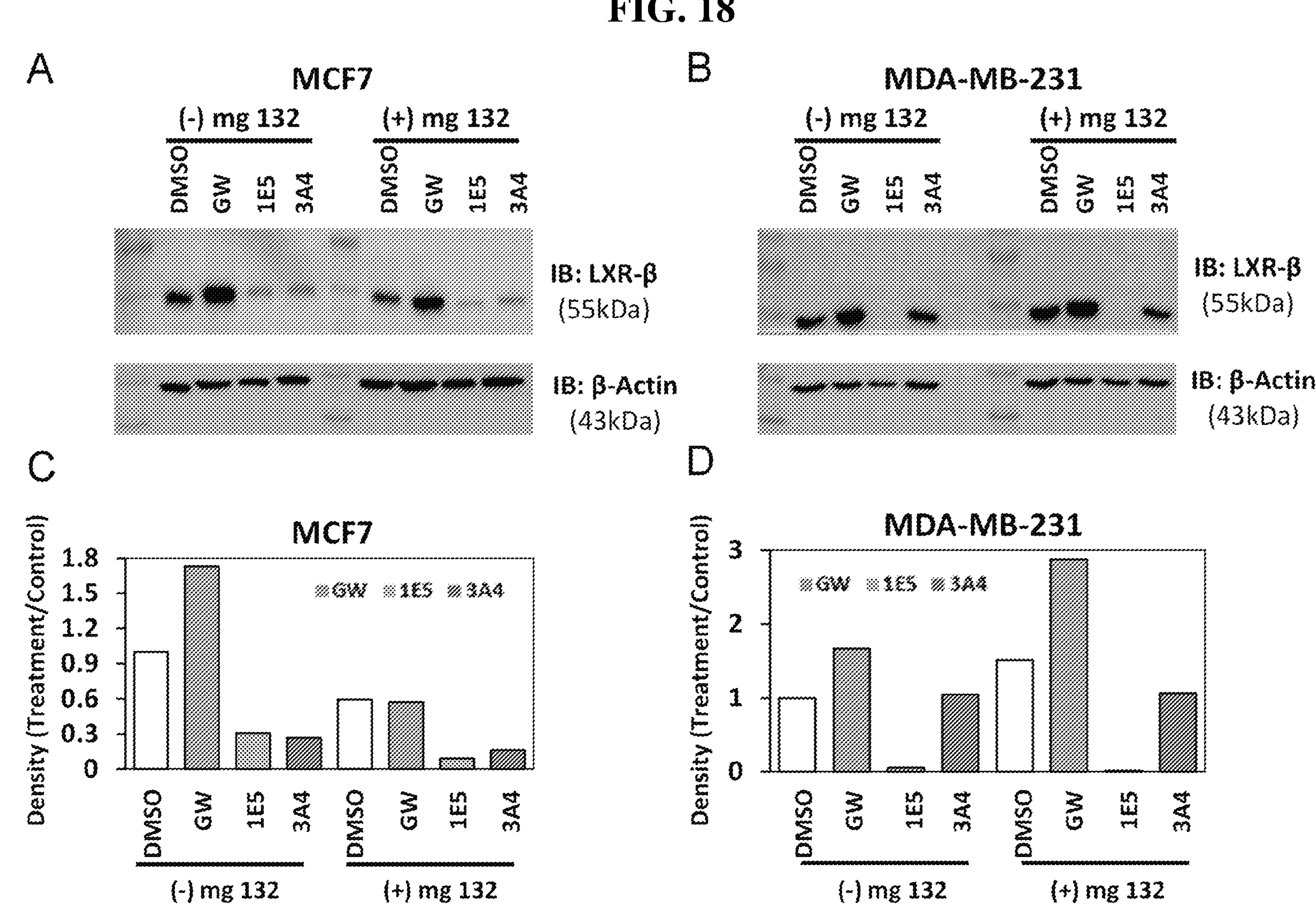
FIG. 18 shows effects of treatments with 1E5 and 3A4 on LXR protein levels in (A) MCF-7 and (B) MDA-MB-231 cells in the absence and presence of proteasome inhibitor MG132 from a western blot experiment, and band intensity from the blot images analyzed and presented for (C-D) two cell lines.

The inhibitory effects of LXR ligands in breast cancer cells have been shown previously. It was surmised that that novel LXR ligands 1E5 and 3A4 may similarly inhibit breast cancer cells. FIG. 16 (A-B) shows that both ligands generally down-regulated the expression of LXR target genes in estrogen receptor (ER)-positive (MCF-7) and triple-negative (MDA-MB-231) breast cancer cells, similar to their actions as inverse agonists in pancreatic cancer cells. FIG. 16 (C-D) shows that 3A4 inhibited the proliferation of MCF-7 cells and both ligands inhibited MDA-MB-231 cells. FIG. 17 (A-B) shows the effects of novel ligands on the expression of genes involved in glutamine transport and biosynthesis, a metabolic process commonly mutated in cancers. These results are similar to the observations in pancreatic cancer cells. FIG. 18 (A-B) shows that both ligands act as degraders of LXR proteins in MCF-7 cells, whereas only 1E5 degraded LXR in MDA-MB-231 cells. The observed decreases in LXR protein levels were not affected by proteasome inhibitor MG132. FIG. 18 (C-D) represents the quantification of the band intensities shown in FIG. 18 (A-B). These results support the application of these compounds and their derivatives in the breast cancer treatment, including triple negative breast cancers which currently lack effective targeted therapeutic options Example 7

1E5 and 3A4 are LXR Inverse Agonists.

Figure 19:
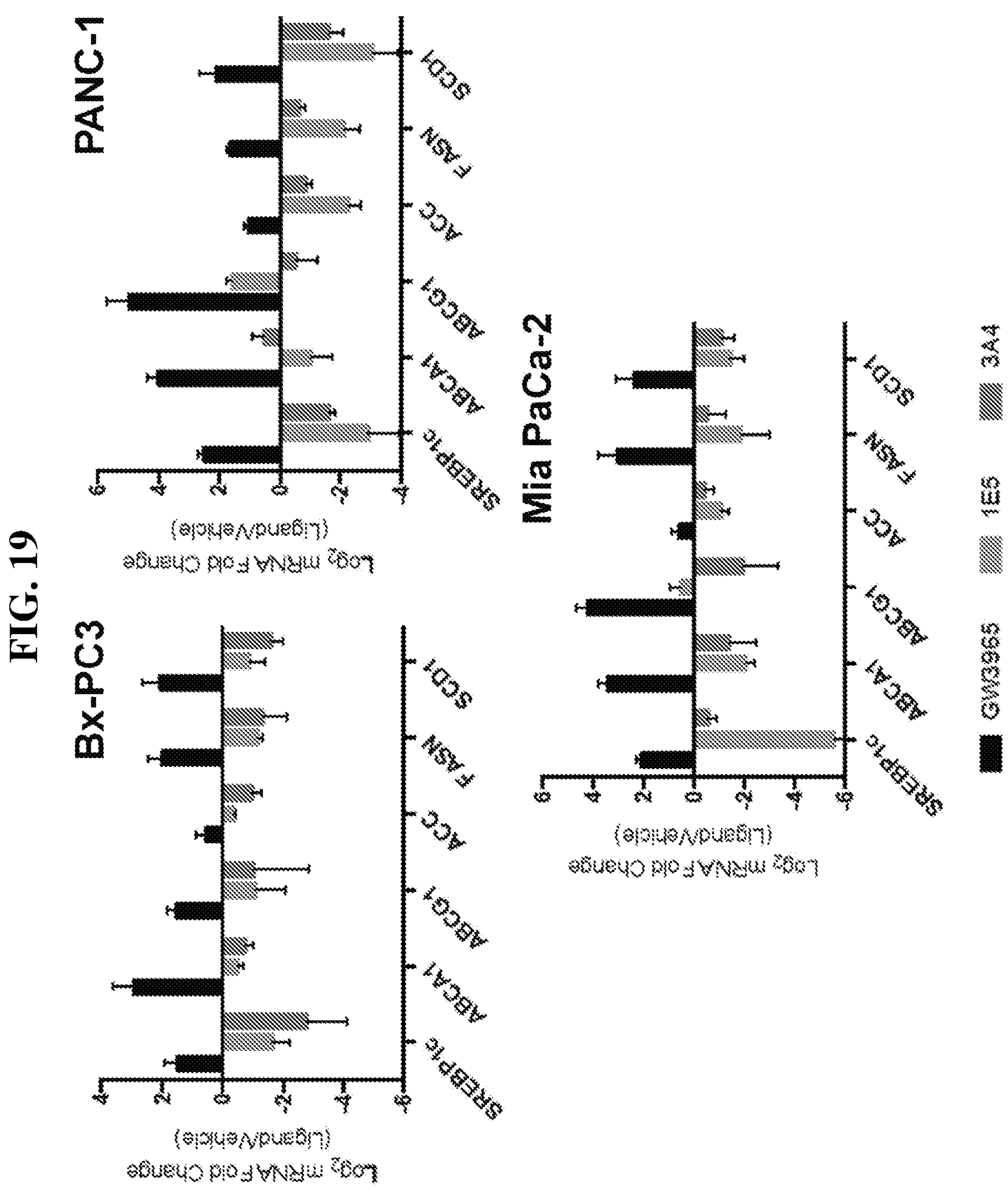
FIG. 19 shows effects on expression of LXR target genes in different pancreatic cancer cell lines after treatment with GW3965 and LXR ligands according to preferred embodiments described herein.

To characterize the activity of the newly discovered ligands, the expression of LXR target genes SREBF1c, ABCA1, and ABCG1 was examined following treatment with vehicle, synthetic agonist GW3965, and Compounds 1E5 and 3A4. FIG. 19 shows that LXR ligands 1E5 and 3A4 function as inverse agonists by reducing the expression of LXR target genes as compared to the synthetic LXR agonist GW3965 which increased target gene expression. Basal expression of SREBF1c, the canonical LXR target gene involved in the regulation of glucose and lipid metabolism, was disrupted by the addition of novel LXR ligands, whereas their expression was induced following treatment with synthetic agonist GW3965 in all three pancreatic cancer cell lines tested, whereas the effects on ABCA1 and ABCG1 varied between the two novel ligands and across the cell lines. These results indicate that these novel ligands function as inverse agonists, with both cell type- and ligand-specific effects. Consistent with the anti-tumor activity of these novel inverse agonists, knockdown of LXRβ by siRNA in a previous study also significantly reduced PDAC cell growth and proliferation.

Figure 20:
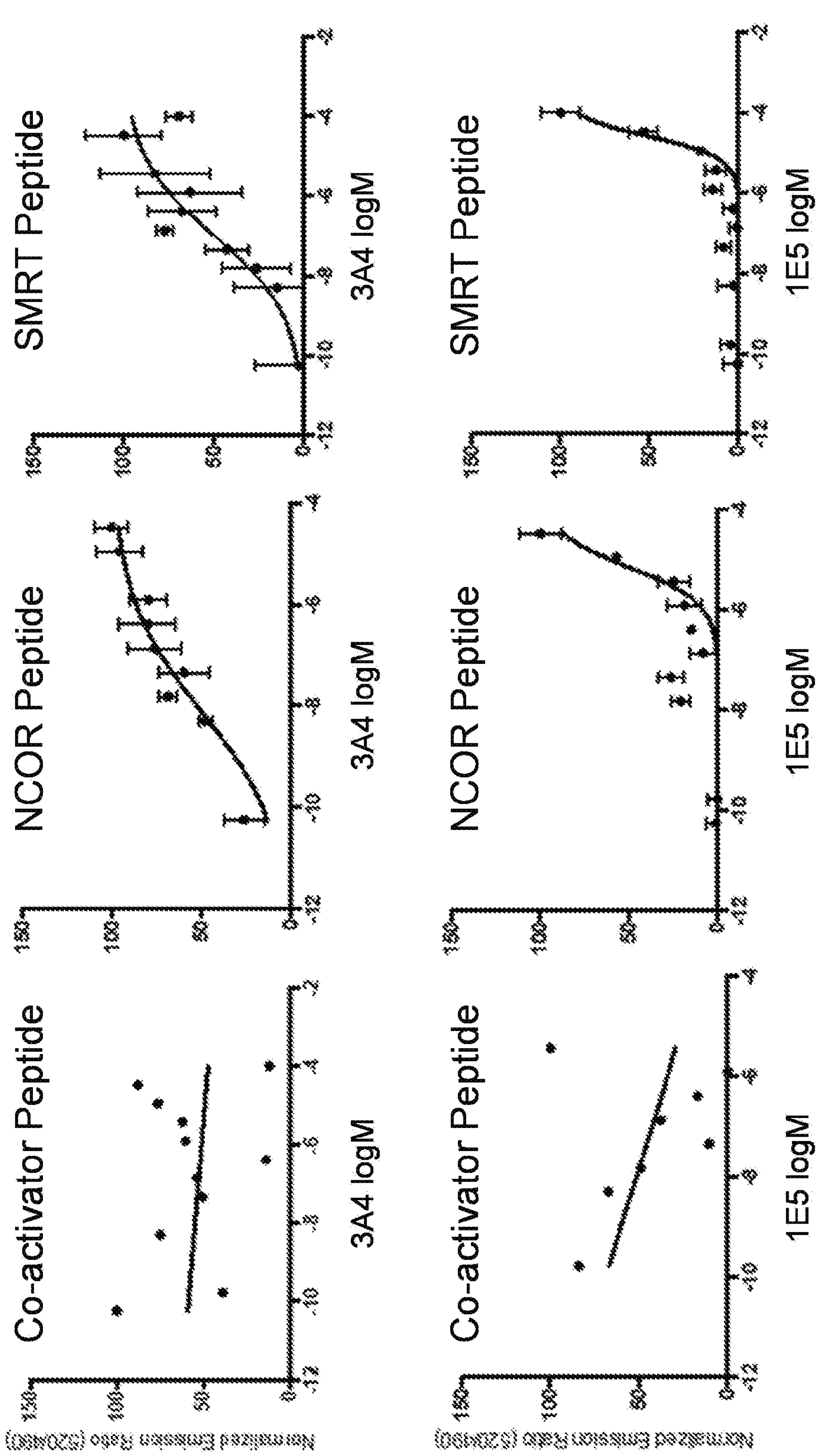
FIG. 20 shows (A) results and (B) comparison of TR-FRET assays of LXR ligand-binding domain interaction with co-activator (D22) and co-repressor (NCOR and SMRT-ID2) peptides.
Figure 21:
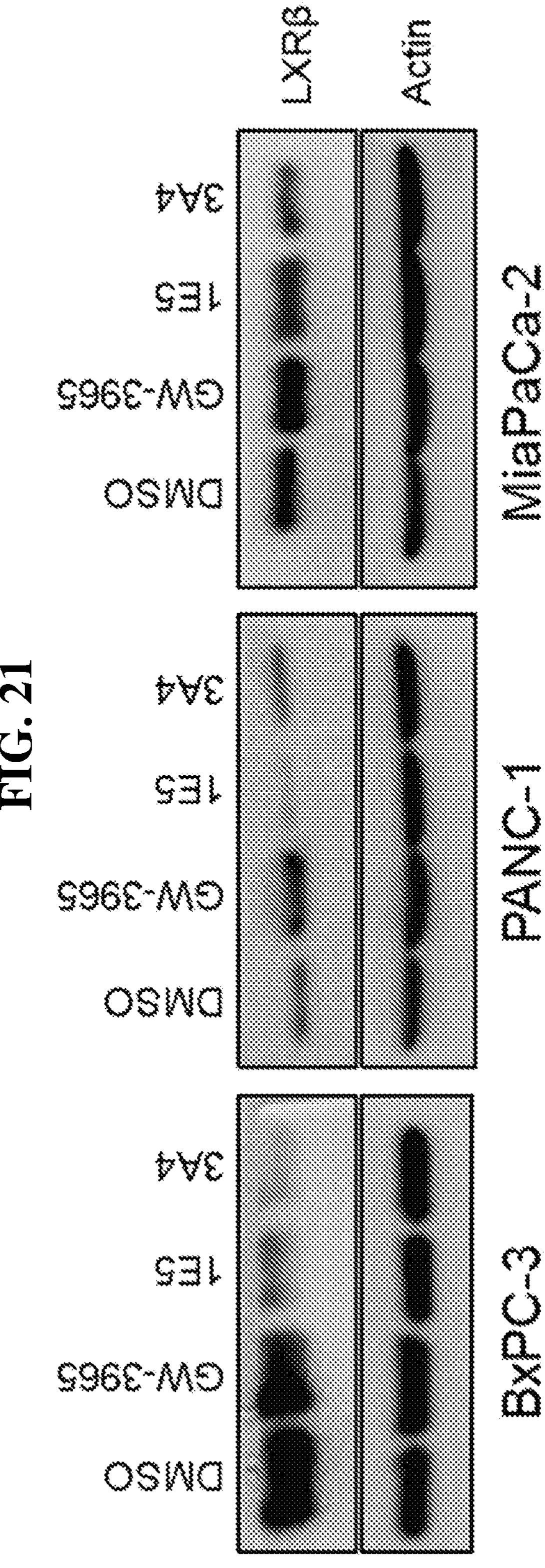
FIG. 21 shows expression of LXR proteins in different pancreatic cancer cell lines following long-term treatments with GW3965 and LXR ligands according to preferred embodiments described herein.

Since a LXR inverse agonist was previously reported to affect glucose and lipid metabolism in cancer cells, the effects of the two novel inverse agonists were also examined on other LXR target genes involved in glycolysis and lipogenesis and found that ligand treatment decreased the expression of FASN, SCD, and ACC in pancreatic cancer cells, as shown in FIG. 19. To elucidate mechanisms of inverse agonism by the novel ligands, TR-FRET experiments were conducted to determine the effects of 1E5 and 3A4 on the recruitment of NR co-activators and co-repressors. FIG. 20 shows that TR-FRET assays of LXR ligand-binding domain interaction with co-activator (D22) and co-repressor (NCOR and SMRT-ID2) peptides revealed recruitment of co-repressors by novel inverse agonists 1E5 and 3A4 as compared to vehicle (DMSO) and agonist (GW) treatments. Treatments with both compounds did not affect co-activator peptide binding to LXR ligand-binding domain but increased the binding of both NCOR and SMRT co-repressor peptides. In addition to their functions as inverse agonists, extended treatments with 1E5 and 3A4 also destabilized or decreased LXR proteins. FIG. 21 shows that long-term treatments with 1E5 and 3A4 decreased LXR protein levels. These observations are consistent with published findings that knockdown of LXR expression also decreased PDAC proliferation and viability.

Example 8

Potential Mechanisms of Action of Novel LXR Inverse Agonists.

Figure 22:
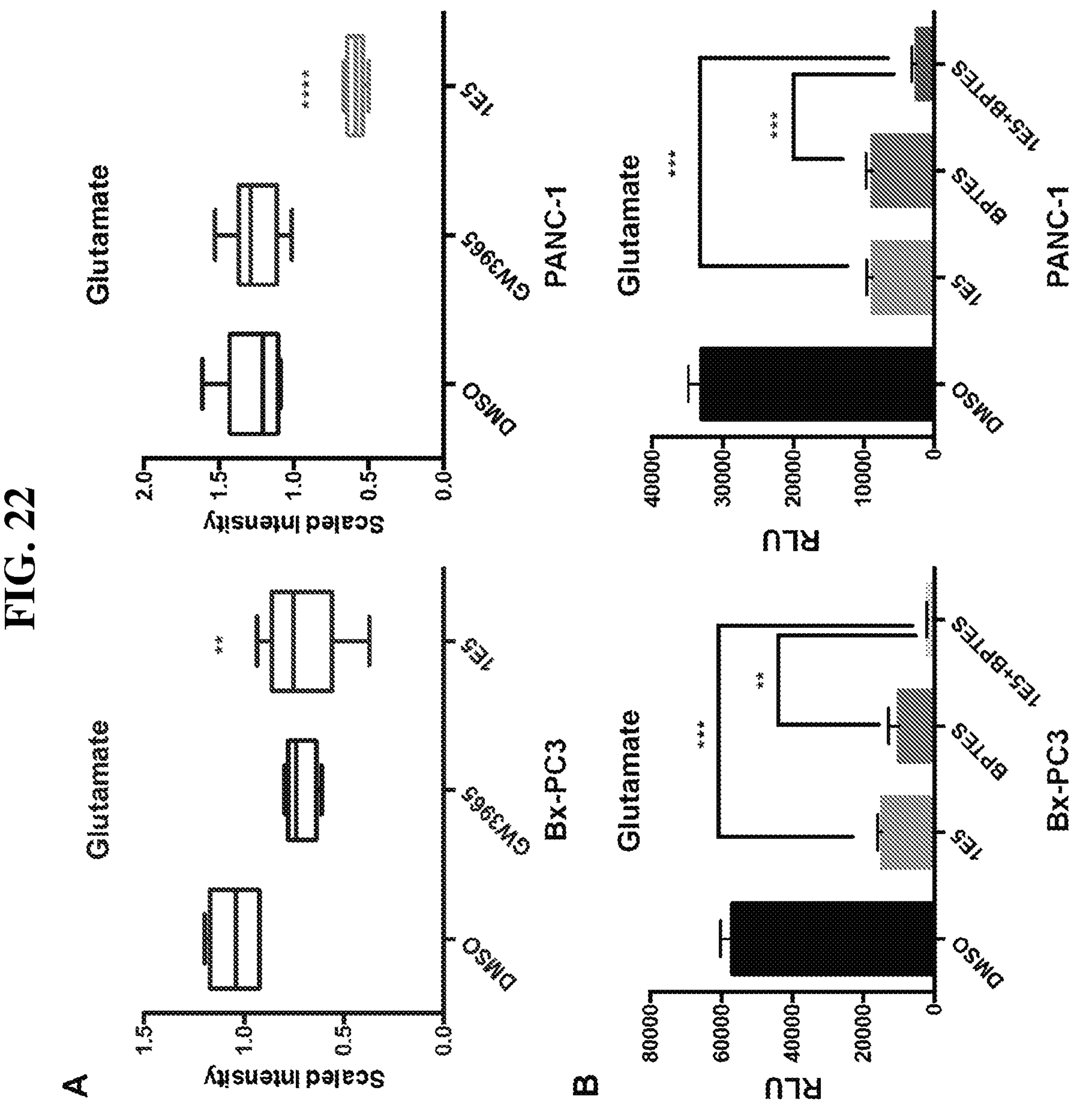
FIG. 22(A) shows results of metabolomic analysis using mass spectroscopy showing glutamate levels in different pancreatic cancer cell lines following treatments with GW3965 and a LXR ligand according to preferred embodiments described herein.
FIG. 22(B) shows results of enzymatic assays showing glutamate levels in different pancreatic cancer cell lines following treatment with a LXR ligand according to preferred embodiments described herein and glutaminase inhibitor BPTES.

To further characterize the mechanisms of action of novel LXR modulators 1E5 and 3A4, metabolomic and transcriptomic analysis of pancreatic cancer cells were conducted in response to treatment. Treatments with 1E5 inhibited glutamine biosynthesis, a key pathway in cancer metabolism. PDAC tumors have altered metabolism to support its growth and survival. Previous studies have reported that Kras upregulates the non-canonical use of glutamine to maintain NADPH/NADP+ ratio which in turn regulates redox homeostasis. This unconventional use of glutamine by PDAC cells fuel cancer cell proliferation and survival. Glutamine metabolism in PDAC has two unique functions: 1. Glutamine-derived Glutamate is used for glutathione (GSH) biosynthesis. 2. Glutamine facilitates generation of reducing equivalents in the form of NADPH. In PDAC mitochondria, glutamine is converted to glutamate by glutaminase enzyme (GLS1). This glutamine derived glutamate is conventionally converted to alpha-ketoglutarate by glutamate dehydrogenase (GLUD1) to fuel citric acid cycle. However, in PDAC cells glutamate is converted to aspartate in cytosol which is converted to malic acid and NADPH is produced during this process. This process is essential to maintain redox homeostasis in the tumor. However, this non-canonical use of glutamine is dispensable in non-malignant cells. Therefore, targeting GLS1 to decrease the bioavailability of glutamate to act as source of nitrogen and carbon for the synthesis of amino acids and nucleic acids is a viable strategy to target PDAC tumors. FIG. 22 shows glutamate levels in pancreatic cancer cells decreased following 1E5 treatment. FIG. 22A shows results of a metabolic analysis using mass spectroscopy, revealing decreases in glutamate levels. FIG. 22B shows decreases in glutamate levels following 1E5 treatments validated by enzymatic assays and synergistic effects with glutaminase inhibitor BPTES. The intracellular levels of glutamate in PDAC cells is significantly reduced when treated with 1E5 for 48 hours. The effect of 1E5 is similar to BPTES, a potent GLS1 inhibitor. Importantly, combination treatment of 1E5 showed synergistic effects on reducing the glutamate levels.

Figure 23:
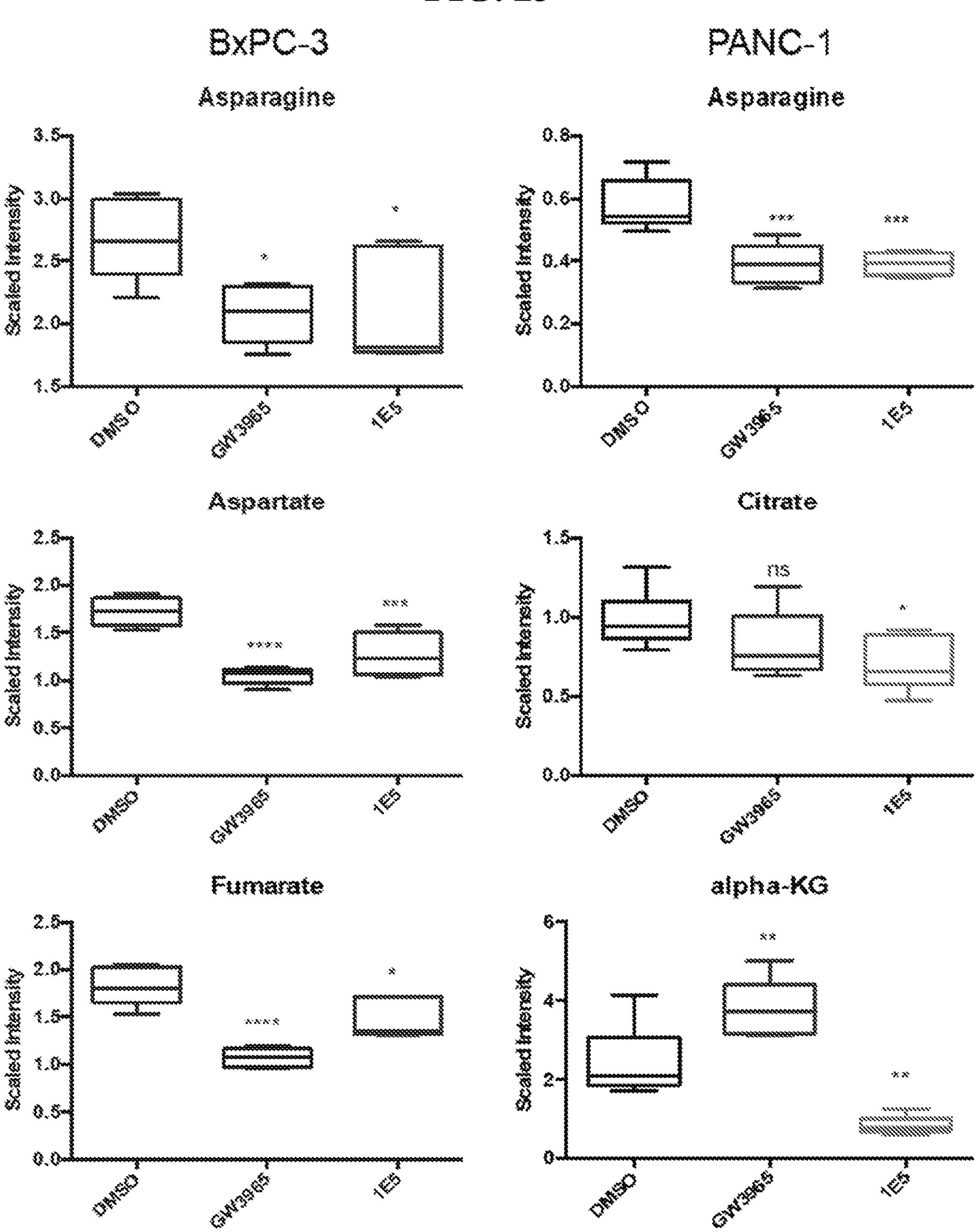
FIG. 23 shows results of metabolomic analysis using mass spectroscopy showing metabolite levels in different pancreatic cancer cell lines following treatments with GW3965 and a LXR ligand according to preferred embodiments described herein.
Figure 24:
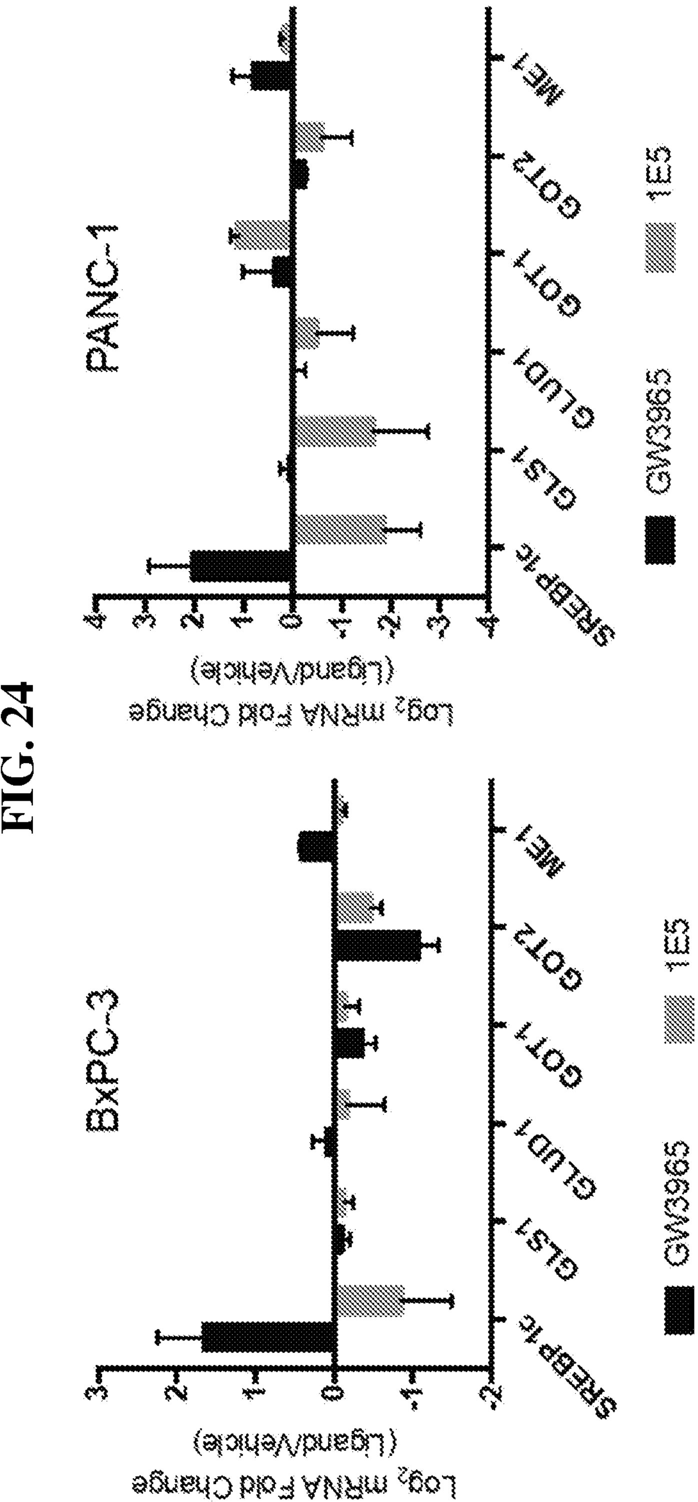
FIG. 24 shows effects on expression of genes involved in glutamine metabolism in different pancreatic cancer cell lines after treatment with GW3965 and a LXR ligand according to preferred embodiments described herein.
Figure 25:
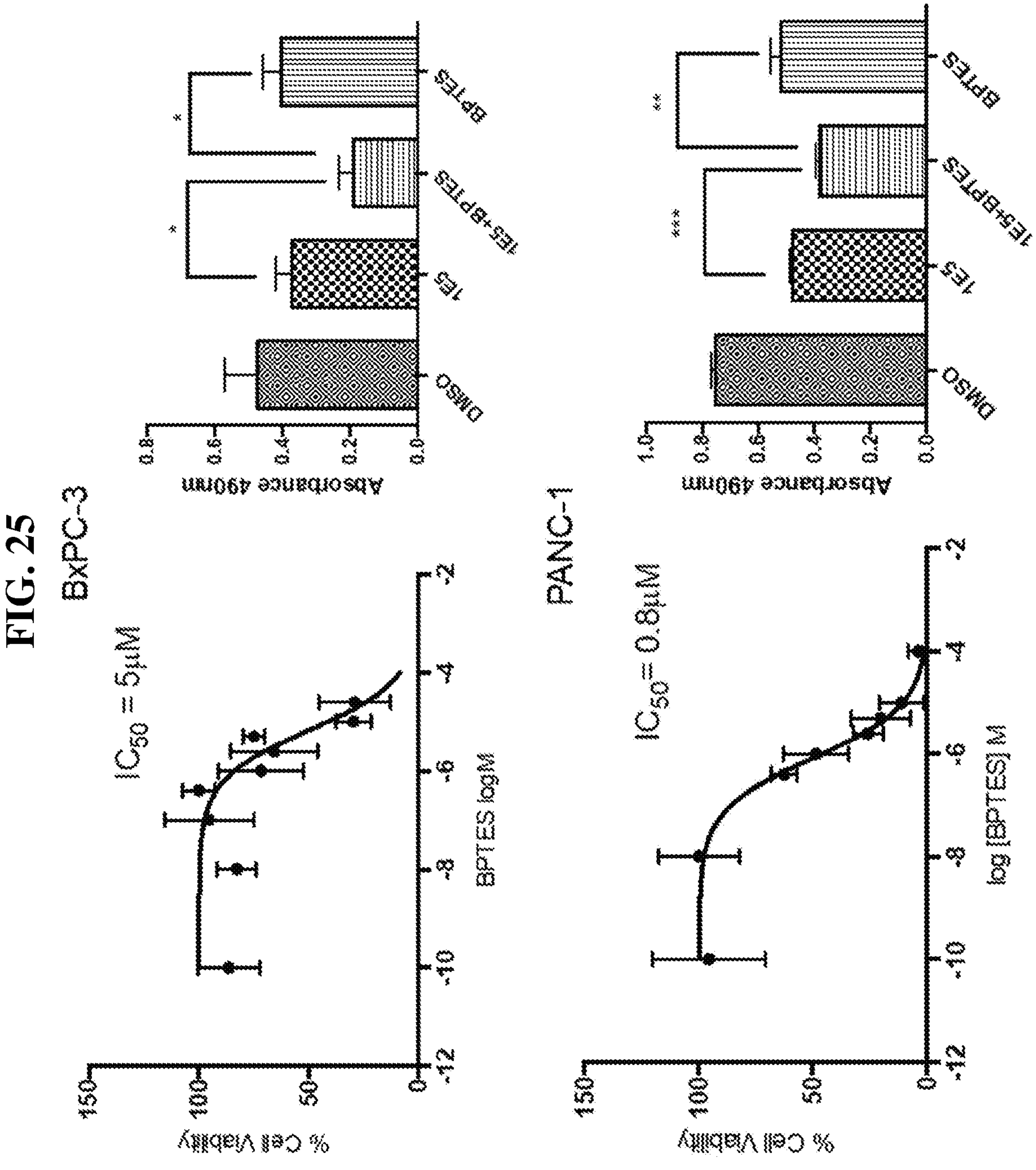
FIG. 25 shows cell viability and effect on growth in pancreatic cancer cells following treatment with glutaminase inhibitor BPTES and a LXR ligand according to preferred embodiments described herein.

Consistent with its effects on glutamate levels, 1E5 downregulated the levels of TCA cycle intermediates such as alpha-KG (downregulation of GLUD1 and GOT2), citrate and fumarate. FIG. 23 shows results of a metabolomic assay showing decreases in metabolites downstream of glutamine metabolism pathway following 1E5 treatments. TCA cycle intermediates act as anaplerotic substrate for gluconeogenesis and lipogenesis. Moreover, 1E5 decreased the levels of asparagine and aspartate which are the source of glutamine independent, glutamate producing metabolites. Glutaminase1 and glutamic-oxoacetic transaminase 2 (GOT 2) enzymes are upregulated in PDAC tumors and are associated with poor prognosis. GOT2 converts glutamine-derived glutamate to alpha-KG. During this process oxaloacetate is converted to aspartate which is required to maintain redox homeostasis. Studies have shown that inhibition of GOT2 in PDAC promotes senescence. FIG. 24 shows results of qPCR analysis, showing that 1E5 downregulated the expression of GLS1 and GOT2 in PDAC cells. Functionally, combination treatment with 1E5 and BPTES shows additive anti-proliferative effect in PDAC cells. FIG. 25 shows inhibition of glutaminase by BPTES reduced pancreatic cancer cell viability and showed a synergistic effect when combined with 1E5. These results indicate that PDAC cells are dependent on glutamine-derived glutamate for its growth and survival, and 1E5, similar to a known GLS1 inhibitor, can disrupt the production of glutamate by glutaminolysis.

Figure 26:
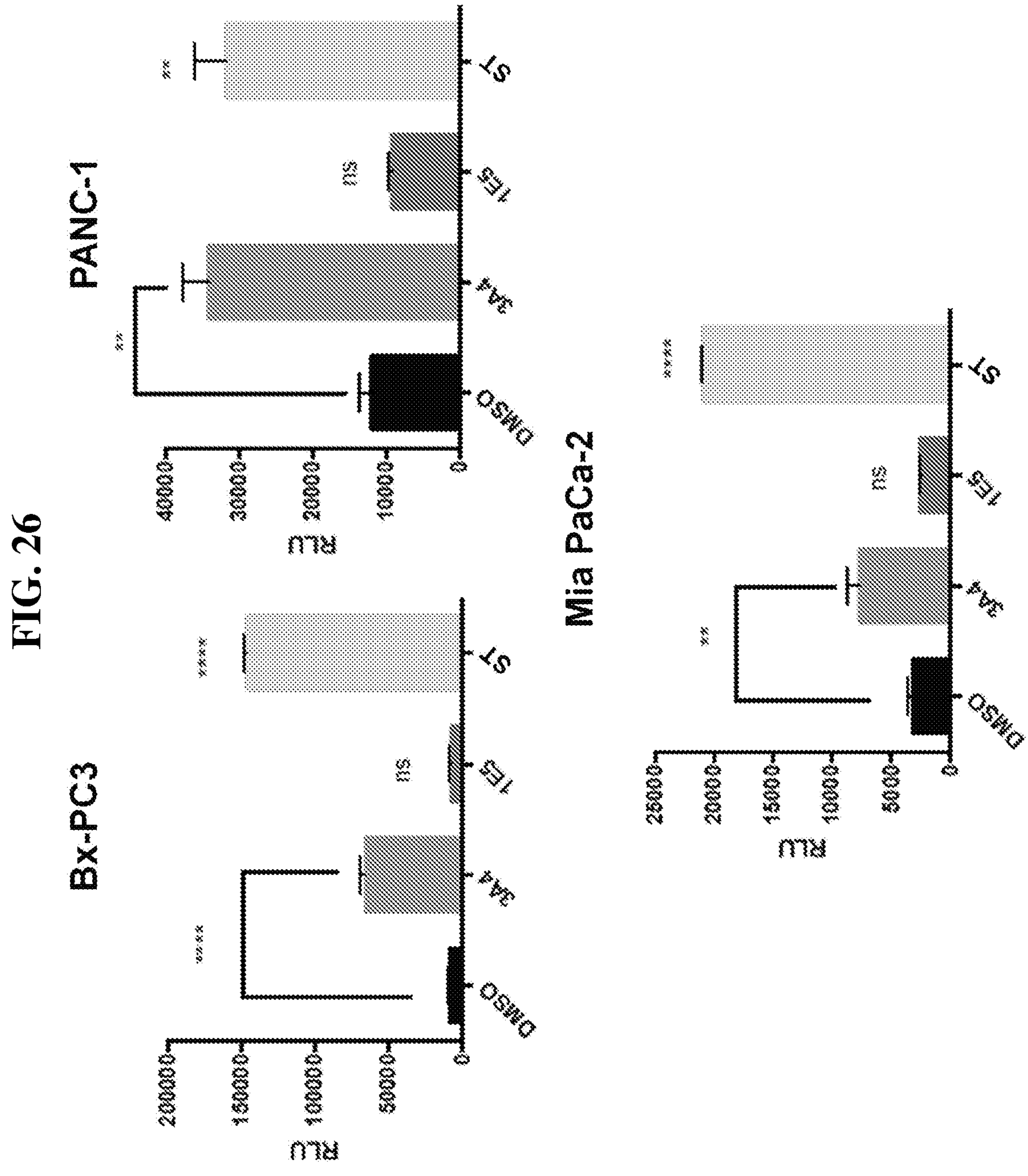
FIG. 26 shows induction of pro-apoptotic caspase cleavage in pancreatic cancer cells lines following treatment with LXR ligands according to preferred embodiments described herein.
Figure 27:
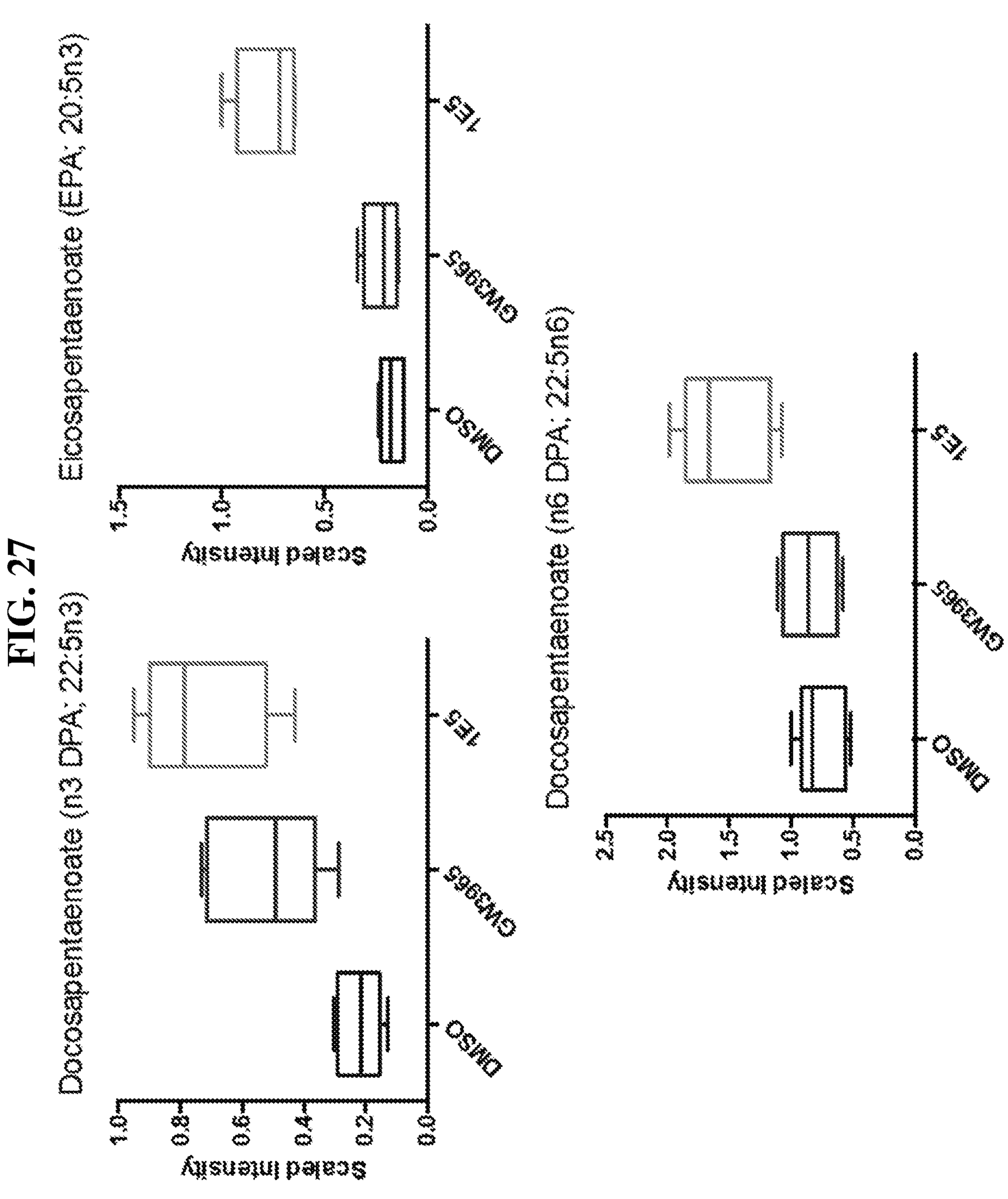
FIG. 27 shows levels of ferroptosis-related intracellular polyunsaturated fatty acids (PUFAs) in pancreatic cancer cells after treatment with GW3965 and a LXR ligand according to preferred embodiments described herein.
Figure 28:
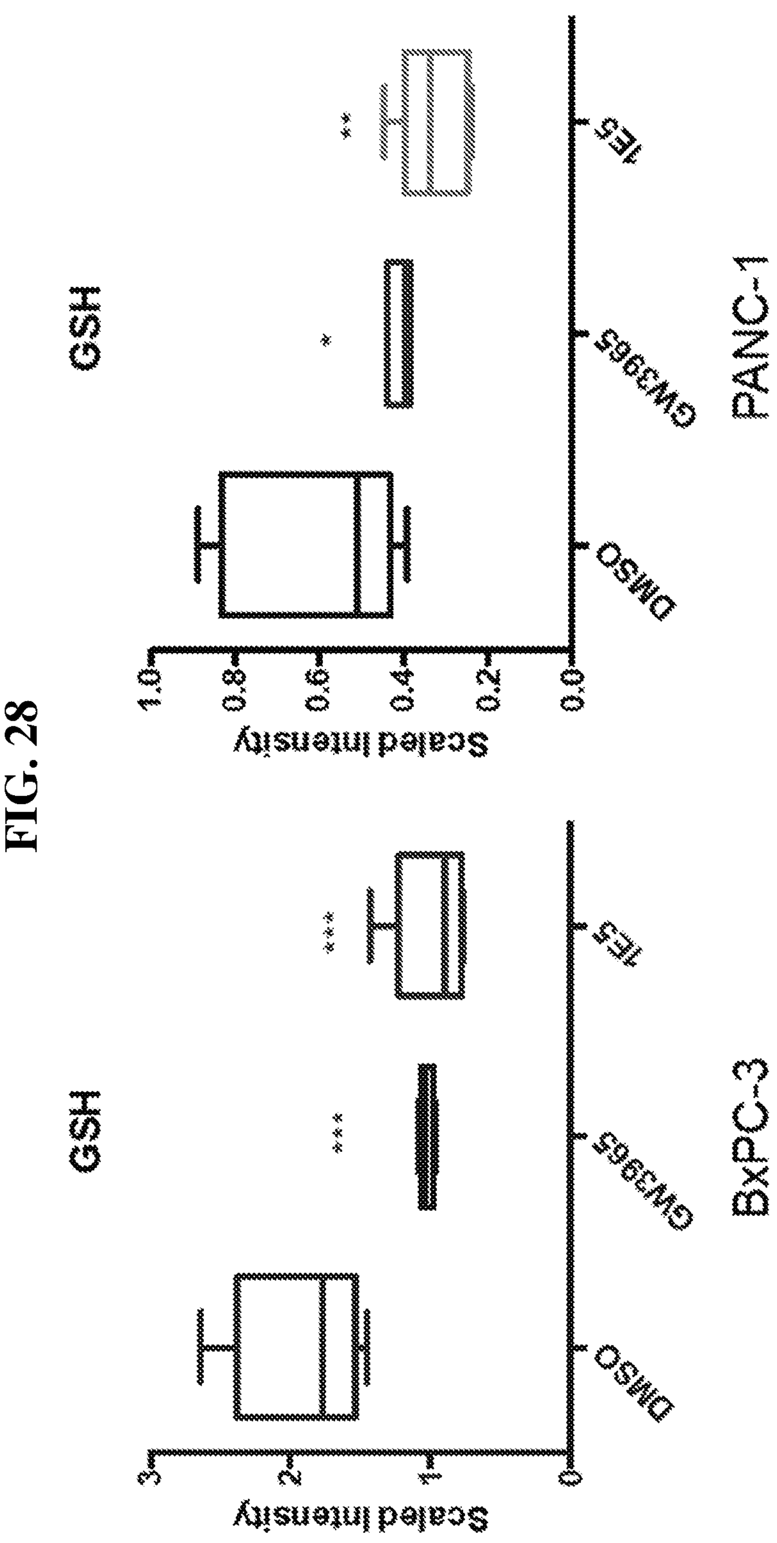
FIG. 28 shows levels of glutathione (GSH) in pancreatic cancer cells after treatment with GW3965 and a LXR ligand according to preferred embodiments described herein.

To determine if 1E5 and 3A4 can induce apoptosis, PDAC cells were treated with the LXR ligands and subjected to pro-apoptotic caspase cleavage analysis. FIG. 26 shows that treatments with 3A4 induced pro-apoptotic caspase cleavage whereas 1E5 treatments did not. Metabolomic profiling following treatments with the two ligands indicated the activation of two distinct cell death mechanisms. Ferroptosis is a non-apoptotic form of cell death which is characterized by accumulation of lipid peroxides by loss of glutathione peroxidase 4 (GPX4) activity. It can also be induced by accumulation of intracellular iron and depletion of reduced glutathione (GSH). GPX4 is an anti-oxidant enzyme involved in conversion of PUFA peroxides to PUFA alcohols. GSH is a critical cofactor of GPX4 and acts as a reducing agent to reduce the lipid peroxides. Therefore, direct inhibition of GPX4 activity or reduction in GSH levels trigger ferroptosis. The second mechanism of inducing ferroptosis is accumulation of polyunsaturated fatty acids (PUFAs) in cells. Studies have shown that PUFAs are the most susceptible lipids to peroxidation. FIG. 27 shows levels of ferroptosis-related intracellular polyunsaturated fatty acids (PUFAs) in PANC-1 pancreatic cancer tells after treatment with 1E5. FIG. 28 shows levels of glutathione (GSH) which protects cells against ferroptotic cell death in pancreatic cancer cells after treatment. PDAC cells treated with 1E5 have increased levels of PUFAs (FIG. 27), and decreased level of GSH (FIG. 28).

Figure 29:
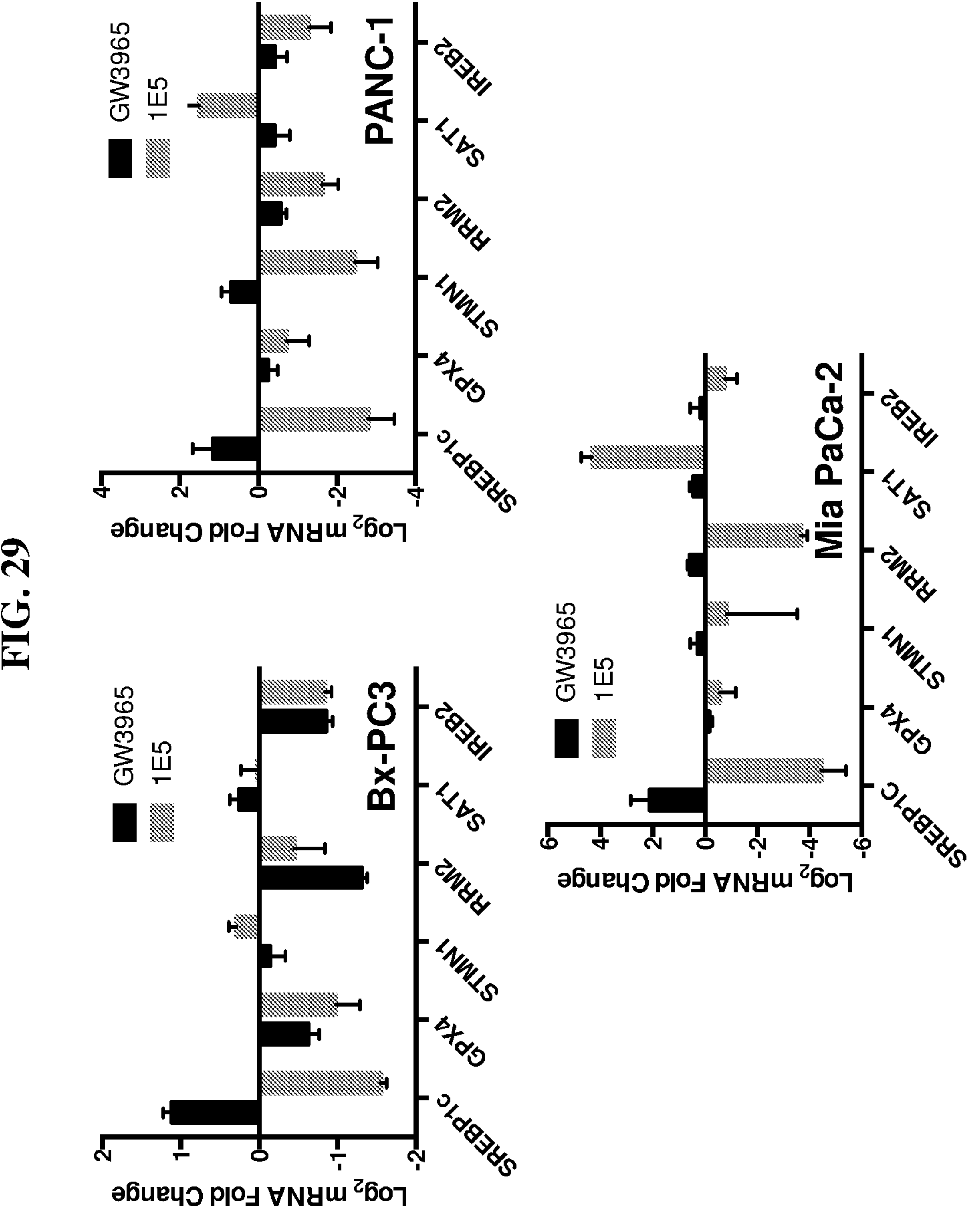
FIG. 29 shows quantitative PCR measurements of expression of select genes in pancreatic cancer cells following treatment with GW3965 and a LXR ligand according to preferred embodiments described herein.
Figure 30:
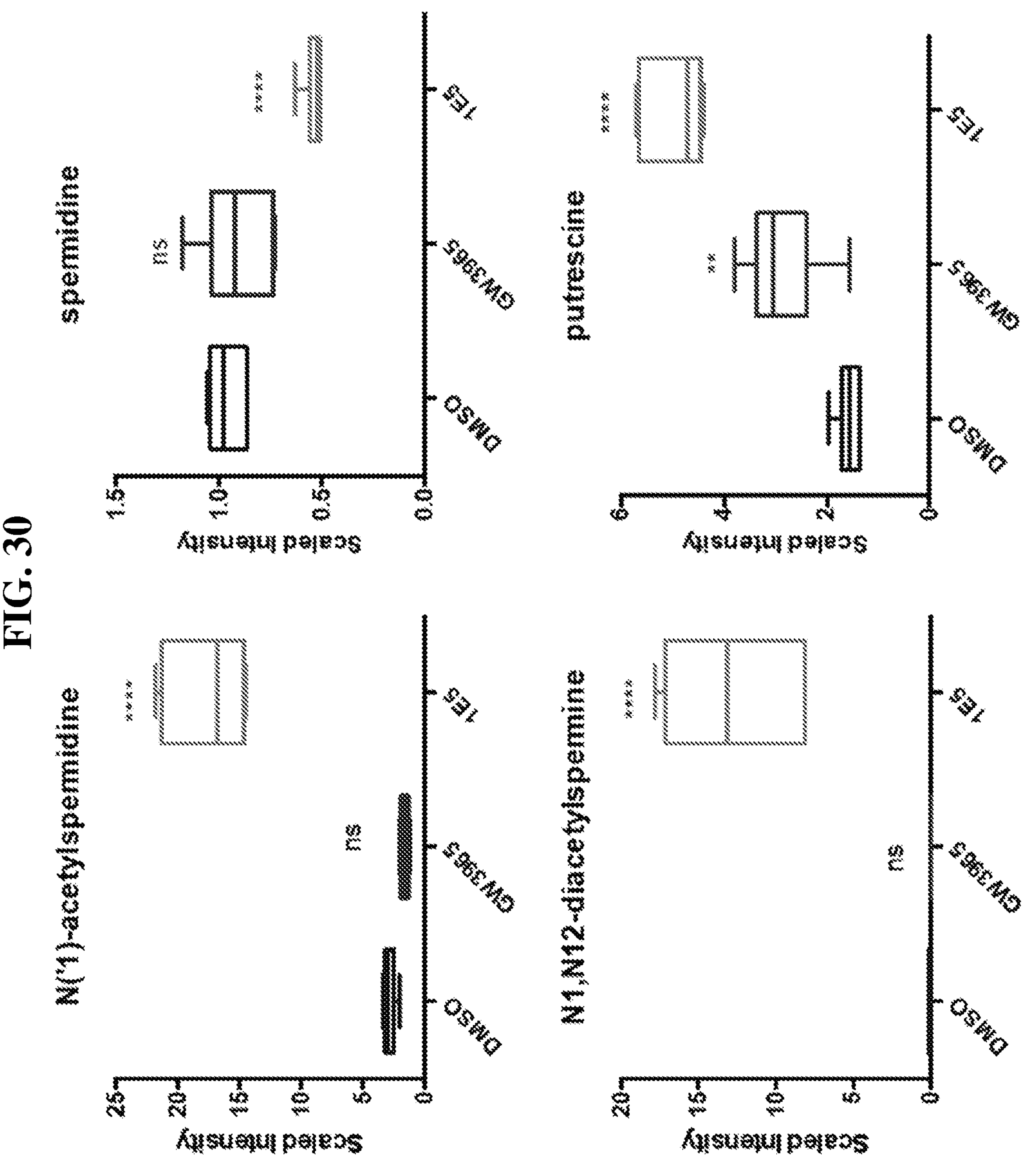
FIG. 30 shows levels of polyamine metabolites in pancreatic cancer cells after treatment with GW3965 and a LXR ligand according to preferred embodiments described herein.

FIG. 29 shows that treatments with LXR inverse agonist 1E5 differentially regulates the expression of genes involved in ferroptosis. FIG. 29 shows quantitative PCR measurements of select genes in pancreatic cancer cells, showing decreased expression of negative regulators and increased expression of positive regulator SAT1. Expression profiles of ferroptosis genes in RNAseq data following 1E5 treatment were also consistent with its pro-ferroptotic actions. Treatments with 1E5 decreased the expression of GPX4 gene along with other negative regulators of ferroptosis such as STMN1 and RRM2. However, it increases the expression of SAT1 (spermidine/spermine N-acetyltransferase 1) gene. SAT1 is the rate limiting enzyme of polyamine catabolism and is significantly down regulated in tumor samples. Polyamines are amino-acid derived polycationic alkylamines that are required for the growth of cells. SAT1 catalyzes the acetylation of spermidine and spermine to form N-acetylspermidine and N-acetylspermine respectively. FIG. 30 shows levels of polyamine metabolites in PANC-1 pancreatic cancer cells after treatment. Overexpression of SAT1 leads to depletion of spermidine and spermine and accumulation of putrescine, N-acetylspermidine and N-acetylspermine as seen in PDAC cells upon 1E5 treatment. SAT1 induces ferroptosis by upregulating the peroxidation of PUFA arachidonic acid. Ceramides are sphingolipids consisting of sphingosine and fatty acid acyl chain. Cellular stress leads to upregulation of ceramide synthesis which mediate caspase-dependent apoptosis. Accumulation of ceramides/hexosylceramides in the mitochondria leads to the formation of channel like structures in the mitochondrial outer membrane which increases the permeability of pro-apoptotic proteins such as cytochrome c. ER stress is also known to activate de-novo synthesis of ceramides and induce apoptosis by increasing the flow of Ca ions and upregulating the unfolded protein stress response.

Figure 31:
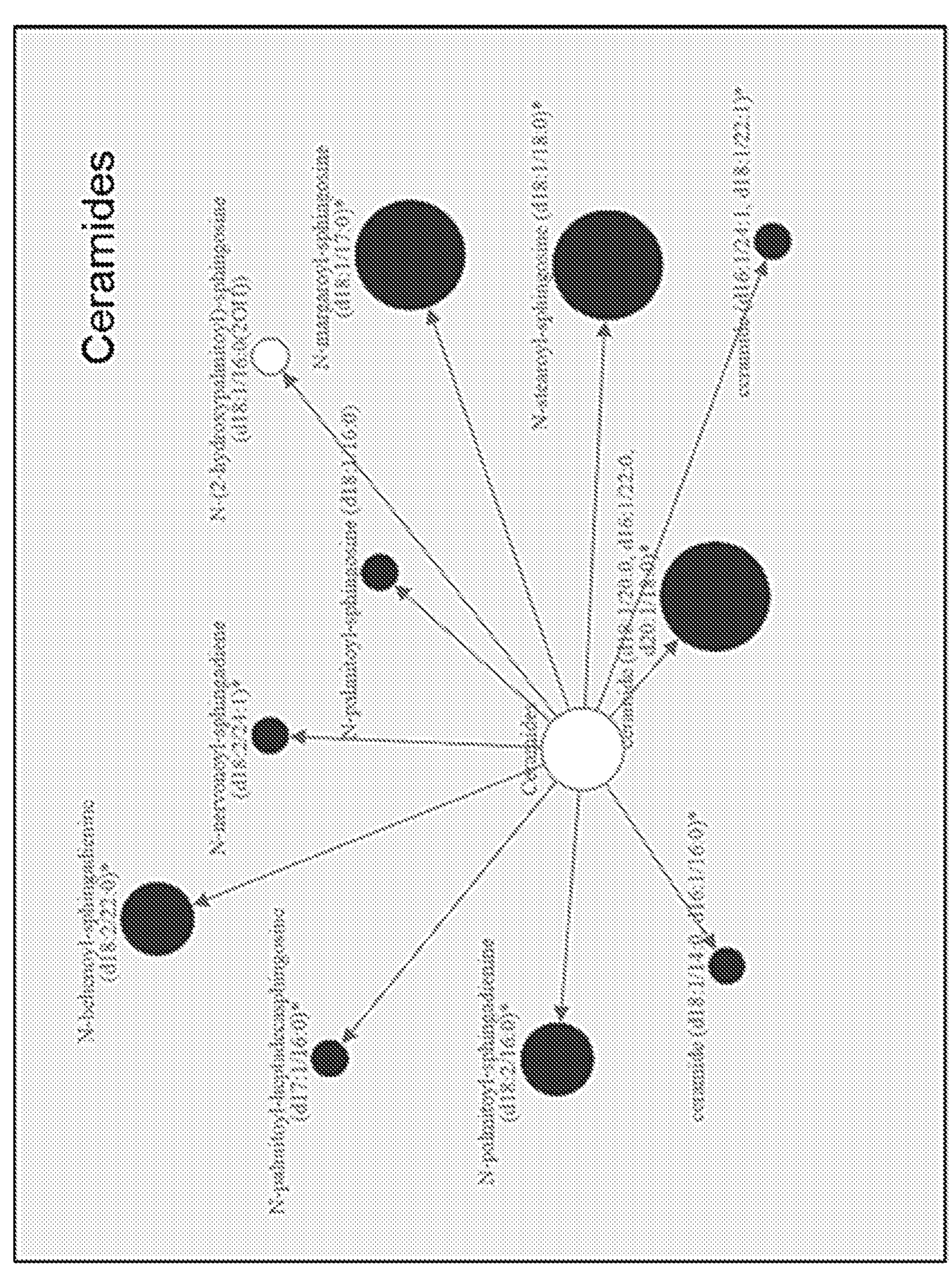
FIG. 31 shows levels of ceramide and hexosylceramide in pancreatic cancer cells determined by metabolomic analysis after treatment with a LXR ligand according to preferred embodiments described herein.

Accumulation of C18 ceramides in the mitochondria leads to the recruitment of auto phagosomes in mitochondria and induces LC3-ceramide dependent lethal mitophagy. FIG. 31 shows pro-apoptotic 3A4 induced elevated ceramide and hexosylceramide levels in pancreatic cancer cells in metabolomic analysis. Darkened circles indicate increases and the size of the circle corresponds to the significance of changes. In PDAC cells, 3A4 significantly upregulates the levels of C18 and C16 ceramides and hexosylceramides and induces caspase-dependent apoptosis.

Example 9

Characterization of 3A4 Derivative KD-01-39.

Figure 32:
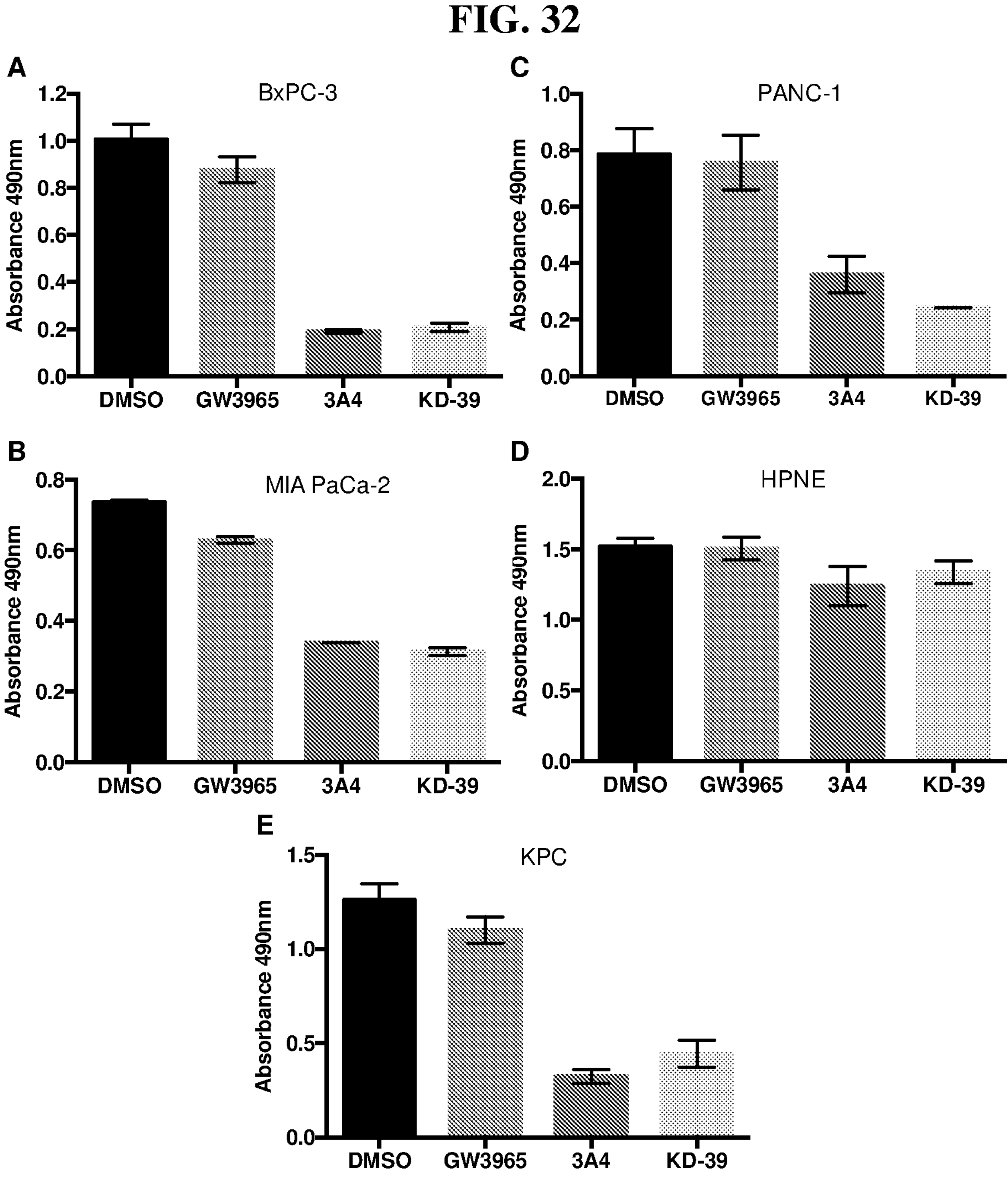
FIG. 32 shows inhibition of pancreatic cancer cells by 3A4 derivative KD-01-39 in (A-C) in human pancreatic cancer cell lines and (E) KPC mouse pancreatic tumor cells, having minimal effect on the (D) non-cancerous HPNE pancreatic cells.
Figure 33:
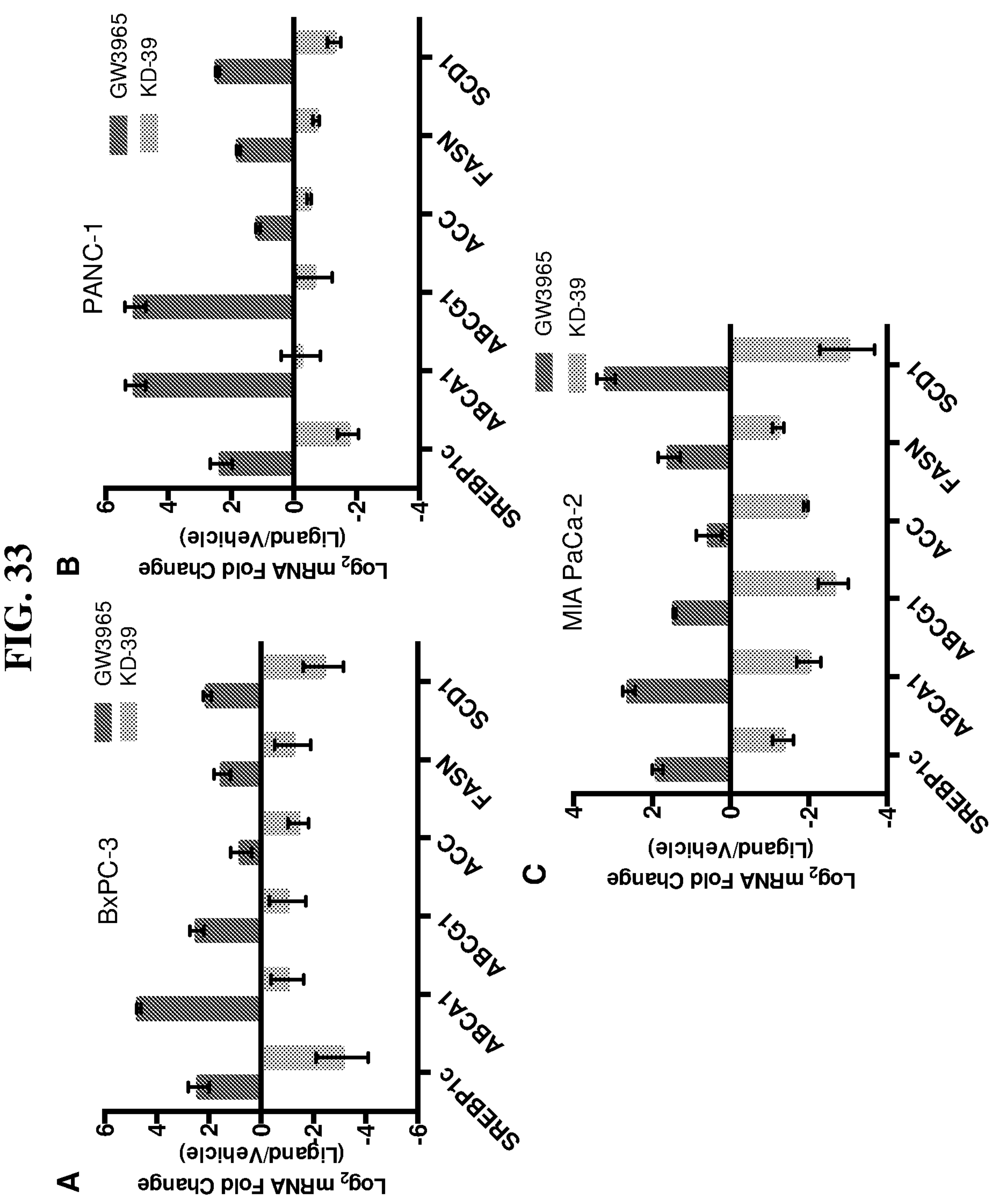
FIG. 33 shows down-regulation of LXR target gene expression by KD-01-39 in (A-C) three PDAC cell lines and support its function as an LXR inverse agonist.
Figure 34:
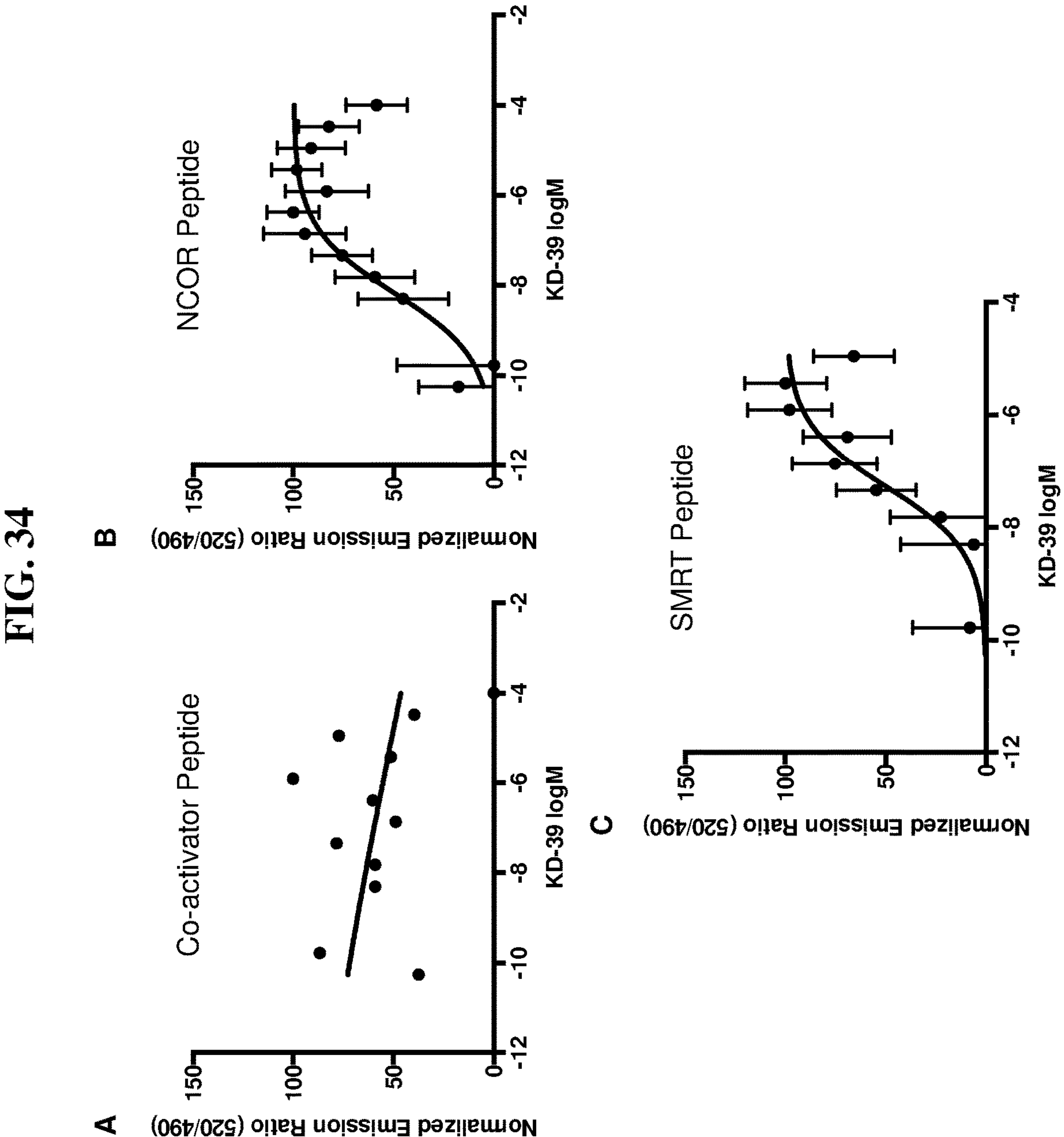
FIG. 34 shows that KD-01-39 does not facilitate the binding of (A) co-activator peptides to the LXR-LBD but increased recruitment and binding of (B) NCOR and (C) SMRT co-repressor peptides.
Figure 35:
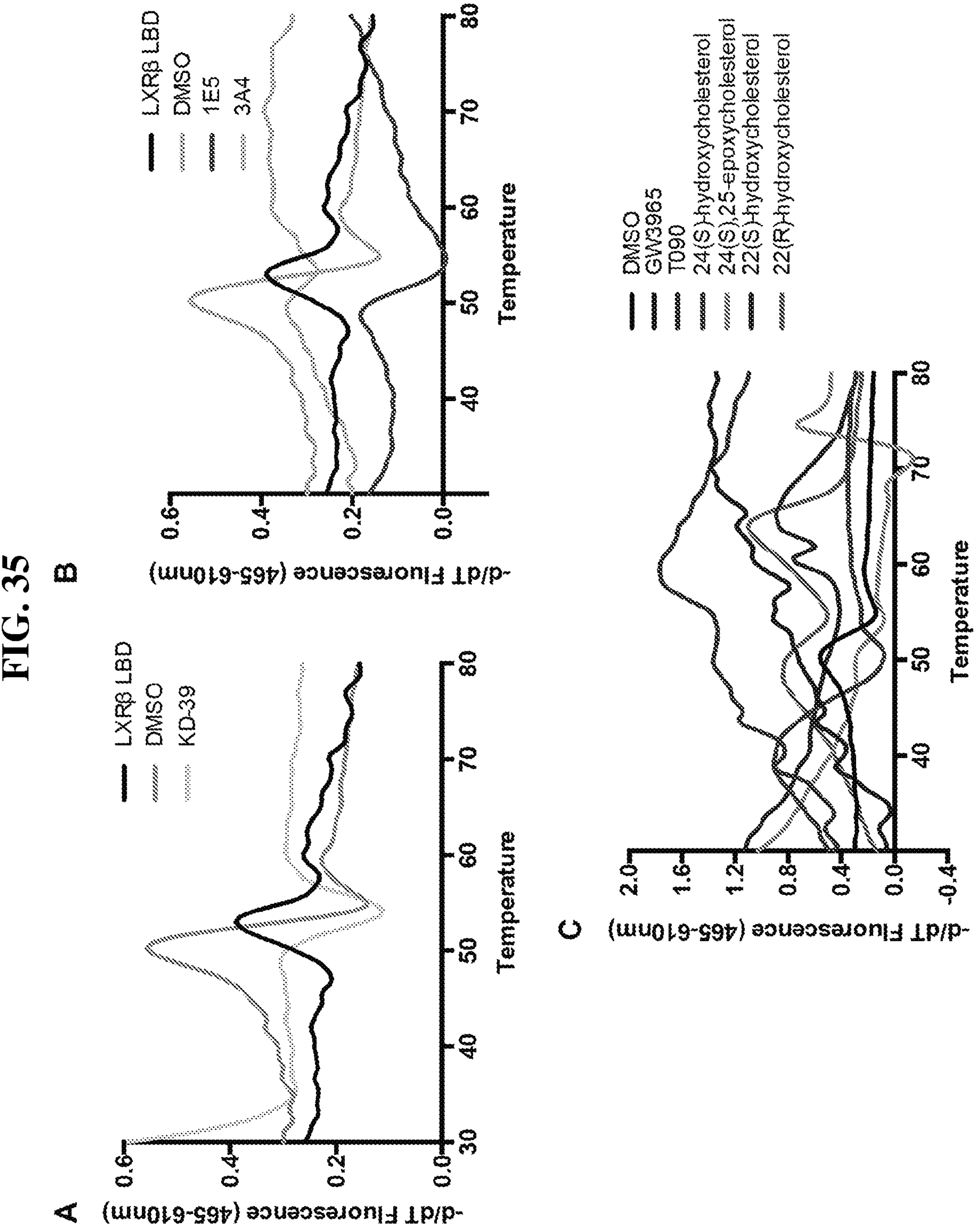
FIG. 35 shows data from differential scanning fluorimetry results which indicate that binding by (A) KD-01-39 and the two lead compounds (B)1E5 and 3A4 altered the structure of the LXR-LBD, and the results are consistent with the binding of (C) known natural and synthetic LXR ligands which also disrupt LXR-LBD structure when bound.

The synthesis and characterization of KD-01-39, a derivative of 3A4, have not been described previously. As shown in FIG. 32 (A-E), treatments of PDAC cells showed that KD-01-39 has the same or similar efficacy as 3A4 across all cancer lines tested and minimal effect on a non-cancerous pancreatic HPNE cells (see FIG. 32 (D). FIG. 33(A-C) shows that KD-01-39 decreased the expression of LXR target genes, similar to the activity shown by 3A4. FIG. 34 (A-C) shows that KD-01-39 did not affect recruitment of co-activator peptides to the LXR-LBD but enhanced recruitment of NCOR and SMRT co-repressor peptides in a dosage dependent manner FIG. 35 (A-C) shows the results from differential scanning fluorimetry assays which measured the effects of small molecule compounds on LXR-LBD structure. Addition of 1E5, 3A4, and KD-01-39 disrupted the LBD structure and dissociation dynamics of fluorescent dye molecules with increasing temperature. These results provide evidence that 1E5, 3A4, and 3A4 derivative KD-01-39 interact with the ligand-binding LBD of LXR and their ability to modulate LXR structure and function.

Example 10

LXR Agonists and Inverse Agonists and Cancer Immunotherapy.

LXRs are expressed in tumor cells and in a variety of other cell types, including immune cells. Two studies have demonstrated that modulating LXR activity using small molecule ligands can enhance the activation of the immune system to attack and eliminate cancer cells. In one study, treatments with LXR agonists GW3965 and RGX-104 blocked the recruitment and increased apoptosis of immunosuppressive myeloid-derived suppressor cells (MDSCs) by tumor cells and enhanced the anti-tumor effects of PD-1 inhibitor immunotherapy. A separate study using LXR inverse agonist SR9243 also similarly decreased MDSC recruitment to tumors and increased the expansion and recruitment of tumor-killing CD8+ T-cells. These findings suggest that 1E5, 3A4, and their derivatives which function as LXR inverse agonists can similarly promote the efficacy of immunotherapy.

REFERENCES

The following publications are hereby incorporated by reference.

Beaven, S. W., K. Wroblewski, J. Wang, C. Hong, S. Bensinger, H. Tsukamoto and P. Tontonoz (2011). "Liver X receptor signaling is a determinant of stellate cell activation and susceptibility to fibrotic liver disease." *Gastroenterology* 140(3): 1052-1062.

Biancur, D. E. and A. C. Kimmelman (2018). "The plasticity of pancreatic cancer metabolism in tumor progression and therapeutic resistance." *Biochim Biophys Acta.*

Brueggemeier, R. W., J. C. Hackett and E. S. Diaz-Cruz (2005). "Aromatase inhibitors in the treatment of breast cancer." *Endocrine reviews* 26(3): 331-345.

Candelaria, N. R., S. Addanki, J. Zheng, T. Nguyen-Vu, H. Karaboga, P. Dey, C. Gabbi, L. L. Vedin, K. Liu, W. Wu, P. K. Jonsson, J. Z. Lin, F. Su, L. R. Bollu, S. E. Hodges, A. L. McElhany, M. A. Issazadeh, W. E. Fisher, M. M. Ittmann, K. R. Steffensen, J. A. Gustafsson and C. Y. Lin (2014). "Antiproliferative effects and mechanisms of liver X receptor ligands in pancreatic ductal adenocarcinoma cells." *PLoS ONE* 9(9): e106289.

Carpenter, K. J., Valfort, A.-C., Steinauer, N., Chatterjee, A., Abuirqeba, S., Majidi, S., Sengupta, M., Di Paolo, R. J., Shornick, L. P., Zhang, J., and Flaveny, C. A. (2019). "LXR-inverse agonism stimulates immune-mediated tumor destruction by enhancing CD8 T-cell activity in triple negative breast cancer." Sci Rep 9(1):19530.

Dahlman, I, M. Nilsson, H. F. Gu, C. Lecoeur, S. Efendic, C. G. Ostenson, K. Brismar, J. A. Gustafsson, P. Froguel, M. Vaxillaire, K. Dahlman-Wright and K. R. Steffensen (2009). "Functional and genetic analysis in type 2 diabetes of liver X receptor alleles—a cohort study." *BMC Med Genet* 10: 27.

Deer, E. L., J. Gonzalez-Hernandez, J. D. Coursen, J. E. Shea, J. Ngatia, C. L. Scaife, M. A. Firpo and S. J. Mulvihill (2010). "Phenotype and genotype of pancreatic cancer cell lines." *Pancreas* 39(4): 425-435.

Flaveny, C. A., K. Griffett, D. El-Gendy Bel, M. Kazantzis, M. Sengupta, A. L. Amelio, A. Chatterjee, J. Walker, L. A. Solt, T. M Kamenecka and T. P. Burris (2015). "Broad Anti-tumor Activity of a Small Molecule that Selectively Targets the Warburg Effect and Lipogenesis." *Cancer Cell* 28(1): 42-56.

Gronemeyer, H., J. A. Gustafsson and V. Laudet (2004). "Principles for modulation of the nuclear receptor superfamily" *Nat Rev Drug Discov* 3(11): 950-964.

Hao, Q., J. B. Hansen, R. K. Petersen, P. Hallenborg, C. Jorgensen, S. Cinti, P. J. Larsen, K. R. Steffensen, H. Wang, S. Collins, J. Wang, J. A. Gustafsson, L. Madsen and K. Kristiansen (2010). "ADD1/SREBP1c activates the PGC1-alpha promoter in brown adipocytes." *Biochim Biophys Acta* 1801(4): 421-429.

Hingorani, S. R., L. Wang, A. S. Multani, C. Combs, T. B. Deramaudt, R. H. Hruban, A. K. Rustgi, S. Chang and D. A. Tuveson (2005). "Trp53R172H and KrasG12D cooperate to promote chromosomal instability and widely metastatic pancreatic ductal adenocarcinoma in mice." *Cancer Cell* 7(5): 469-483.

Hong, C., R. Walczak, H. Dhamko, M. N. Bradley, C. Marathe, R. Boyadjian, J. V. Salazar and P. Tontonoz (2011). "Constitutive activation of LXR in macrophages regulates metabolic and inflammatory gene expression: identification of ARL7 as a direct target." *J Lipid Res* 52(3): 531-539.

Hopkins, A. L. and C. R. Groom (2002). "The druggable genome." *Nature Reviews Drug Discovery* 1(9): 727-730.

Jakobsson, T., E. Treuter, J. A. Gustafsson and K. R. Steffensen (2012). "Liver X receptor biology and pharmacology: new pathways, challenges and opportunities." *Trends Pharmacol Sci* 33(7): 394-404.

Jordan, V. C. (2004). "Selective estrogen receptor modulation: concept and consequences in cancer." *Cancer Cell* 5(3): 207-213.

Lim, J. E., M. W. Chien and C. C. Earle (2003). "Prognostic factors following curative resection for pancreatic adenocarcinoma—A population-based, linked database analysis of 396 patients." *Annals of Surgery* 237(1): 74-85.

Lin, C. Y. and J. A. Gustafsson (2015). "Targeting liver X receptors in cancer therapeutics." *Nat Rev Cancer* 15(4): 216-224.

Moore, M. J., D. Goldstein, J. Hamm, A. Figer, J. R. Hecht, S. Gallinger, H. J. Au, P. Murawa, D. Walde and R. A. Wolff (2007). "Erlotinib plus gemcitabine compared with gemcitabine alone in patients with advanced pancreatic cancer: a phase III trial of the National Cancer Institute of Canada Clinical Trials Group." *Journal of clinical oncology* 25(15): 1960-1966.

Olive, K. P., M. A. Jacobetz, C. J. Davidson, A. Gopinathan, D. McIntyre, D. Honess, B. Madhu, M. A. Goldgraben, M. E. Caldwell, D. Allard, K. K. Frese, G. Denicola, C. Feig, C. Combs, S. P. Winter, H. Ireland-Zecchini, S. Reichelt, W. J. Howat, A. Chang, M. Dhara, L. Wang, F. Ruckert, R. Grutzmann, C. Pilarsky, K. Izeradjene, S. R. Hingorani, P. Huang, S. E. Davies, W. Plunkett, M. Egorin, R. H. Hruban, N. Whitebread, K. McGovern, J. Adams, C. Iacobuzio-Donahue, J. Griffiths and D. A. Tuveson (2009). "Inhibition of Hedgehog signaling enhances delivery of chemotherapy in a mouse model of pancreatic cancer." *Science* 324(5933): 1457-1461.

Olive, K. P., M. A. Jacobetz, C. J. Davidson, A. Gopinathan, D. McIntyre, D. Honess, B. Madhu, M. A. Goldgraben, M. E. Caldwell, D. Allard, K. K. Frese, G. DeNicola, C. Feig, C. Combs, S. P. Winter, H. Ireland-Zecchini, S. Reichelt, W. J. Howat, A. Chang, M. Dhara, L. F. Wang, F. Ruckert, R. Grutzmann, C. Pilarsky, K. Izeradjene, S. R. Hingorani, P. Huang, S. E. Davies, W. Plunkett, M. Egorin, R. H. Hruban, N. Whitebread, K. McGovern, J. Adams, C. Iacobuzio-Donahue, J. Griffiths and D. A. Tuveson (2009). "Inhibition of Hedgehog Signaling Enhances Delivery of Chemotherapy in a Mouse Model of Pancreatic Cancer." *Science* 324(5933): 1457-1461.

Ou, Y., S. J. Wang, D. Li, B. Chu and W. Gu (2016). "Activation of SAT1 engages polyamine metabolism with p53-mediated ferroptotic responses." *Proc Natl Acad Sci USA* 113(44): E6806-E6812.

Pencheva, N., C. G. Buss, J. Posada, T. Merghoub and S. F. Tavazoie (2014). "Broad-spectrum therapeutic suppression of metastatic melanoma through nuclear hormone receptor activation." *Cell* 156(5): 986-1001.

Sentelle, R. D., C. E. Senkal, W. Jiang, S. Ponnusamy, S. Gencer, S. P. Selvam, V. K. Ramshesh, Y. K. Peterson, J. J. Lemasters, Z. M. Szulc, J. Bielawski and B. Ogretmen (2012). "Ceramide targets autophagosomes to mitochondria and induces lethal mitophagy." *Nat Chem Biol* 8(10): 831-838.

Tavazoie, M. F., I. Pollack, R. Tanqueco, B. N. Ostendorf, B. S. Reis, F. C. Gonsalves, I. Kurth, C. Andreu-Agullo, M. L. Derbyshire, J. Posada, S. Takeda, K. N. Tafreshian, E. Rowinsky, M. Szarek, R. J. Waltzman, E. A. McMillan, C. Zhao, M. Mita, A. Mita, B. Chmielowski, M. A. Postow, A. Ribas, D. Mucida and S. F. Tavazoie (2018). "LXR/ApoE Activation Restricts Innate Immune Suppression in Cancer." *Cell* 172(4): 825-840 e818.

Viennois, E., K. Mouzat, J. Dufour, L. Morel, J. M. Lobaccaro and S. Baron (2012). "Selective liver X receptor modulators (SLiMs): what use in human health?" *Mol Cell Endocrinol* 351(2): 129-141.

Xiong, H. Q., A. Rosenberg, A. LoBuglio, W. Schmidt, R. A. Wolff, J. Deutsch, M. Needle and J. L. Abbruzzese (2004). "Cetuximab, a monoclonal antibody targeting the epidermal growth factor receptor, in combination with gemcitabine for advanced pancreatic cancer: a multicenter phase II Trial." *J Clin Oncol* 22(13): 2610-2616.

Yang, S., S. Hwang, M. Kim, S. B. Seo, J. H. Lee and S. M. Jeong (2018). "Mitochondrial glutamine metabolism via GOT2 supports pancreatic cancer growth through senescence inhibition." *Cell Death Dis* 9(2): 55.

Yang, W. S., K. J. Kim, M. M. Gaschler, M. Patel, M. S. Shchepinov and B. R. Stockwell (2016). "Peroxidation of polyunsaturated fatty acids by lipoxygenases drives ferroptosis." *Proc Natl Acad Sci USA* 113(34): E4966-4975.

What is claimed is:

1. A method for inhibiting tumor growth in a patient with advanced pancreatic cancer, triple-negative breast cancer or estrogen receptor-positive breast cancer, comprising administering a pharmaceutical formulation to the patient and modulating liver X receptor activity in the patient, wherein the pharmaceutical formulation comprises a therapeutically effective amount of a compound of formula:

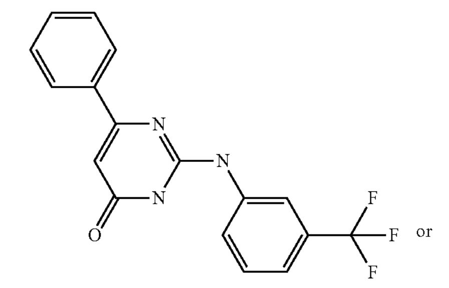

or

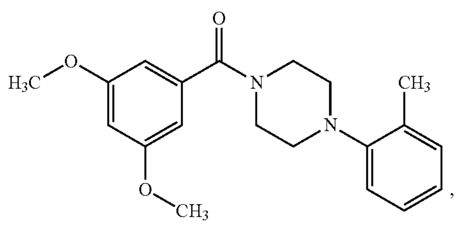

or a pharmacologically acceptable salt thereof.

2. A method for treating cancer in a patient with advanced pancreatic cancer, triple-negative breast cancer or estrogen receptor-positive breast cancer, comprising administering a pharmaceutical formulation to the patient and modulating liver X receptor activity in the patient, wherein the pharmaceutical formulation comprises a therapeutically effective amount of a compound of formula:

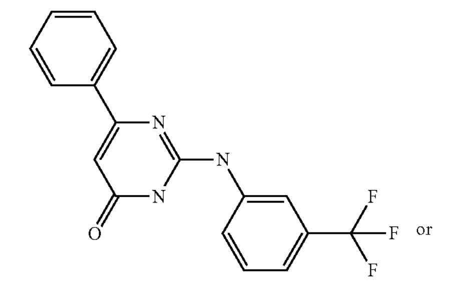

or

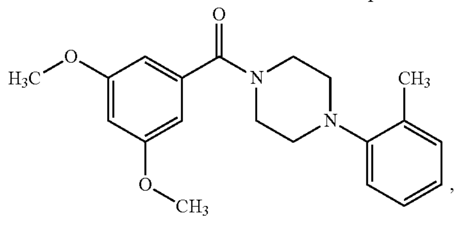

or a pharmacologically acceptable salt thereof.

3. A method for inhibiting tumor growth in a patient with advanced pancreatic cancer, triple-negative breast cancer or estrogen receptor-positive breast cancer, comprising administering a pharmaceutical formulation to the patient and modulating liver X receptor activity in the patient, wherein the pharmaceutical formulation comprises a therapeutically effective amount of a compound of formula:

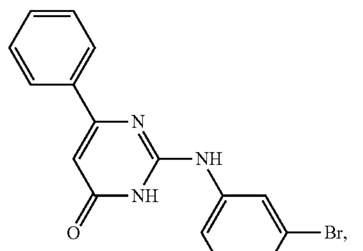

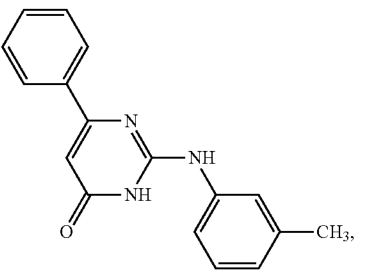

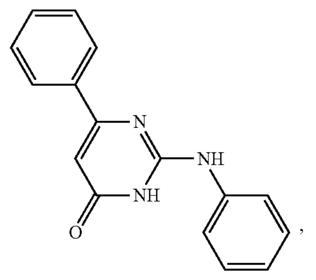

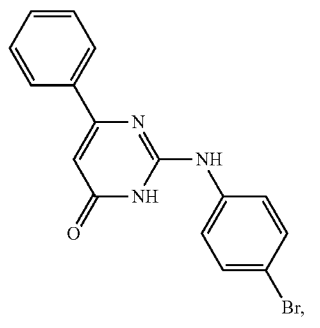

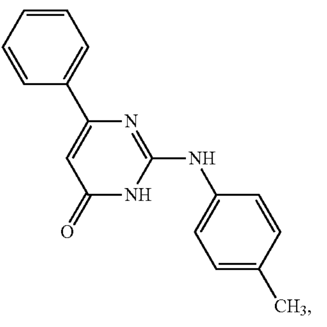

-continued
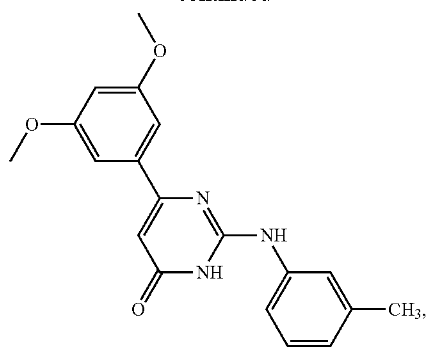
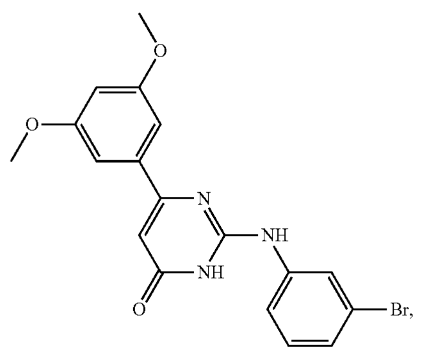
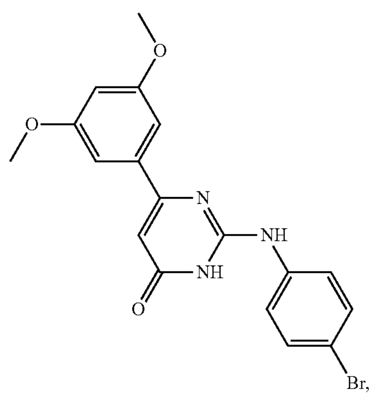
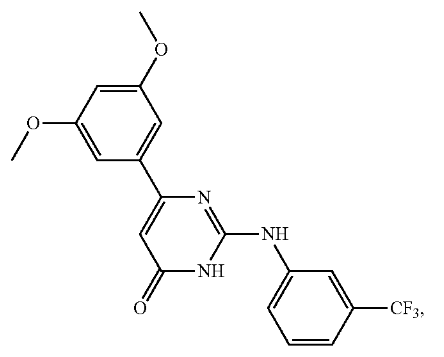
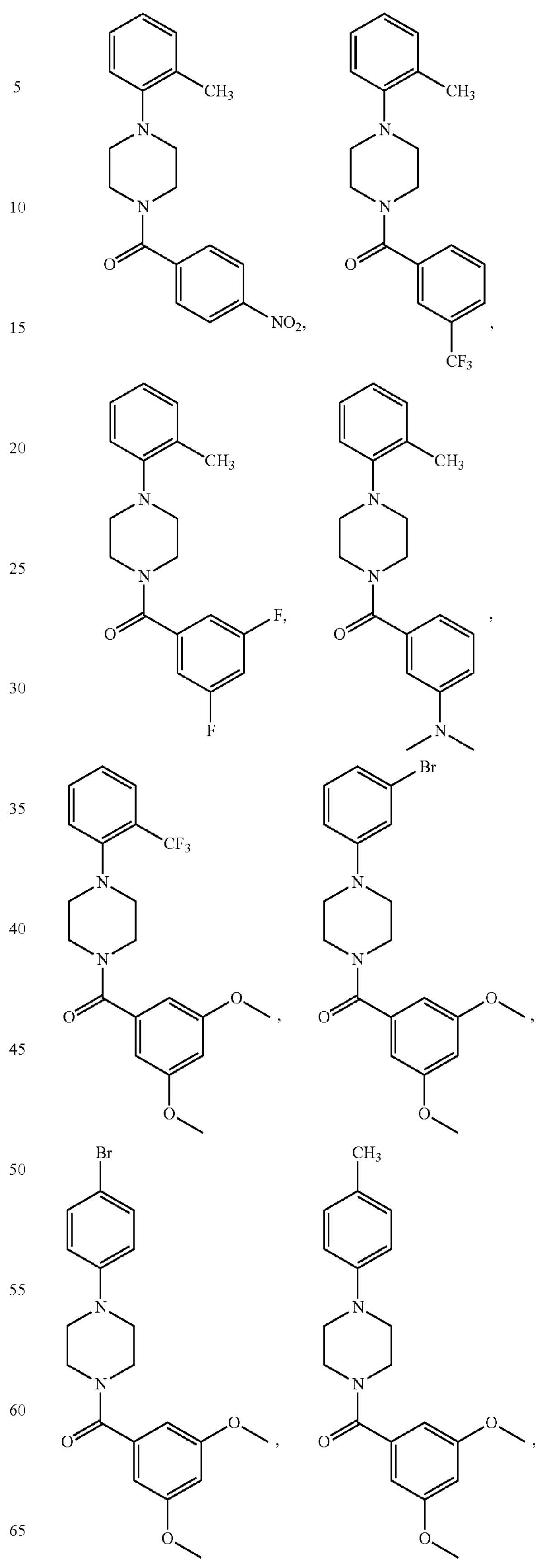

-continued

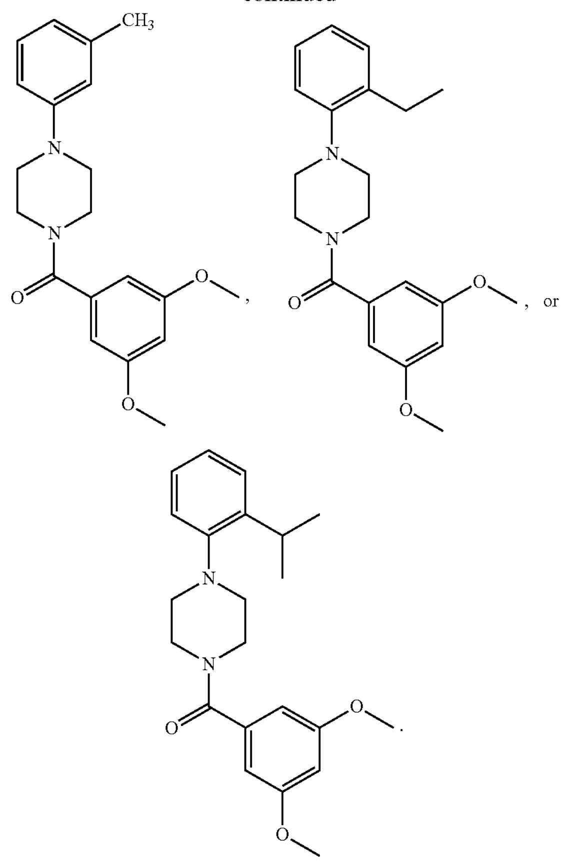

, or

4. A method for treating cancer in a patient with advanced pancreatic cancer, triple-negative breast cancer or estrogen receptor-positive breast cancer, comprising administering a pharmaceutical formulation to the patient and modulating liver X receptor activity in the patient, wherein the pharmaceutical formulation comprises a therapeutically effective amount of a compound of formula:

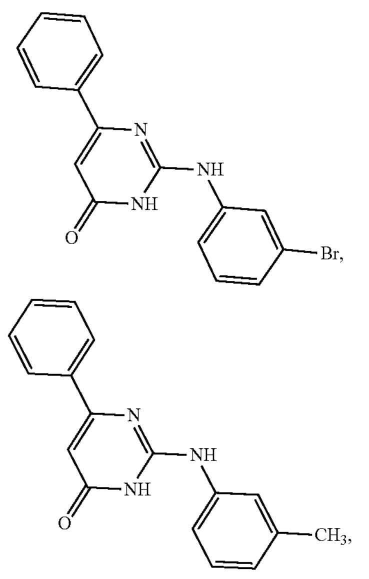

-continued

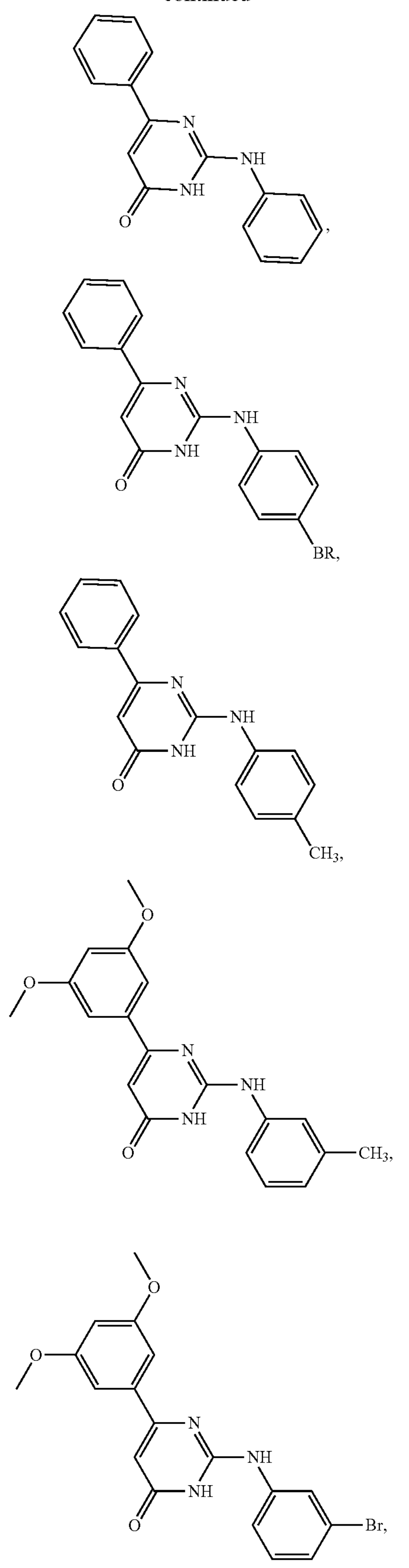

-continued
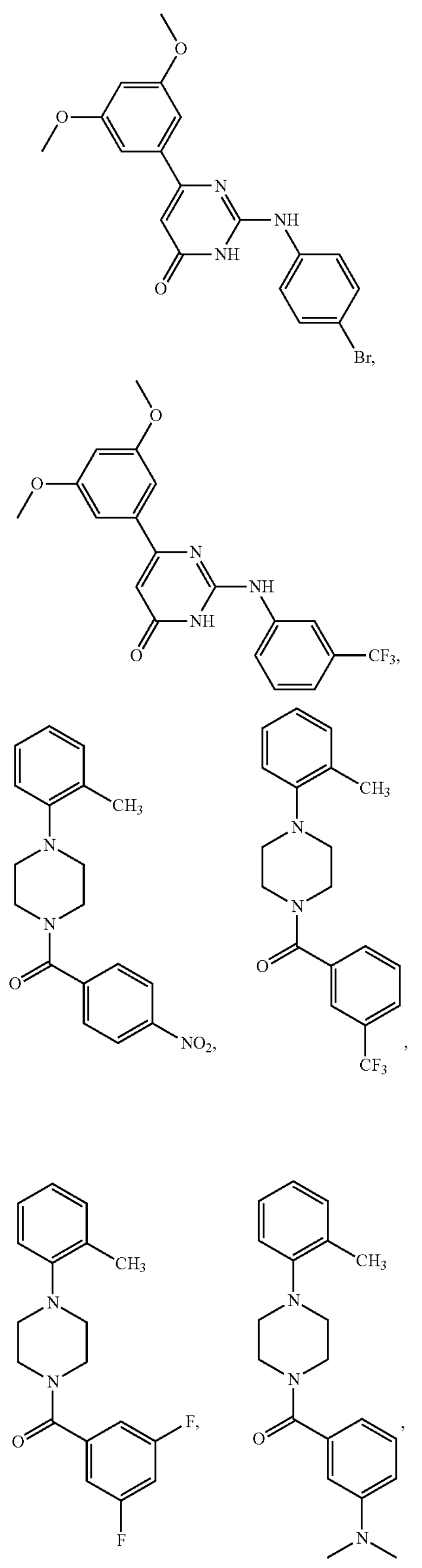
-continued
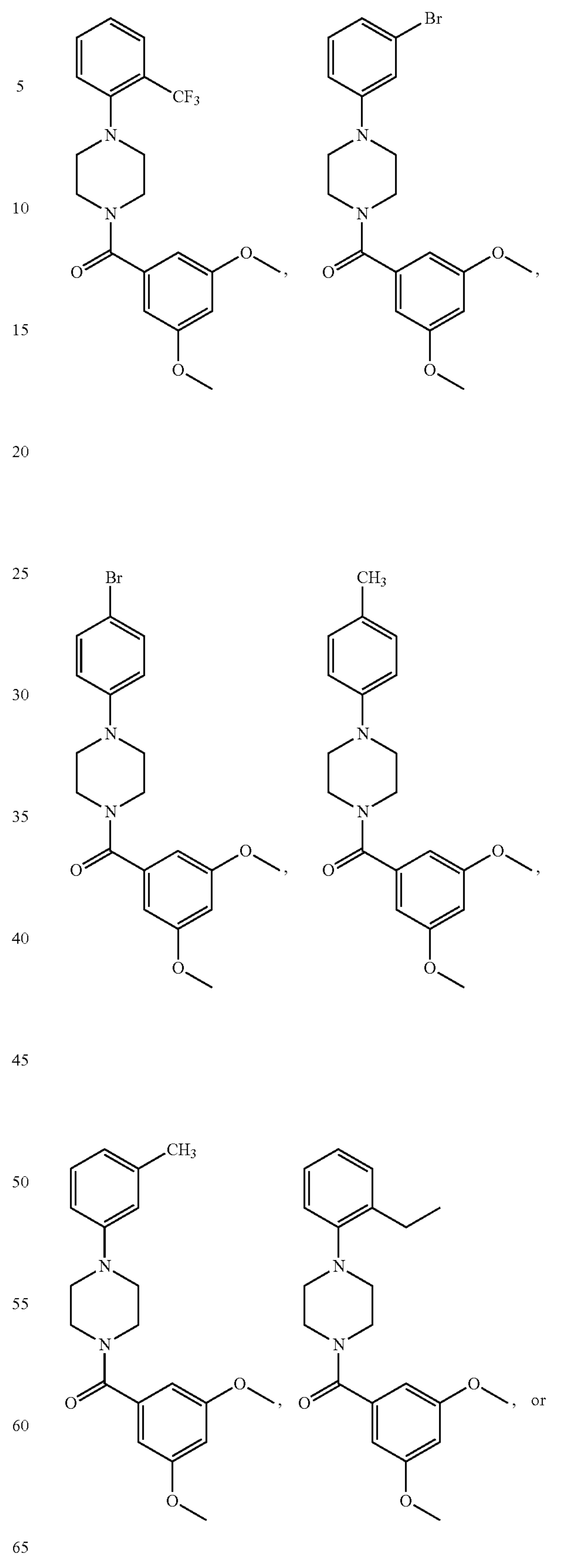
or

-continued
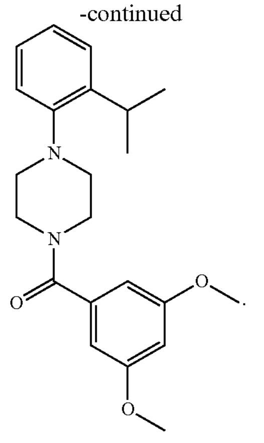
* * * * *